(12) United States Patent
Koh et al.

(10) Patent No.: US 8,063,049 B2
(45) Date of Patent: *Nov. 22, 2011

(54) INHIBITORS OF MEK

(75) Inventors: Yung-hyo Koh, Irvine, CA (US); Zhi Hong, Chapel Hill, NC (US); Jean-Michel Vernier, Laguna Niguel, CA (US); Andreas Maderna, Stony Point, NY (US)

(73) Assignee: Ardea Biosciences, Inc., Costa Mesa, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 12/879,314

(22) Filed: Sep. 10, 2010

(65) Prior Publication Data

US 2010/0331334 A1    Dec. 30, 2010

Related U.S. Application Data

(63) Continuation of application No. 12/016,897, filed on Jan. 18, 2008, now Pat. No. 7,820,664.

(60) Provisional application No. 60/885,849, filed on Jan. 19, 2007.

(51) Int. Cl.
*A61K 31/502* (2006.01)
*A61K 31/517* (2006.01)
*A61K 31/47* (2006.01)
*C07D 237/28* (2006.01)
*C07D 239/74* (2006.01)
*C07D 215/38* (2006.01)

(52) U.S. Cl. .................. 514/248; 514/266.1; 514/311; 544/235; 544/283; 546/171

(58) Field of Classification Search .................. 514/248, 514/259.3, 266.1, 300, 311; 544/235, 283; 546/115, 118, 119, 121, 171
See application file for complete search history.

(56) References Cited

U.S. PATENT DOCUMENTS

| | | | |
|---|---|---|---|
| 5,861,510 A | 1/1999 | Piscopio et al. | |
| 5,863,949 A | 1/1999 | Robinson et al. | |

FOREIGN PATENT DOCUMENTS

| | | |
|---|---|---|
| EP | 0606046 | 7/1994 |
| EP | 0679641 A1 | 11/1995 |
| EP | 0780386 | 6/1997 |
| EP | 97304971.1 | 7/1997 |
| EP | 99302232.1 | 3/1999 |
| EP | 0931788 | 7/1999 |
| EP | 99308617.2 | 10/1999 |
| WO | WO 90-05719 A1 | 5/1990 |
| WO | WO 96-27583 A1 | 3/1996 |
| WO | WO 96-33172 A1 | 10/1996 |
| WO | WO 98-03516 A1 | 1/1998 |
| WO | WO 98-07697 A1 | 2/1998 |
| WO | WO 98-30566 A1 | 7/1998 |
| WO | WO 98-33768 A1 | 8/1998 |
| WO | WO 98-34915 A1 | 8/1998 |
| WO | WO 98-34918 A1 | 8/1998 |
| WO | WO 99-07675 A1 | 2/1999 |
| WO | WO 99-29667 A1 | 6/1999 |
| WO | WO 99-32889 A1 | 10/1999 |
| WO | WO 99-52910 A1 | 10/1999 |
| WO | WO 2000-74681 A1 | 12/2000 |
| WO | WO 2004-031174 | 4/2004 |
| WO | WO 2004-083167 A1 | 9/2004 |
| WO | WO 2005-051302 A1 | 6/2005 |
| WO | WO 2005-051906 A1 | 6/2005 |

OTHER PUBLICATIONS

U.S. Appl. No. 60/148,464, filed Aug. 12, 1999.
Ahn et al., "Transformation of Mammalian Cells by Constitutively Active MAP Kinase Kinase," Science 265;966-970 (1994).
Li, C. et al., "Cyclooxygenase-2 Inhibitors. Synthesis and Pharmacological Activities of 5-Methanesulfonamido-1-indanone Derivatives," J. Med. Chem. 38:4897-4905 (1995).
PCT/US08/051518 Search Report dated May 21, 2008.
Fleischer et al., "Improved oral drug delivery: solubility limitations overcome by the use of prodrugs," Adv. Drug Del. Rev. 19:115-130 (1996).
Robinson et al., "Discovery of the Hemifumarate and (α-L-Alanyloxy)methyl Ether as Prodrugs of an Antirheumatic Oxindole: Prodrugs for the Enolic OH Group," J. Med. Chem. 39:10-18 (1996).
Vippagunta et al., Crystalline solids, 2001, Advanced Drug Delivery Reviews, 48, pp. 3 and 18.
Wolff et al., Burger's Medicinal Chemistry and Drug Discovery, 1994, Wiley-Interscience, Fifth Edition, vol. I: Principles and Practice, pp. 975-977.
Kwon et al., Handbook of Essential Pharmacokinetics, Pharmacodynamics and Drug Metabolism for Industrial Scientists, 2001, http://www.myilibrary.com/Browse/open.asp?ID=4284&loc=1, Retrieved from the Internet Jun. 16, 2008, p. 213.
Metabolomics [online], Retrieved from the Internet Jun. 16, 2008, URL: http://www.en.wikipedia.org/wiki/Metabolomics, p. 1.
Lala et al., Role of nitric oxide in tumor progression: Lessons from experimental tumors, Cancer and Metastasis Reviews (1998), 17, 91-106.
Golub et al., Molecular Classification of Cancer: Class Discovery and Class Prediction by Gene Expression Monitoring, Science (1999), vol. 286, 531-537.

*Primary Examiner* — Kamal Saeed
*Assistant Examiner* — Kristin Bianchi
(74) *Attorney, Agent, or Firm* — Millen, White, Zelano & Branigan, P.C.

(57) ABSTRACT

This invention concerns to N-(2-aylamino)aryl sulfonamides, which are inhibitors of MEK, methods of using such compounds in the treatment of hyperproliferative diseases, and to pharmaceutical compositions containing such compounds.

20 Claims, No Drawings

INHIBITORS OF MEK

RELATED APPLICATION

This application is a continuation application of U.S. patent application Ser. No. 12/016,897, filed on Jan. 18, 2008, now U.S. Pat. No. 7,820,664 and claims the benefit of U.S. Provisional Application Ser. No. 60/885,849, filed on Jan. 19, 2007.

BACKGROUND OF THE INVENTION

Cell signaling pathways play an important role in cell growth, proliferation and differentiation. In normal cell growth, growth factors, through receptor activation (e.g. PDGF or EGF), activate MAP kinase pathways. The Ras/Raf kinase pathway is one of the most important and most well understood MAP kinase pathways involved in normal and uncontrolled cell growth. Active GTP-bound Ras leads to the activation of a cascade of serine/threonine kinases. One of the several groups of kinases known to require GTP-bound Ras for their activation is the Raf family. Upon activation Raf phosphorylates "mitogen-activated ERK activating kinases" (MEK)-1 and MEK2.

Some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers. Recently, bRaf mutations have been identified in more than 60% of malignant melanoma.

These mutations in bRaf result in a constitutively active MAP kinase cascade. Studies of primary tumor samples and cell lines have also shown constitutive or over activation of the MAP kinase pathway in cancers of pancreas, colon, lung, ovary and kidney. Hence, there is a strong correlation between cancers and an overactive MAP kinase pathway resulting from genetic mutations.

As constitutive or over activation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2.

Inhibition of MEK has been shown to have potential therapeutic benefit in several studies. For example, small molecule MEK inhibitors have been shown to inhibit human tumor growth in nude mouse xenografts, block static allodynia in animals and inhibit growth of acute myeloid leukemia cells.

Thus, MEK1 and MEK2 are validated and accepted targets for anti-proliferative therapies, even when the oncogenic mutation does not affect MEK structure or expression.

The MEK cascade has also been implicated in inflammatory diseases and disorders. This includes both acute and chronic inflammation disorders. Examples of such disorders are allergic contact dermatitis, rheumatoid arthritis, osteoarthritis, inflammatory bowel diseases, chronic obstructive pulmonary disorder, psoriasis, multiple sclerosis, asthma, diseases and disorders related to diabetic complications, and inflammatory complications of the cardiovascular system such as acute coronary syndrome. Among inflammatory bowel diseases are Crohn's disease and ulcerative colitis.

SUMMARY OF THE INVENTION

The invention provides compounds of and methods of utilizing such compounds. The compounds and the pharmaceutically acceptable salts, prodrugs, derivatives, esters, hydrates and solvates thereof of this invention are useful, e.g. in the treatment of diseases, e.g. hyperproliferative diseases. In one aspect, the invention provides compounds, including pharmaceutically acceptable salts, prodrugs, derivatives, esters, hydrates and solvates thereof having the general formula I:

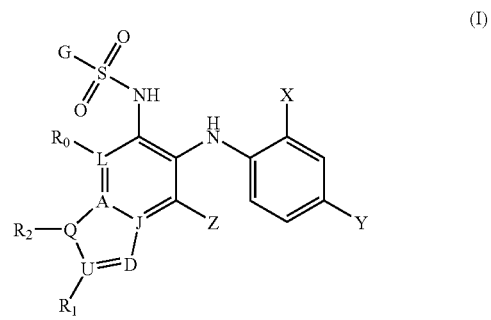

(I)

where G is $R_{1a}$, $R_{1b}$, $R_{1c}$, $R_{1d}$, $R_{1e}$, $Ar_1$, $Ar_2$ or $Ar_3$; $R_o$, $R_1$ and $R_2$ are independently selected from H, halogen, cyano, cyanomethyl, nitro, difluoromethoxy, difluoromethoxy, trifluoromethyl, azido, $CO_2R_5$, $OR_5$, —O—(CO)—$R_5$, —O—C(O)—N($R_5$)$_2$, —NR$_5$C(O)NR$_6$R$_7$, —SR$_5$, NHC(O)R$_5$, —NHSO$_2$R$_5$, SO$_2$N(R$_5$)$_2$, C1-C6 alkyl, C1-C4 alkoxy, C3-C6 cycloalkyl, C2-C6 alkenyl, C2-C6 alkynyl, aryl, alkylaryl, arylalkyl, heterocyclic, said alkyl, cycloalkyl, alkenyl, aryl, alkylaryl, arylalkyl, heterocyclic and alkynyl groups optionally substituted with 1-3 substituents selected independently from halogen, OH, CN, cyanomethyl, nitro, phenyl, difluoromethoxy, difluoromethoxy, and trifluoromethyl, and said C1-C6 alkyl and C1-C4 alkoxy groups also optionally substituted with $OCH_3$ or $OCH_2CH_3$, wherein each $R_5$ is selected from H, lower alkyl, substituted lower alkyl, aryl, or substituted aryl, and $NR_5R_6$, wherein each $R_6$ and $R_7$ are independently selected from hydrogen or lower alkyl; X is F, Br, I, Cl or methyl; Y is I, Br, Cl, $CF_3$, C1-C3 alkyl, C2-C3 alkenyl, C2-C3 alkynyl, cyclopropyl, phenyl, pyridyl, pyrazolyl, OMe, OEt, or SMe, where all said methyl, ethyl, C1-C3 alkyl, and cyclopropyl groups of X and Y are optionally substituted with OH, all said phenyl, pyridyl, pyrazolyl groups of Y are optionally substituted with halogen, acetyl, methyl, and trifluoromethyl, and all said methyl groups of X and Y are optionally substituted with one, two, or three F atoms; Z is H, F, Br, I, or Cl; and A, D, J, L, Q, U are independently selected from C, —NH, N, O, and —N(CH$_3$)—.

$R_{1a}$ is methyl, optionally substituted with 1-3 fluorine atoms or 1-3 chlorine atoms, or with OH, cyclopropoxy, or C1-C4 alkoxy, where the C1-C4 alkyl moieties of said C1-C4 alkoxy groups are optionally substituted with one hydroxy or methoxy group, and where all C2-C4 alkyl groups within said C1-C4 alkoxy are optionally further substituted with a second OH group.

$R_{1b}$ is CH(CH$_3$)—C1-3 alkyl or C3-C6 cycloalkyl, said methyl, alkyl, and cycloalkyl groups optionally substituted with 1-3 substituents selected independently from F, Cl, Br, I, OH, C1-C4 alkoxy, and CN.

$R_{1c}$ is $(CH_2)_nO_mR'$, where m is 0 or 1; where, when m is 1, n is 2 or 3, and when m is 0, n is 1 or 2; and where R' is C1-C6 alkyl, optionally substituted with 1-3 substituents selected independently from F, Cl, OH, $OCH_3$, $OCH_2CH_3$, and C3-C6 cycloalkyl;

$R_{1d}$ is $C(A')(A'')(B)$— where B, A', and A'' are, independently, H or C1-4 alkyl, optionally substituted with one or two OH groups or halogen atoms, or A' and A'', together with the carbon atom to which they are attached, form a 3- to 6-member saturated ring, said ring optionally containing one or two heteroatoms selected, independently, from O, N, and S and optionally substituted with one or two groups selected independently from methyl, ethyl, and halo.

$R_{1e}$ is benzyl or 2-phenyl ethyl, in which the phenyl group is optionally substituted

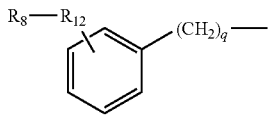

where q is 1 or 2, $R_8$, $R_9$ and $R_{10}$ are, independently, H, F, Cl, Br, I, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, and $R_{10}$ may also be nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazolyl, N-morpholinyl carbonylamino, N-morpholinylsulfonyl, and N-pyrrolidinylcarbonylamino; $R_{11}$ and $R_{12}$ are, independently, H, F, Cl, or methyl.

$Ar_1$ is

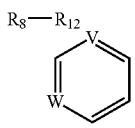

where W and V are, independently, N, $CR_2$ or $CR_3$; $R_3$, $R_8$, $R_8$ and $R_{10}$ are, independently, H, F, Cl, Br, I, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, and $R_{10}$ may also be nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholinylcarbonylamino, N-morpholinylsulfonyl and Npyrrolidinylcarbonylamino; $R_{11}$ and $R_{12}$ are, independently, H, F, Cl or methyl.

$Ar_2$ is

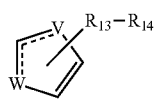

where the dashed line represents a double bond which may be located formally either between V and the carbon between W and V, or between W and the carbon between W and V; where W is —S—, —O— or —N= and where; when W is —O— or —S—, V is —CH=, —CCl= or —N=; and when W is —N=, V is CH=, or —NCH3-; $R_{13}$ and $R_{14}$ are, independently, H, methoxycarbonyl, methylcarbamoyl, acetamido, acetyl, methyl, ethyl, trifluoromethyl, or halogen.

$Ar_3$ is

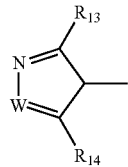

where W is —NH—, —NCH3- or —O—; and $R_{13}$ and $R_8$ are, independently, H, F, Cl, or methyl.

In another aspect the invention provides compounds, including pharmaceutically acceptable salts, esters, prodrugs, solvates, hydrates or derivatives thereof of the general formula II:

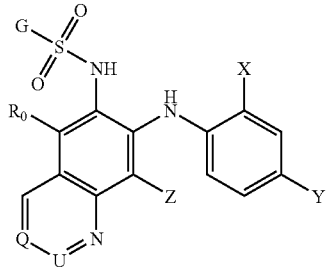

(II)

where G, $R_o$, X, Y, Z Q and U are as defined above.

Such compounds are inhibitors of MEK and are useful in treatment of cancer and other hyperproliferative diseases.

This invention is also directed to pharmaceutical compositions comprising pharmaceutically effective amounts of a compound of formula I and/or formula II or a pharmaceutically acceptable salt, ester, prodrug, solvate, hydrate or derivative thereof, and a pharmaceutically acceptable carrier. Such compositions may contain adjuvants, excipients, preservatives, agents for delaying absorption, fillers, binders, adsorbents, buffers, disintegrating agents, solubilizing agents, other carriers, and other inert ingredients. Methods of formulation of such compositions are well-known in the art.

The invention is also directed to a method of treating a hyperproliferative disorder in a mammal, including a human, comprising administering to said mammal a therapeutically effective amount of the compound of formula I and/or formula II, or a pharmaceutically acceptable salt, ester, prodrug, solvate, hydrate or derivative thereof.

This invention is also directed to a method of treating an inflammatory disease, condition, or disorder in a mammal, including a human, comprising administering to said mammal a therapeutically effective amount of the compound of formula I and/or II, or a pharmaceutically acceptable salt, ester, prodrug, solvate, hydrate or derivative thereof.

The invention is also directed to a method of treating a disorder or condition which is modulated by the MEK cascade in a mammal, including a human, comprising administering to said mammal an amount of the compound of formula I and/or II, or a pharmaceutically acceptable salt, ester, prodrug, solvate, hydrate or derivative thereof, effective to modulate said cascade. The appropriate dosage for a particular patient can be determined, according to known methods, by those skilled in the art.

DETAILED DESCRIPTION OF THE INVENTION

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety for all purposes.

Novel compounds encompassed by the instant invention include those described by the general formulas I and II set forth above, and the pharmaceutically acceptable salts, esters, prodrugs, solvates, hydrates or derivatives thereof.

As used herein a "pharmaceutically acceptable salt" includes salts that retain the biological effectiveness of the free acids and bases of the specified compound and that are not biologically or otherwise undesirable. A compound of this invention may possess acidic or basic groups and therefore may react with any of a number of inorganic or organic bases, and inorganic and organic acids, to form a pharmaceutically acceptable salt. Examples of pharmaceutically acceptable salts include those salts prepared by reaction of the compounds of this invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

As used herein, a "prodrug" is a compound that may be converted under physiological conditions or by solvolysis to the specified compound or to a pharmaceutically acceptable salt of such compound. By way of example only, prodrugs include, without limitation, compounds wherein an amino acid residue, or a polypeptide chain of two or more amino acid residues, is covalently joined through an amide or ester bond to a free amino, hydroxy, or carboxylic acid group of compounds of Formulas I and II. The amino acid residues contemplated include but are not limited to the naturally occurring amino acids. Other suitable amino acids include 4-hydroxyproline, hydroxylysine, demosine, isodemosine, 3-methyl histidine, norvaline, β-alanine, γ-aminobutyric acid, cirtulline, homocysteine, homoserine, ornithine and methionine sulfone. Additional types of prodrugs are well known in the art.

In some embodiments, the invention provides compounds, including pharmaceutically acceptable salts, prodrugs and solvates thereof having the formula I-A

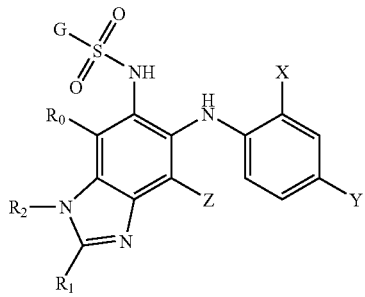

(I-A)

where G, X, Y, Z, $R_0$, $R_1$ and $R_2$ are defined as above.

In some embodiments, the invention provides compounds, including pharmaceutically acceptable salts, prodrugs and solvates thereof having the formula I-B

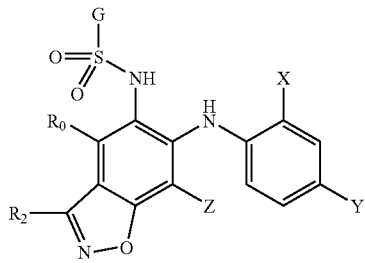

(I-B)

where G, $R_o$, $R_2$, X, Y and Z are as defined above.

In some embodiments, the invention provides compounds, including pharmaceutically acceptable salts, prodrugs and solvates thereof having the formula I-C

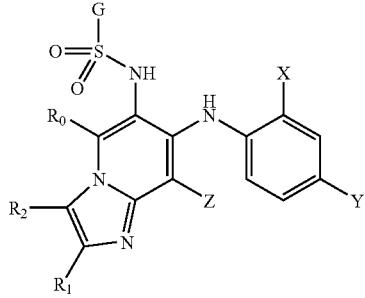

(I-C)

where G, $R_o$, $R_1$, $R_2$, X, Y and Z are as defined above.

In some embodiments, the invention provides compounds, including pharmaceutically acceptable salts, prodrugs and solvates thereof having the formula I-D

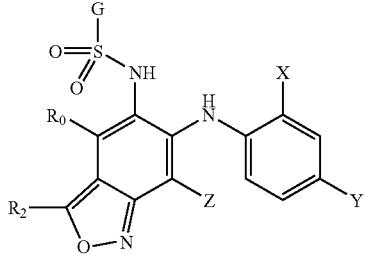

(I-D)

where G, $R_o$, $R_2$, X, Y and Z are as defined above.

In some embodiments, the invention provides compounds, including pharmaceutically acceptable salts, prodrugs and solvates thereof having the formula I-E.

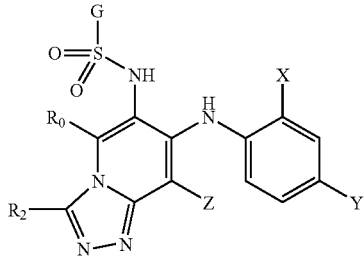
(I-E)

where G, $R_o$, $R_2$, X, Y and Z are as defined above.

In some embodiments, the invention provides compounds, including pharmaceutically acceptable salts, prodrugs and solvates thereof having the formula I-F.

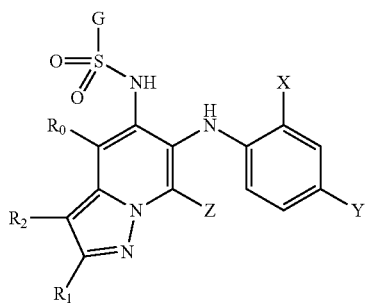
(I-F)

where G, $R_o$, $R_1$, $R_2$, X, Y and Z are as defined above.

In some embodiments, the invention provides compounds, including pharmaceutically acceptable salts, prodrugs and solvates thereof having the formula I-G.

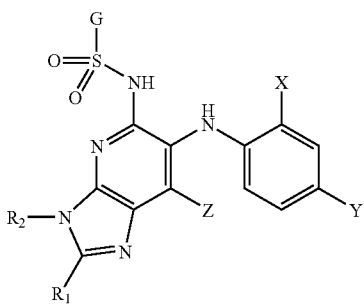
(I-G)

where G, $R_1$, $R_2$, X, Y and Z are as defined above.

In some embodiments, the invention provides compounds, including pharmaceutically acceptable salts, prodrugs and solvates thereof having the formula I-H.

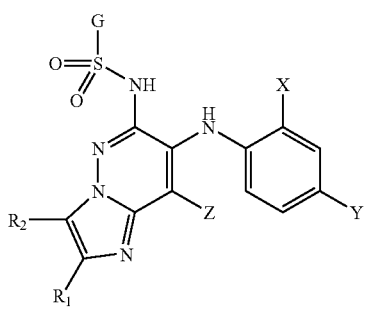
(I-H)

where G, $R_1$, $R_2$, X, Y and Z are as defined above.

In some embodiments, the invention provides compounds, including pharmaceutically acceptable salts, prodrugs and solvates thereof having the formula I-J

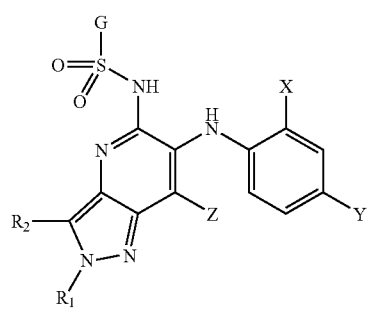
(I-J)

where G, $R_1$, $R_2$, X, Y and Z are as defined above.

In some embodiments, the invention provides compounds, including pharmaceutically acceptable salts, prodrugs and solvates thereof having the formula I-K

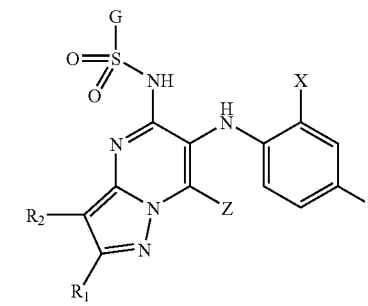
(I-K)

where G, $R_1$, $R_2$, X, Y and Z are as defined above.

In some embodiments, the invention provides compounds, including pharmaceutically acceptable salts, prodrugs and solvates thereof having the formula I-L

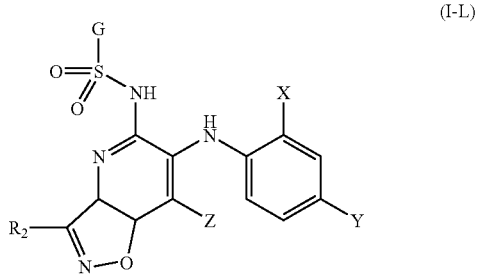

(I-L)

where G, $R_2$, X, Y and Z are as defined above.

In some embodiments, the invention provides a compound of formula I-A, I-B, I-C, I-D, I-E, I-F, I-G, I-H, I-J, I-K or I-L where G is $R_{1a}$, where $R_{1a}$ is defined as above. In some embodiments, this invention provides compounds of formulas I-A, I-B, I-C, I-D, I-E, I-F, I-G, I-H, I-J, I-K or I-L, where G is $R_{1a}$; X is F, Cl, or CH3; Y is I, Br, Cl, $CF_3$, or C1-C3 alkyl; and Z is H or F. In some embodiments, this invention provides compounds of formulas I-A, I-B, I-C, I-D, I-E, I-F, I-G, I-H, I-J, I-K or I-L, where G is $R_{1a}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)$OR_5$. In some embodiments, this invention provides compounds of formulas I-A, I-B, I-C, I-D, I-E, I-F, I-G, I-H, I-J, I-K or I-L, where G is $R_{1a}$; X is F, Cl, or CH3; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $R_{1a}$; X is F, Cl, or CH3; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy. In some embodiments, this invention provides a compound of formula I-A, I-B, I-C, I-D, I-E, I-F, I-G, I-H, I-J, I-K or I-L, where $R_{1a}$ is methyl, monohalomethyl, C1-C3 alkoxymethyl, or cyclopropoxymethyl.

In some embodiments, the invention provides a compound of formula I-A, I-B, I-C, I-D, I-E, I-F, I-G, I-H, I-J, I-K or I-L where G is $R_{1b}$, where $R_{1b}$ is defined as above. In some embodiments, this invention provides compounds of formulas I-A, I-B, I-C, I-D, I-E, I-F, I-G, I-H, I-J, I-K or I-L, where G is $R_{1b}$; X is F, Cl, or CH3; Y is I, Br, Cl, $CF_3$, or C1-C3 alkyl; and Z is H or F. In some embodiments, this invention provides compounds of formulas I-A, I-B, I-C, I-D, I-E, I-F, I-G, I-H, I-J, I-K or I-L, where G is $R_{1b}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)$OR_5$. In some embodiments, this invention provides compounds of formulas I-A, I-B, I-C, I-D, I-E, I-F, I-G, I-H, I-J, I-K or I-L, where G is $R_{1b}$; X is F, Cl, or CH3; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $R_{1b}$; X is F, Cl, or CH3; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy. In some embodiments of formula I-A, I-B, I-C, I-D, I-E, I-F, I-G, I-H, I-J, I-K or I-L, the invention provides compounds of formula I-A, I-B, I-C, I-D, I-E, I-F, I-G, I-H, I-J, I-K or I-L where $R_{1b}$ is isopropyl, 2-butyl, 2-pentyl, cyclopropyl, cyclobutyl, cyclopentyl, or cyclohexyl, all optionally substituted with 1 or 2 substituents selected independently from F, Cl, OH, and OCH3; Y is Br, I, methyl, or trifluoromethyl. In some embodiments of formula I-A, I-B, I-C, I-D, I-E, I-F, I-G, I-H, I-J, I-K or I-L, the invention provides compounds of formula I-A, I-B, I-C, I-D, I-E, I-F, I-G, I-H, I-J, I-K or I-L where R1b is isopropyl, 2-butyl, 2-pentyl, cyclopropyl, cyclobutyl, cyclopentyl, or cyclohexyl, all optionally substituted with one Cl, with one or with 1 or 2 OH groups; and Y is Br, I, methyl, or trifluoromethyl.

In some embodiments, the invention provides a compound of formula I-A, I-B, I-C, I-D, I-E, I-F, I-G, I-H, I-J, I-K or I-L where G is $R_{1c}$, where $R_{1c}$ is $(CH_2)_nO_mR'$, where m is 0 or 1, n is 2 or 3 when m is 1, and n is 1 or 2 when m is 0, and R' is C1-C6 alkyl, optionally substituted with 1-3 substituents selected independently from F, Cl, OH, $OCH_3$, $OCH_2CH_3$, and C3-C6 cycloalkyl. In some embodiments, this invention provides compounds of formulas I-A, I-B, I-C, I-D, I-E, I-F, I-G, I-H, I-J, I-K or I-L, where G is $R_{1c}$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $R_{1c}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)$OR_5$. In some embodiments, this invention provides compounds of formulas I-A, I-B, I-C, I-D, I-E, I-F, I-G, I-H, I-J, I-K or I-L, where G is $R_{1c}$; X is F, Cl, or CH3; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $R_{1c}$; X is F, Cl, or CH3; Y is I, Br, Cl, $CF_3$, or C1-C3 alkyl; is H or F; and $R_o$ is F, Cl, C1-C4 alkyl, C1-C3 alkoxy, trifluoromethoxy, or 2-methoxy-ethoxy. In some embodiments, this invention provides a compound of formula I-A, I-B, I-C, I-D, I-E, I-F, I-G, I-H, I-J, I-K or I-L, where G is $R_{1c}$, m is zero, n is 1 or 2, and R' is C1-C4 alkyl, optionally substituted as described above. In some embodiments, this invention provides a compound of formula I-A, I-B, I-C, I-D, I-E, I-F, I-G, I-H, I-J, I-K or I-L, where G is $R_{1c}$, m is 1, n is 2 or 3, and R' is C1-C4 alkyl, optionally substituted as described above. In some embodiments, this invention provides a compound of formula I-A, I-B, I-C, I-D, I-E, I-F, I-G, I-H, I-J, I-K or I-L, where m is zero, n is 1 or 2, and R' is C1-C4 alkyl, optionally substituted with 1-3 groups selected from OH, $OCH_3$, Cl, and cyclopropyl.

In some embodiments, the invention provides a compound of formula I-A, I-B, I-C, I-D, I-E, I-F, I-G, I-H, I-J, I-K or I-L where G is $R_{1d}$, where $R_{1d}$ is C(A')(A")(B)—where B, A', and A" are, independently, H or C1-4 alkyl, optionally substituted with one or two OH groups or halogen atoms, or A' and A", together with the carbon atom to which they are attached, form a 3- to 6-member saturated ring, said ring optionally containing one or two heteroatoms selected, independently, from O, N, and S and optionally substituted with one or two groups selected independently from methyl, ethyl, and halo. In some embodiments, this invention provides compounds of formulas I-A, I-B, I-C, I-D, I-E, I-F, I-G, I-H, I-J, I-K or I-L, where G is $R_{1d}$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $R_{1d}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, $O-C(=O)R_4$, or $C(=O)OR_5$. In some embodiments, this invention provides compounds of formulas I-A, I-B, I-C, I-D, I-E, I-F, I-G, I-H, I-J, I-K or I-L, where G is $R_{1d}$; X is F, Cl, or $CH_3$; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $R_{1d}$; X is F, Cl, or $CH_3$; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy.

In some embodiments, this invention provides a compound of formula I-A, I-B, I-C, I-D, I-E, I-F, I-G, I-H, I-J, I-K or I-L, where $R_{1d}$ is cycloalkyl or 1-alkyl-cycloalkyl, in which the 1-alkyl group is optionally substituted with one or two OH groups or with one or two halogen atoms. In some embodiments, this invention provides a compound of formula I-A, I-B, I-C, I-D, I-E, I-F, I-G, I-H, I-J, I-K or I-L, where $R_{1d}$ is tetrahydrofuryl, tetrahydrothienyl, pyrrolidyl, piperidyl, piperazinyl, or morpholyl, each optionally substituted as described above. In some embodiments, the invention provides a compound of formula I-A, I-B, I-C, I-D, I-E, I-F, I-G, I-H, I-J, I-K or I-L, in which R1d is 1-(monohydroxyalkyl)cycloalkyl. In some embodiments, the invention provides a compound of formula I-A, I-B, I-C, I-D, I-E, I-F, I-G, I-H, I-J, I-K or I-L, in which $R_{1d}$ is 1-(dihydroxyalkyl)cycloalkyl.

In some embodiments, the invention provides a compound of formula I-A, I-B, I-C, I-D, I-F, I-G, I-H, I-J, I-K or I-L, where G is $R_{1e}$, where $R_{1e}$ is defined above. In some embodiments, this invention provides compounds of formulas I-A, I-B, I-C, I-D, I-E, I-F, I-G, I-H, I-J, I-K or I-L, where G is $R_{1e}$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $R_{1e}$; X is F, Cl, or $CH_3$; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, $O-C(=O)R_4$, or $C(=O)OR_5$. In some embodiments, this invention provides compounds of formulas I-A, I-B, I-C, I-D, I-E, I-F, I-G, I-H, I-J, I-K or I-L, where G is $R_{1e}$; X is F, Cl, or $CH_3$; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $R_{1e}$; X is F, Cl, or $CH_3$; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy.

In some embodiments, the invention provides a compound of formula I-A, I-B, I-C, I-D, I-E, I-F, I-G, I-H, I-J, I-K or I-L, where G is $Ar_1$, where $Ar_1$ is defined as above. In some embodiments, this invention provides compounds of formulas I-A, where G is $Ar_1$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $Ar_1$; X is F, Cl, or $CH_3$; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, $O-C(=O)R_4$, or $C(=O)OR_5$. In some embodiments, this invention provides compounds of formulas I-A, I-B, I-C, I-D, I-E, I-F, I-G, I-H, I-J, I-K or I-L, where G is $Ar_1$; X is F, Cl, or $CH_3$; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $Ar_1$; X is F, Cl, or $CH_3$; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy. In some embodiments of formula I-A, I-B, I-C, I-D, I-E, I-F, I-G, I-H, I-J, I-K or I-L, this invention provides a compound of formula I-A, I-B, I-C, I-D, I-E, I-F, I-G, I-H, I-J, I-K or I-L, where G is $Ar_1$, where W is $CR_2$ and V is N. In some embodiments, this invention provides a compound of formula I-A, I-B, I-C, I-D, I-E, I-F, I-G, I-H, I-J, I-K or I-L, where G is $Ar_1$, in which W and V are both N. In some embodiments, this invention provides a compound of formula I-A, I-B, I-C, I-D, I-E, I-F, I-G, I-H, I-K or I-L where G is $Ar_1$, in which W is $CR_2$ and V is $CR_3$.

In some embodiments, this invention provides a compound of formula I-A, I-B, I-C, I-D, I-E, I-F, I-G, I-H, I-J, I-K or I-L, where G is $A_{r1}$ and $A_{r1}$ is phenyl or monosubstituted phenyl, $R_o$ is F, methyl, ethyl, C1-C3 alkoxy, trifluoromethoxy, or 2-methoxy-ethoxy; X is F, Cl, or $CH_3$; Y is I; and Z is F. In some embodiments, this invention provides a compound of formula I-A, I-B, I-C, I-D, I-E, I-F, I-G, I-H, I-J, I-K or I-L, where G is $A_{r1}$, where $A_{r1}$ is phenyl or monosubstituted phenyl, $R_o$ is halogen, C1-C6 alkyl, C3-C6 cycloalkyl, C2-C6 alkenyl, C2-C6 alkynyl, all such alkyl, cycloalkyl, alkenyl, and alkynyl groups optionally substituted with 1-3 substituents selected independently from halogen, OH, CN, cyanomethyl, nitro, phenyl, and trifluoromethyl; or $R_o$ is phenyl, $OR_3$, furyl, thienyl, thiazolyl, isothiazolyl, oxazolyl, isoxazolyl, pyrrolyl, or pyrazolyl.

In some embodiments, this invention provides a compound of formula I-A, I-B, I-C, I-D, I-E, I-F, I-G, I-H, I-J, I-K or I-L, where G is $A_{r1}$, where $A_{r1}$ is phenyl or monosubstituted phenyl, Ro is F, Cl, C1-C3 alkyl, C1-C3 alkoxy, 2-methoxy-ethoxy, C2-C3 alkenyl, C2-C3 alkynyl, trifluoromethyl, phenyl, furyl, or thienyl. thiazolyl, isothiazolyl, oxazolyl, isoxazolyl, pyrrolyl, or pyrazolyl; X is F, Cl, or methyl; Y is I, Br, Cl, $CF_3$, or C1-C3 alkyl; and Z is F. In some embodiments, this invention provides compound of formula I-A, I-B, I-C, I-D, I-E, I-F, I-G, I-H, I-J, I-K or I-L, where G is $A_{r1}$, where $A_{r1}$ is phenyl or monosubstituted phenyl, Ro is H; X is F, Cl, or CH3; Y is Br or I; and Z is F.

In some embodiments, the invention provides a compound of formula I-A, I-B, I-C, I-D, I-E, I-F, I-G, I-H, I-J, I-K or I-L where G is $Ar_2$, where $Ar_2$ is defined as above. In some embodiments, this invention provides compounds of formulas I-A, I-B, I-C, I-D, I-E, I-F, I-G, I-H, I-J, I-K or I-L, where G is $Ar_2$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $Ar_2$; X is F, Cl, or $CH_3$; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, $O-C(=O)R_4$, or $C(=O)OR_5$. In some embodiments, this invention provides compounds of formulas I-A, I-B, I-C, I-D, I-E, I-F, I-G, I-H, I-J, I-K or I-L, where G is $Ar_2$; X is F, Cl, or $CH_3$; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $Ar_2$; X is F, Cl, or $CH_3$; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy.

In some embodiments, this invention provides compounds of formula I-A, I-B, I-C, I-D, I-E, I-F, I-G, I-H, I-J, I-K or I-L, where G is $A_{r2}$, where $A_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen. In some embodiments, this invention provides compounds of formula I-A, I-B, I-C, I-D, I-E, I-F, I-G, I-H, I-J, I-K or I-L, where G is $A_{r2}$, where $A_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R_o$ is H, F, Cl, C1-C3 alkyl, monochord C1-C3 alkyl, C1-C3 alkoxy, trifluoromethoxy, methylmethoxy, or 2-methoxy-ethoxy; X is F, Cl, or CH3: Y is I, Br, Cl, CF3, or C1-C3 alkyl, and Z is H or F. In some embodiments, this invention provides compounds of formula I-A, I-B, I-C, I-D, I-E, I-F, I-G, I-H, I-J, I-K or I-L, where G is $A_{r2}$, where $A_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; Ro is H; X is F, Cl, or CH3: Y is I, Br, Cl, CF3, or C1-C3 alkyl, and Z is H or F. In some embodiments, this invention provides compounds of formula I-A, I-B, I-C, I-D, I-E, I-F, I-G, I-H, I-J, I-K or I-L, where G is $A_{r2}$, where $A_{r2}$ is thiazolyl, isothiazolyl, oxazolyl, isoxazolyl, pyrrolyl, or pyrazolyl, all optionally substituted with methoxycarbonyl, methylcarbamoyl, acetamido, acetyl, methyl, ethyl, trifluoromethyl, or halogen; Ro is H or methoxy; X is F, Cl, or CH3: Y is I, Br, Cl, CF3, or C1-C3 alkyl, and Z is H or F.

In some embodiments, the invention provides a compound of formula I-A, I-B, I-C, I-D, I-E, I-F, I-G, I-H, I-J, I-K or I-L, where G is $Ar_3$, where $Ar_3$ is defined above, In some embodiments, this invention provides compounds of formulas I-A, I-B, I-C, I-D, I-B, I-F, I-G, I-H, I-J, I-K or I-L, where G is $Ar_3$; X is F, Cl, or CH3; Y is I, Br, Cl, CF3, or C1-C3 alkyl; and Z is H or F. In some embodiments, this invention provides compounds of formulas I-A, I-B, I-C, I-D, I-E, I-F, I-G, I-H, I-J, I-K or I-L, where G is $Ar_3$; X is F, Cl, or $CH_3$; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)$OR_5$. In some embodiments, this invention provides compounds of formulas I-A, I-B, I-C, I-D, I-E, I-F, I-G, I-H, I-J, I-K or I-L, where G is $Ar_3$; X is F, Cl, or $CH_3$; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas I-A, I-B, I-C, I-D, I-E, I-F, I-G, I-H, I-J, I-K or I-L, where G is $Ar_3$; X is F, Cl, or $CH_3$; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy.

Compounds of formula I-M, I-N, I-O, I-P, I-Q, I-R, I-S, and I-T are exemplary compounds of formula

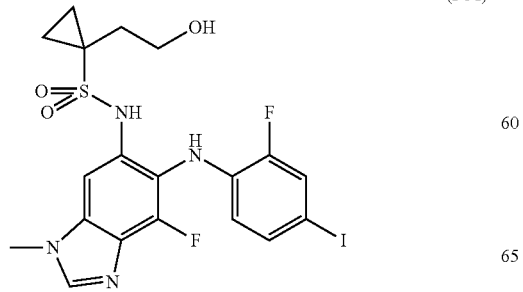

(I-M)

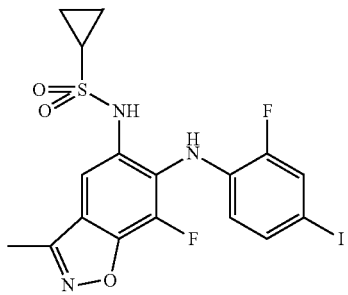

(I-N)

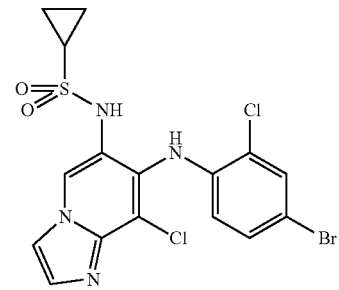

(I-O)

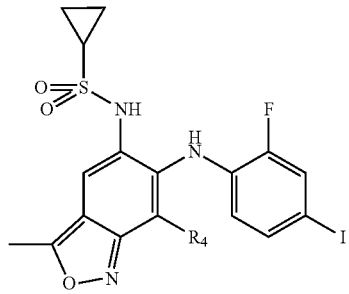

(I-P)

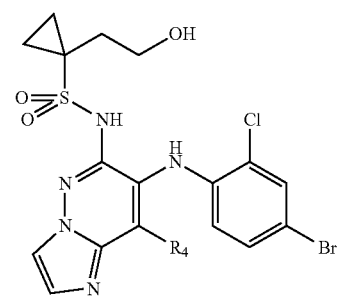

(I-Q)

(I-R)

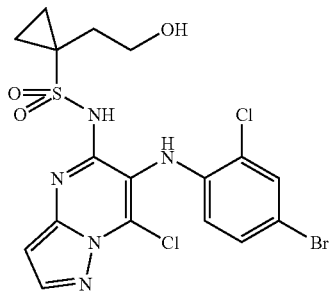 (I-S)

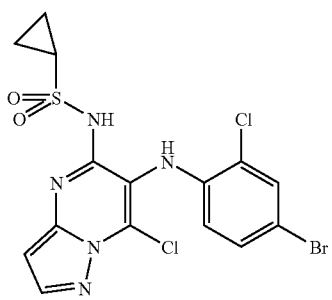 (I-T)

where $R_4$ is H, F, Cl, Br, I, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, and $R_{10}$ may also be nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazolyl, N-morpholinyl carbonylamino, N-morpholinylsulfonyl, or N-pyrrolidinylcarbonylamino In another aspect, the invention provides compounds of the general formula II as set forth above.

In some embodiments, the invention provides compounds, including pharmaceutically acceptable salts, prodrugs and solvates thereof having the formula II-A.

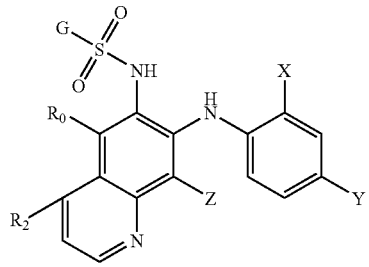 (II-A)

where G, $R_o$, $R_2$, X, Y and Z are as defined above.

In some embodiments, the invention provides compounds, including pharmaceutically acceptable salts, prodrugs and solvates thereof having the formula II-B.

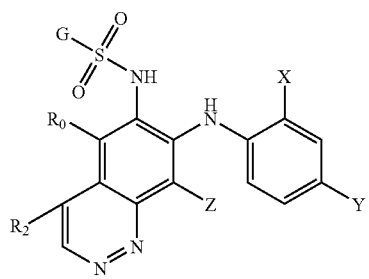 (II-B)

where G, $R_o$, $R_2$, X, Y and Z are as defined above.

In some embodiments, the invention provides compounds, including pharmaceutically acceptable salts, prodrugs and solvates thereof having the formula II-C.

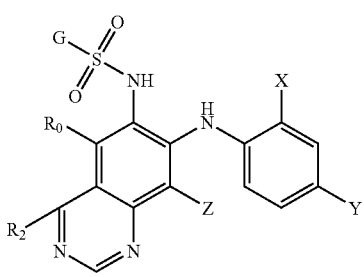 (II-C)

where G, $R_o$, $R_2$, X, Y and Z are as defined above.

In some embodiments, the invention provides a compound of formula II-A, II-B or II-C, where G is $R_{1a}$, where $R_{1a}$ is defined as above. In some embodiments, this invention provides compounds of formulas II-A, II-B or II-C, where G is $R_{1a}$; X is F, Cl, or CH3; Y is I, Br, Cl, $CF_3$, or C1-C3 alkyl; and Z is H or F. In some embodiments, this invention provides compounds of formulas II-A, II-B or II-C, where G is $R_{1a}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)$OR_5$. In some embodiments, this invention provides compounds of formulas II-A, II-B or II-C, where G is $R_{1a}$; X is F, Cl, or CH3; Y is I, Br, Cl, $CF_3$, or C1-C3 alkyl; Z is H or F; and $R_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is $R_{1a}$; X is F, Cl, or CH3; Y is I, Br, Cl, $CF_3$, or C1-C3 alkyl; Z is H or F; and $R_o$ is F, Cl, C1-C4 alkyl, C1-C3 alkoxy, trifluoromethoxy, or 2-methoxy-ethoxy. In some embodiments, this invention provides a compound of formula II-A, II-B or II-C, where $R_{1a}$ is methyl, monohalomethyl, C1-C3 alkoxymethyl, or cyclopropoxymethyl.

In some embodiments, the invention provides a compound of formula II-A, II-B or II-C, where G is $R_{1b}$, where $R_{1b}$ is defined as above. In some embodiments, this invention provides compounds of formulas II-A, II-B or II-C, where G is $R_{1b}$; X is F, Cl, or CH3; Y is I, Br, Cl, $CF_3$, or C1-C3 alkyl; and Z is H or F. In some embodiments, this invention provides compounds of formulas II-A, II-B or II-C, where G is $R_{1b}$; X is F, Cl, or CH3; Y is I, Br, Cl, $CF_3$, or C1-C3 alkyl; Z is H or F; and $R_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, $OR_3$, O—C(=O)$R_4$, or C(=O)

OR$_5$. In some embodiments, this invention provides compounds of formulas II-A, II-B or II-C, where G is R$_{1b}$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is R$_{1b}$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy. In some embodiments of formula II-A, II-B or II-C, the invention provides compounds of formula II-A, II-B or II-C, where R$_{1b}$ is isopropyl, 2-butyl, 2-pentyl, cyclopropyl, cyclobutyl, cyclopentyl, or cyclohexyl, all optionally substituted with 1 or 2 substituents selected independently from F, Cl, OH, and OCH3; Y is Br, I, methyl, or trifluoromethyl. In some embodiments of formula II-A, II-B or II-C, the invention provides compounds of formula II-A, II-B or II-C, where R$_{1b}$ is isopropyl, 2-butyl, 2-pentyl, cyclopropyl, cyclobutyl, cyclopentyl, or cyclohexyl, all optionally substituted with one Cl, with one or with 1 or 2 OH groups; and Y is Br, I, methyl, or trifluoromethyl.

In some embodiments, the invention provides a compound of formula II-A, II-B or II-C, where G is R$_{1c}$, where R$_{1c}$ is (CH$_2$)$_n$O$_m$R', where m is 0 or 1, n is 2 or 3 when m is 1, and n is 1 or 2 when m is 0, and R' is C1-C6 alkyl, optionally substituted with 1-3 substituents selected independently from F, Cl, OH, OCH$_3$, OCH$_2$CH$_3$, and C3-C6 cycloalkyl. In some embodiments, this invention provides compounds of formulas II-A, II-B or II-C, where G is R$_{1c}$; X is F, Cl, or CH3; Y is I, Br, Cl, CF3, or C1-C3 alkyl; and Z is H or F. In some embodiments, this invention provides compounds of formulas II-A, II-B or II-C, where G is R$_{1c}$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O)OR$_5$. In some embodiments, this invention provides compounds of formulas II-A, II-B or II-C, where G is R$_{1c}$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is R$_{1c}$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy. In some embodiments, this invention provides a compound of formula II-A, II-B or II-C, where G is R$_{1c}$, m is zero, n is 1 or 2, and R' is C1-C4 alkyl, optionally substituted as described above. In some embodiments, this invention provides a compound of formula II-A, II-B or II-C, where G is R$_{1c}$, m is 1, n is 2 or 3, and R' is C1-C4 alkyl, optionally substituted as described above. In some embodiments, this invention provides a compound of formula II-A, II-B or II-C, where m is zero, n is 1 or 2, and R' is C1-C4 alkyl, optionally substituted with 1-3 groups selected from OH, OCH$_3$, Cl, and cyclopropyl.

In some embodiments, the invention provides a compound of formula II-A, II-B or II-C, where G is R$_{1d}$, where R$_{1d}$ is C(A')(A")(B)— where B, A', and A" are, independently, H or C1-4 alkyl, optionally substituted with one or two OH groups or halogen atoms, or A' and A", together with the carbon atom to which they are attached, form a 3- to 6-member saturated ring, said ring optionally containing one or two heteroatoms selected, independently, from O, N, and S and optionally substituted with one or two groups selected independently from methyl, ethyl, and halo. In some embodiments, this invention provides compounds of formulas II-A, II-B or II-C, where G is R$_{1d}$; X is F, Cl, or CH3; Y is I, Br, Cl, CF3, or C1-C3 alkyl; and Z is H or F. In some embodiments, this invention provides compounds of formulas II-A, II-B or II-C, where G is R$_{1d}$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O)OR$_5$. In some embodiments, this invention provides compounds of formulas II-A, II-B or II-C, where G is R$_{1d}$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is R$_{1d}$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy.

In some embodiments, this invention provides a compound of formula II-A, II-B or II-C, where R$_{1d}$ is cycloalkyl or 1-alkyl-cycloalkyl, in which the 1-alkyl group is optionally substituted with one or two OH groups or with one or two halogen atoms. In some embodiments, this invention provides a compound of formula II-A, II-B or II-C, where R$_{1d}$ is tetrahydrofuryl, tetrahydrothienyl, pyrrolidyl, piperidyl, piperazinyl, or morpholyl, each optionally substituted as described above. In some embodiments, the invention provides a compound of formula II-A, II-B or II-C, in which R1d is 1-(monohydroxyalkyl)cycloalkyl. In some embodiments, the invention provides a compound of formula II-A, II-B or II-C, in which R$_{1d}$ is 1-(dihydroxyalkyl)cycloalkyl.

In some embodiments, the invention provides a compound of formula II-A, II-B or II-C, where G is R$_{1e}$, where R$_{1e}$ is defined above. In some embodiments, this invention provides compounds of formulas II-A, II-B or II-C, where G is R$_{1e}$; X is F, Cl, or CH3; Y is I, Br, Cl, CF3, or C1-C3 alkyl; and Z is H or F. In some embodiments, this invention provides compounds of formulas II-A, II-B or II-C, where G is R$_{1e}$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O)OR$_5$. In some embodiments, this invention provides compounds of formulas II-A, II-B or II-C, where G is R$_{1e}$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is R$_{1e}$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy.

In some embodiments, the invention provides a compound of formula II-A, II-B or II-C, where G is Ar$_1$, where Ar$_1$ is defined as above. In some embodiments, this invention provides compounds of formulas II-A, II-B or II-C, where G is Ar$_1$; X is F, Cl, or CH3; Y is I, Br, Cl, CF3, or C1-C3 alkyl; and Z is H or F. In some embodiments, this invention provides compounds of formulas II-A, II-B or II-C, where G is Ar$_1$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O)OR$_5$. In some embodiments, this invention provides compounds of formulas II-A, II-B or II-C, where G is Ar$_1$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is Ar$_1$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy. In some embodiments of formula II-A, II-B or II-C, this invention provides a compound of formula II-A, II-B or II-C, where G is Ar$_1$, where W is CR$_2$ and V is N. In some embodiments, this invention provides a compound of formula II-A, II-B or II-C, where G is Ar$_1$, in which W and V are both. N. In some embodiments, this invention provides a compound of formula II-A, II-B or II-C, where G is Ar$_1$, in which U is CR$_2$ and V is CR$_3$.

In some embodiments, this invention provides a compound of formula II-A, II-B or II-C, where G is A$_{r1}$ and A$_{r1}$ is phenyl or monosubstituted phenyl, R$_o$ is F, methyl, ethyl, C1-C3 alkoxy, trifluoromethoxy, or 2-methoxy-ethoxy; X is F, Cl, or CH$_3$; Y is I; and Z is F. In some embodiments, this invention provides a compound of formula II-A, II-B or II-C, where G is A$_{r1}$, where A$_{r1}$ is phenyl or monosubstituted phenyl, R$_o$ is halogen, C1-C6 alkyl, C3-C6 cycloalkyl, C2-C6 alkenyl, C2-C6 alkynyl, all such alkyl, cycloalkyl, alkenyl, and alkynyl groups optionally substituted with 1-3 substituents selected independently from halogen, OH, CN, cyanomethyl, nitro, phenyl, and trifluoromethyl; or R$_o$ is phenyl, OR$_3$, furyl, thienyl, thiazolyl, isothiazolyl, oxazolyl, isoxazolyl, pyrrolyl, or pyrazolyl.

In some embodiments, this invention provides a compound of formula II-A, II-B or II-C, where G is A$_{r1}$, where A$_{r1}$ is phenyl or monosubstituted phenyl, Ro is F, Cl, C1-C3 alkyl, C1-C3 alkoxy, 2-methoxyethoxy, C2-C3 alkenyl, C2-C3 alkynyl, trifluoromethyl, phenyl, furyl, or thienyl. thiazolyl, isothiazolyl, oxazolyl, isoxazolyl, pyrrolyl, or pyrazolyl; X is F, Cl, or methyl; Y is I, Br, Cl, CF$_3$, or C1-C3 alkyl; and Z is F. In some embodiments, this invention provides compound of formula II-A, II-B or II-C, where G is A$_{r1}$, where A$_{r1}$ is phenyl or monosubstituted phenyl, Ro is H; X is F, Cl, or CH$_3$; Y is Br or I; and Z is F.

In some embodiments, the invention provides a compound of formula II-A, II-B or II-C, where G is Ar$_2$, where Ar$_2$ is defined as above. In some embodiments, this invention provides compounds of formulas II-A, II-B or II-C, where G is Ar$_2$; X is F, Cl, or CH$_3$; Y is I, Br, Cl, CF$_3$, or C1-C3 alkyl; and Z is H or F. In some embodiments, this invention provides compounds of formulas II-A, II-B or II-C, where G is Ar$_2$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O) OR$_5$. In some embodiments, this invention provides compounds of formulas II-A, II-B or II-C, where G is Ar$_2$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is Ar$_2$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy.

In some embodiments, this invention provides compounds of formula II-A, II-B or II-C, where G is A$_{r2}$, where A$_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen. In some embodiments, this invention provides compounds of formula II-A, II-B or II-C, where G is A$_{r2}$, where A$_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; R$_o$ is H, F, Cl, C1-C3 alkyl, monochloro C1-C3 alkyl, C1-C3 alkoxy, trifluoromethoxy, methyloxy-methoxy, or 2-methoxy-ethoxy; X is F, Cl, or CH3: Y is I, Br, Cl, CF$_3$, or C1-C3 alkyl, and Z is H or F. In some embodiments, this invention provides compounds of formula II-A, II-B or II-C, where G is A$_{r2}$, where A$_{r2}$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; Ro is H; X is F, Cl, or CH3: Y is I, Br, Cl, CF3, or C1-C3 alkyl, and Z is H or F. In some embodiments, this invention provides compounds of formula II-A, II-B or II-C, where G is A$_{r2}$, where A$_{r2}$ is thiazolyl, isothiazolyl, oxazolyl, isoxazolyl, pyrrolyl, or pyrazolyl, all optionally substituted with methoxycarbonyl, methylcarbamoyl, acetamido, acetyl, methyl, ethyl, trifluoromethyl, or halogen; Ro is H or methoxy; X is F, Cl, or CH3: Y is I, Br, Cl, CF$_3$, or C1-C3 alkyl, and Z is H or F.

In some embodiments, the invention provides a compound of formula II-A, II-B or II-C, where G is Ar$_3$, where Ar$_3$ is defined above. In some embodiments, this invention provides compounds of formulas II-A, II-B or II-C, where G is Ar$_3$; X is F, Cl, or CH3; Y is I, Br, Cl, CF3, or C1-C3 alkyl; and Z is H or F. In some embodiments, this invention provides compounds of formulas II-A, II-B or II-C, where G is Ar$_3$; X is F, Cl, or CH$_3$; Y is I, Br, Cl, CF$_3$, or C1-C3 alkyl; Z is H or F; and R$_o$ is H, halogen, C1-C6 alkyl, monohalo C1-C6 alkyl, C3-C6 cycloalkyl, C2-C6 alkenyl, C2-C6 alkynyl, phenyl, monosubstituted phenyl, OR$_3$, O—C(=O)R$_4$, or C(=O)OR$_5$. In some embodiments, this invention provides compounds of formulas II-A, II-B or II-C, where G is Ar$_3$; X is F, Cl, or CH$_3$; Y is I, Br, Cl, CF$_3$, or C1-C3 alkyl; Z is H or F; and R$_o$ is furyl, thienyl, thiazolyl, isothiazolyl, oxazolyl, isoxazolyl, pyrrolyl, or pyrazolyl. In some embodiments, this invention provides compounds of formulas II-A, II-B or II-C, where G is Ar$_3$; X is F, Cl, or CH$_3$; Y is I, Br, Cl, CF$_3$, or C1-C3 alkyl; Z is H or F; and R$_o$ is F, Cl, C1-C4 alkyl, C1-C3 alkoxy, trifluoromethoxy, or 2-methoxy-ethoxy.

Compounds of Formula II-B and II-F are Exemplary Compounds of Formula II

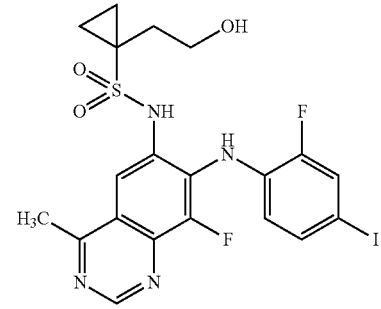

(II-E)

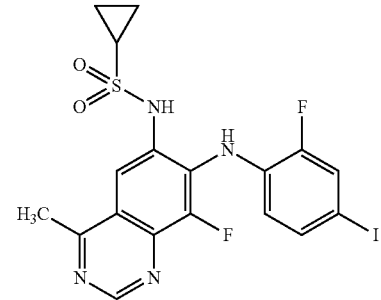

(II-F)

Certain compounds of the present invention may have asymmetric centers and therefore exist in different enantiomeric forms. All optical isomers and stereoisomers of the compounds of the present invention, and mixtures thereof, are considered to be within the scope of the invention. With respect to the compounds of the present invention, the invention includes the use of a racemate, one or more enantiomeric forms, one or more diastereomeric forms, or mixtures thereof. The compounds of the present invention may also exist as tautomers. This invention relates to the use of all such tautomers and mixtures thereof. The compounds of the present invention may also exist in different polymorphic states. This invention relates to the use of all such polymorphic states and mixtures thereof.

The subject invention also includes isotopically-labeled compounds, which are identical to those recited in the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, pharmaceutically acceptable salt, ester, prodrug, solvate, hydrate or derivative thereof which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays.

Tritiated, i.e., $^{3}H$ and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compound of the present invention, pharmaceutically acceptable salt, ester, prodrug, solvate, hydrate or derivative thereof can generally be prepared by carrying out procedures disclosed in the Schemes and/or in the Examples and Preparations below, by substituting a readily available isotopically labeled reagent for a non-isotopically labeled reagent.

This invention also encompasses prodrugs of compounds described herein and methods of treating disorders. For example, the invention provides for methods of treating proliferative disorders, or abnormal cell growth, by administering prodrugs of compounds of the present invention. The prodrugs of compounds of the invention can be administered as pharmaceutical compositions. Compounds of the present invention having free amino, amido, hydroxy or carboxylic groups can be converted into prodrugs.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The invention also relates to pharmaceutical compositions. In some embodiments the invention provides pharmaceutical compositions for the treatment of disorders such as hyperproliferative disorder in a mammal. In some embodiment, the treatment of said disorders comprises a therapeutically effective amount of a compound of the present invention, or a pharmaceutically acceptable salt, ester, prodrug, solvate, hydrate or derivative thereof, and a pharmaceutically acceptable carrier. In some embodiments, said pharmaceutical composition is for the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) or pain in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to a pharmaceutical composition for the prevention of blastocyte implantation in a mammal which comprises a therapeutically effective amount of a compound of the present invention, or a pharmaceutically acceptable salt, ester, prodrug, solvate, hydrate or derivative thereof, and a pharmaceutically acceptable carrier.

The invention also relates to a pharmaceutical composition for treating a disease related to vasculogenesis or angiogenesis in a mammal which comprises a therapeutically effective amount of a compound of the present invention, or a pharmaceutically acceptable salt, ester, prodrug, solvate, hydrate or derivative thereof, and a pharmaceutically acceptable carrier.

In some embodiments, said pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, ester, prodrug, solvate, hydrate or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease or pain in a mammal that comprises administering to said mammal a therapeutically effective amount of a compound of the present invention, or a pharmaceutically acceptable salt, ester, prodrug, solvate, hydrate or derivative thereof.

The invention also relates to a method of preventing blastocyte implantation in a mammal that comprises administering to said mammal a therapeutically effective amount of a compound of the present invention, or a pharmaceutically acceptable salt, ester, prodrug, solvate, hydrate or derivative thereof.

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer The invention further provides methods of modulating MEK activity by contacting MEK with an amount of a compound of the invention sufficient to modulate the activity of MEK. Modulate can be inhibiting or activating MEK activity. In some embodiments, the invention provides methods of inhibiting MEK activity by contacting MEK with an amount of a compound of the invention sufficient to inhibit the activity of MEK. In some embodiments, the invention provides methods of inhibiting MEK activity in a solution by contacting said solution with an amount of a compound of the invention sufficient to inhibit the activity of MEK in said solution. In some embodiments, the invention provides methods of inhibiting MEK activity in a cell by contacting said cell with an amount of a compound of the invention sufficient to inhibit the activity of MEK in said cell. In some embodiments, the invention provides methods of inhibiting MEK activity in a tissue by contacting said tissue with an amount of a compound of the invention sufficient to inhibit the activity of MEK in said tissue. In some embodiments, the invention provides methods of inhibiting MEK activity in an organism by contacting said organism with an amount of a compound of the invention sufficient to inhibit the activity of MEK in said organism. In some embodiments, the invention provides methods of inhibiting MEK activity in an animal by contacting said animal with an amount of a compound of the invention sufficient to inhibit the activity of MEK in said animal. In some embodiments, the invention provides methods of inhibiting MEK activity in a mammal by contacting said mammal with an amount of a compound of the invention sufficient to inhibit the activity of MEK in said mammal. In some embodiments, the invention provides methods of inhibiting MEK activity in a human by contacting said human with an amount of a compound of the invention sufficient to inhibit the activity of MEK in said human.

This invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of a chemotherapeutic, wherein the amounts of the compound, salt, ester, prodrug, solvate, hydrate or derivative, and of the chemotherapeutic are together effective in inhibiting abnormal cell growth. Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt, ester, prodrug, solvate, hydrate or derivative thereof, in combination with radiation therapy, wherein the amounts of the compound, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Without be limiting to any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The invention also relates to a method of and to a pharmaceutical composition of inhibiting abnormal cell growth in a mammal which comprises an amount of a compound of the present invention, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

In some embodiments the compounds of the invention will be co-administer with other agents as described above. The term "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present. Thus, in some embodiments, the compounds of the invention and the other agent(s) are administered in a single composition. In some embodiments, compounds of the invention and the other agent(s) are admixed in the composition.

Synthetic Procedures

In another aspect, the invention provides methods for synthesizing the compounds described herein. In some embodiments, the compounds of this invention can be prepared by the methods described below. The procedures below are intended to illustrate those methods, and the examples given are intended to illustrate the scope of this invention. Neither the methods not the examples should be construed as limiting the invention in any way. The procedures below are explained in more detail in the examples section.

Included in the methods of synthesis of the invention is the preparation of compound of formula 1-17 (as labeled in scheme 1). Scheme 1 is outlined below:

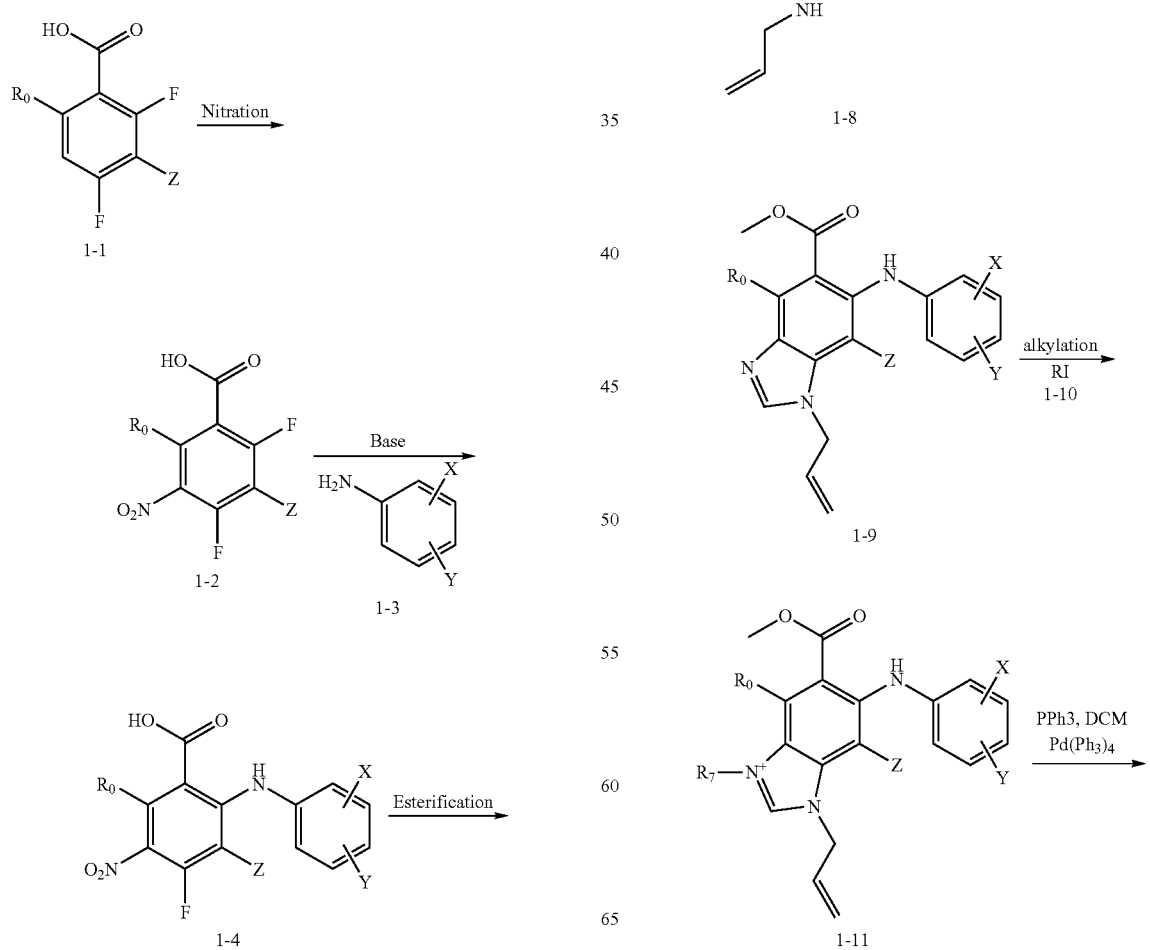

-continued

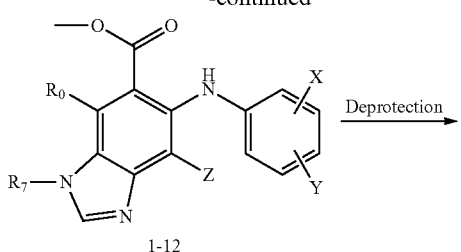
1-12

Deprotection →

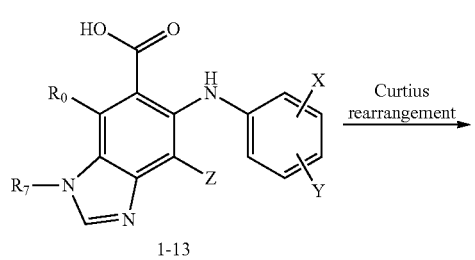
1-13

Curtius rearrangement →

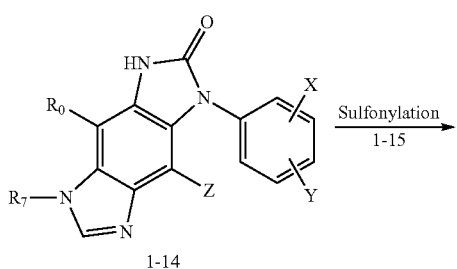
1-14

Sulfonylation 1-15 →

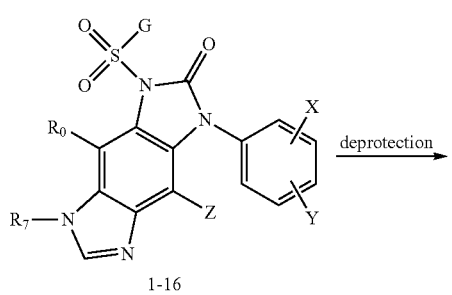
1-16 deprotection →

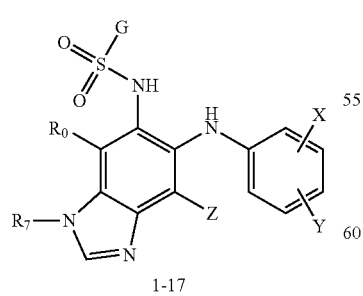
1-17

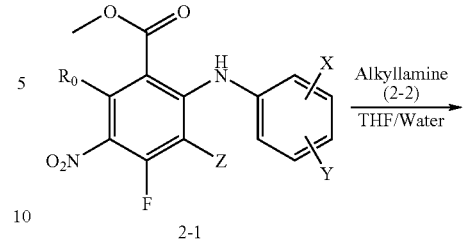
2-1

Alkyllamine (2-2) THF/Water →

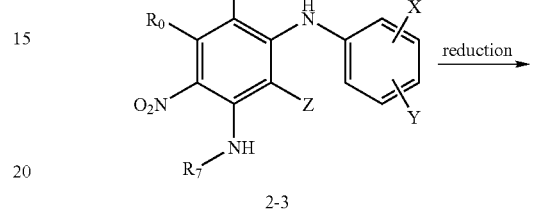
2-3 reduction →

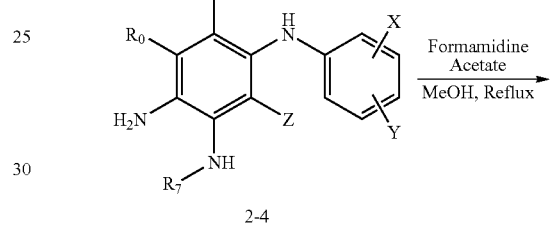
2-4

Formamidine Acetate MeOH, Reflux →

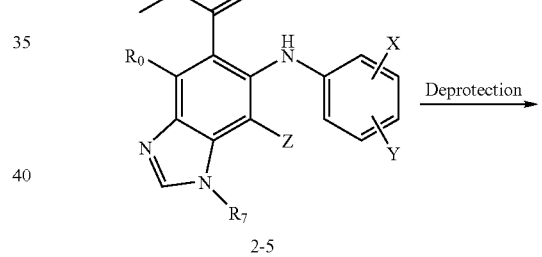
2-5

Deprotection →

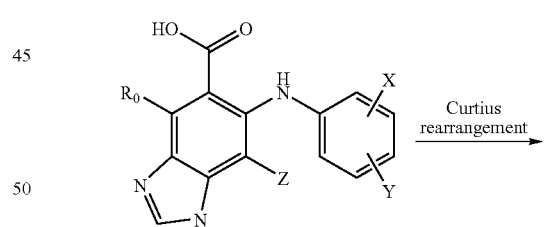
2-6

Curtius rearrangement →

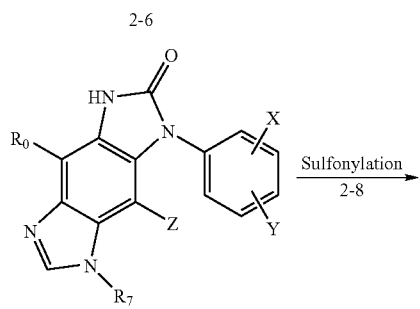
2-7

Sulfonylation 2-8 →

Included in the methods of synthesis of the invention is the preparation of compounds of general formula 2-14 (as labeled in scheme 2). Scheme 2 is outlined below:

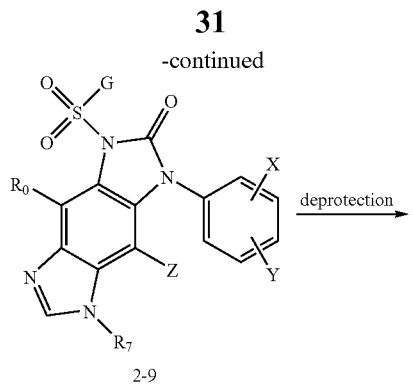
Included in the methods of synthesis of the invention is the preparation of compounds of general formula 3-13 (as labeled in scheme 3). Scheme 3 is outlined below:
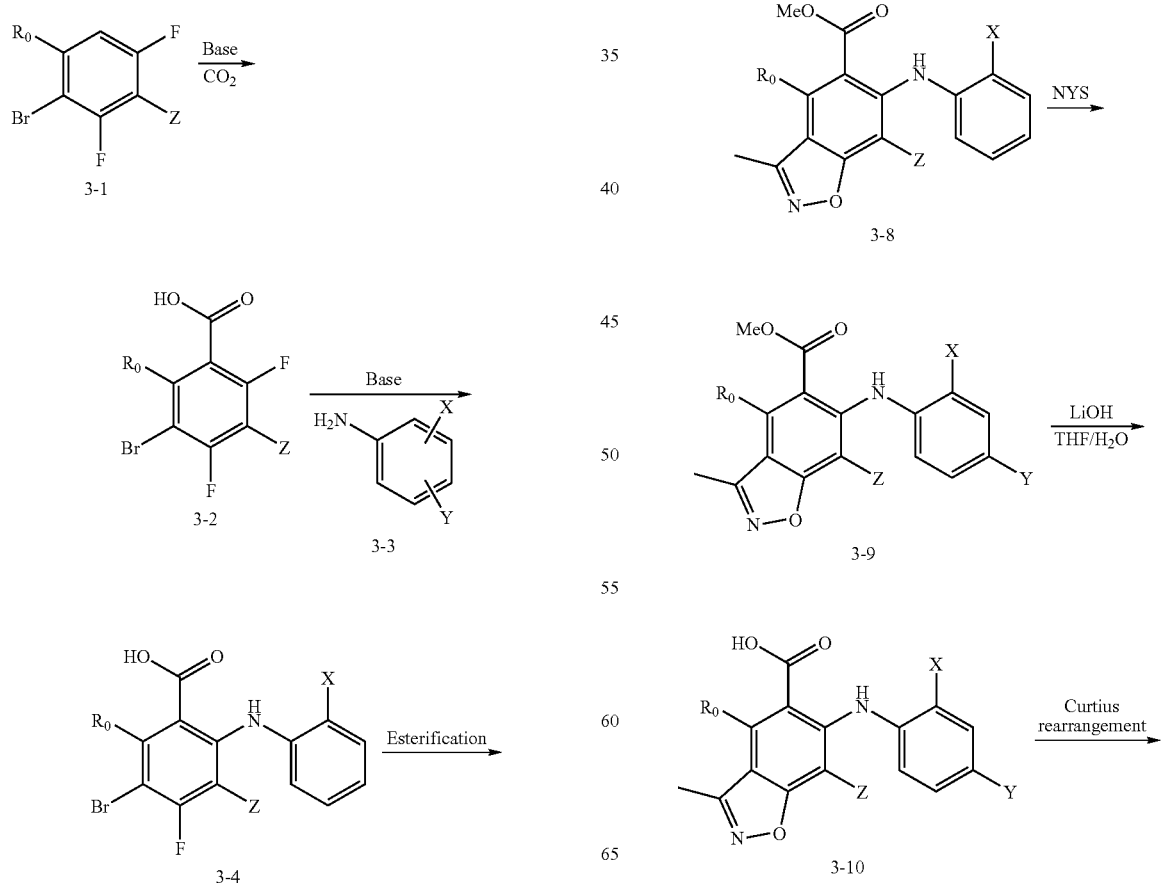
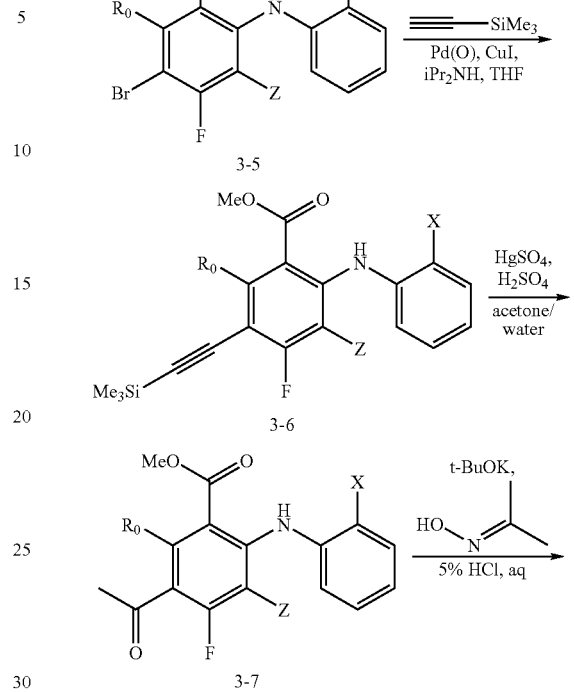

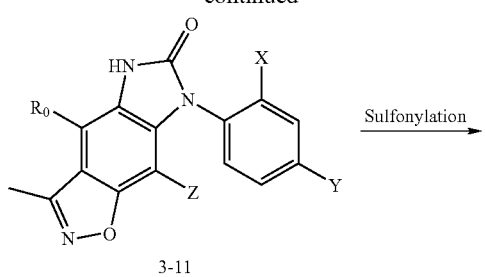
3-11
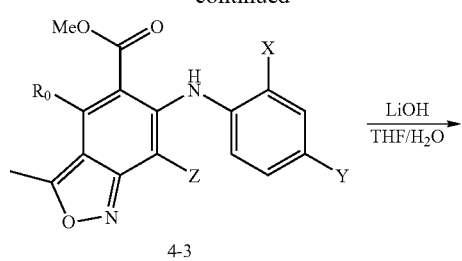
4-3
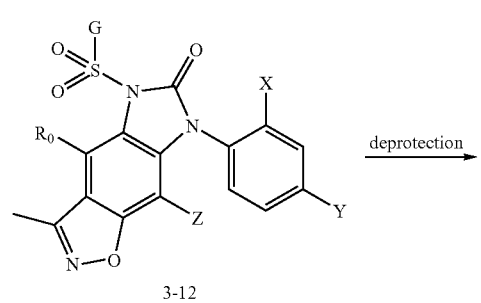
3-12
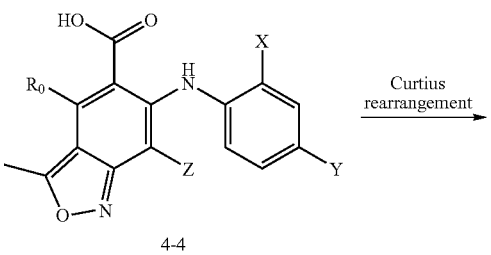
4-4
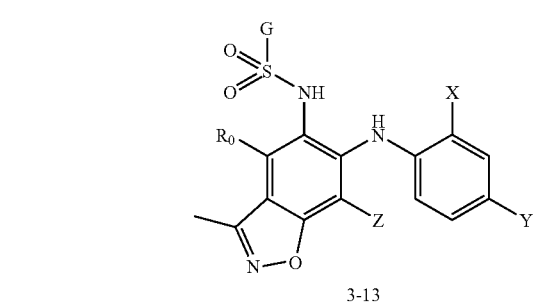
3-13
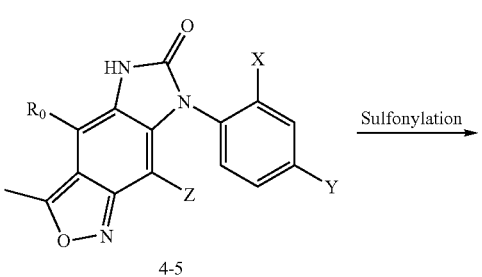
4-5
Included in the methods of synthesis of the invention is the preparation of compounds of general formula 4-7 (as labeled in scheme 4). Scheme 4 is outlined below:
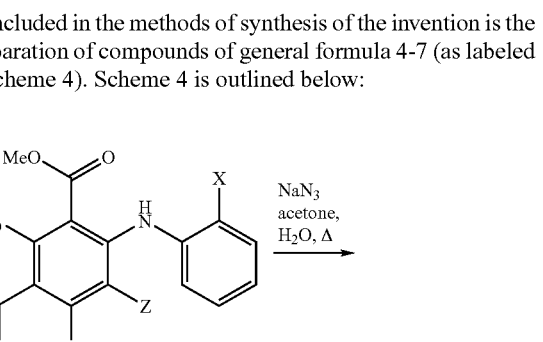
4-1
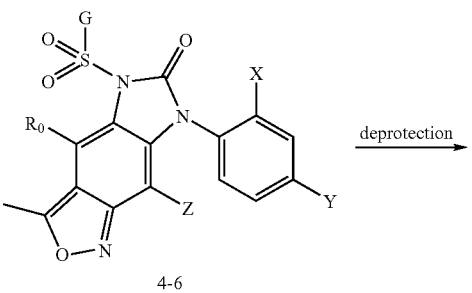
4-6
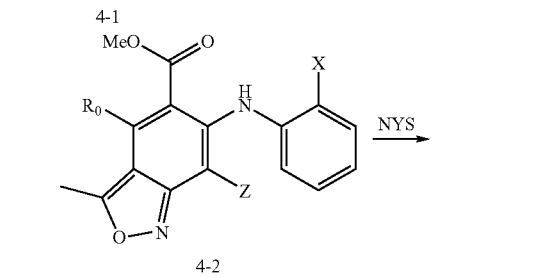
4-2
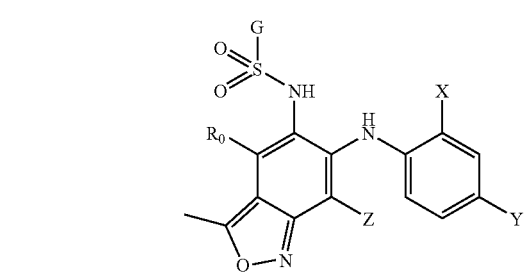
4-7
Included in the methods of synthesis of the invention is the preparation of compounds of general formula 5-14 (as labeled in scheme 5). Scheme 5 is outlined below:

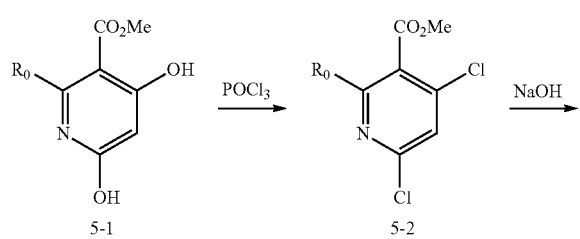
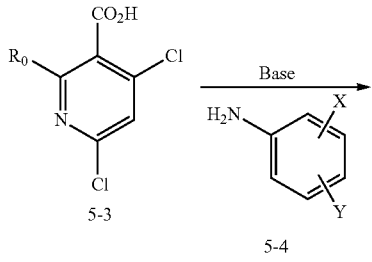
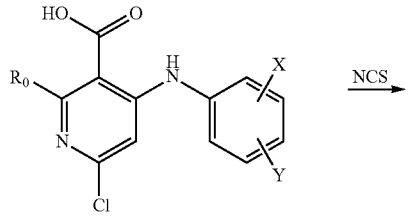
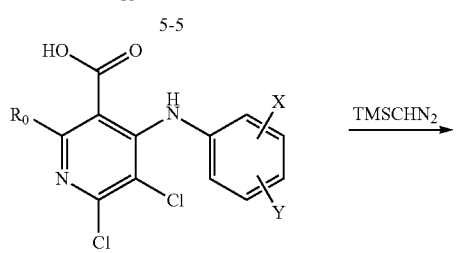
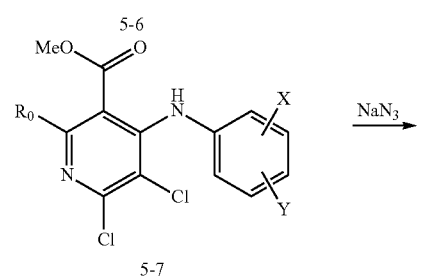
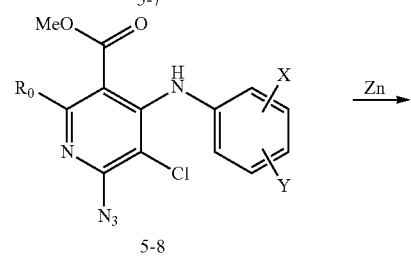
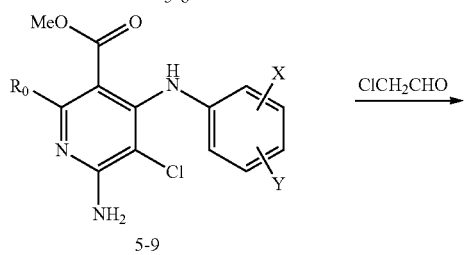
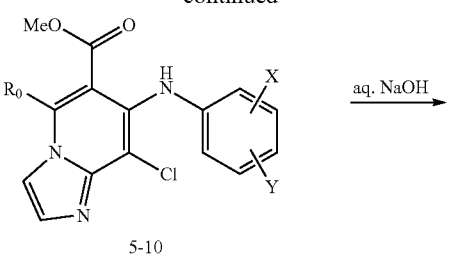
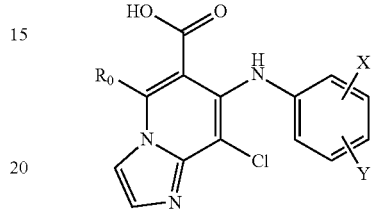
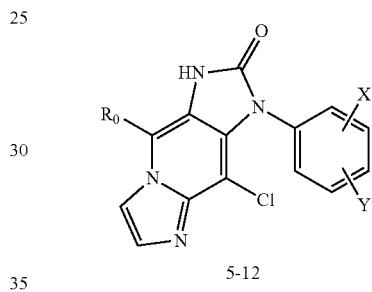
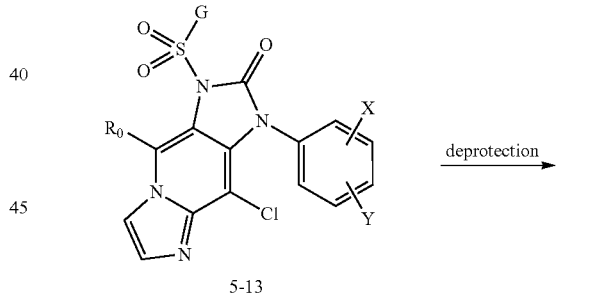
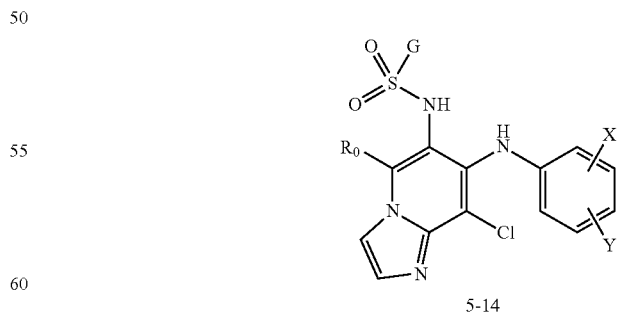
Included in the methods of synthesis of the invention is the preparation of compounds of general formula 6-9 (as labeled in scheme 6). Scheme 6 is outlined below:

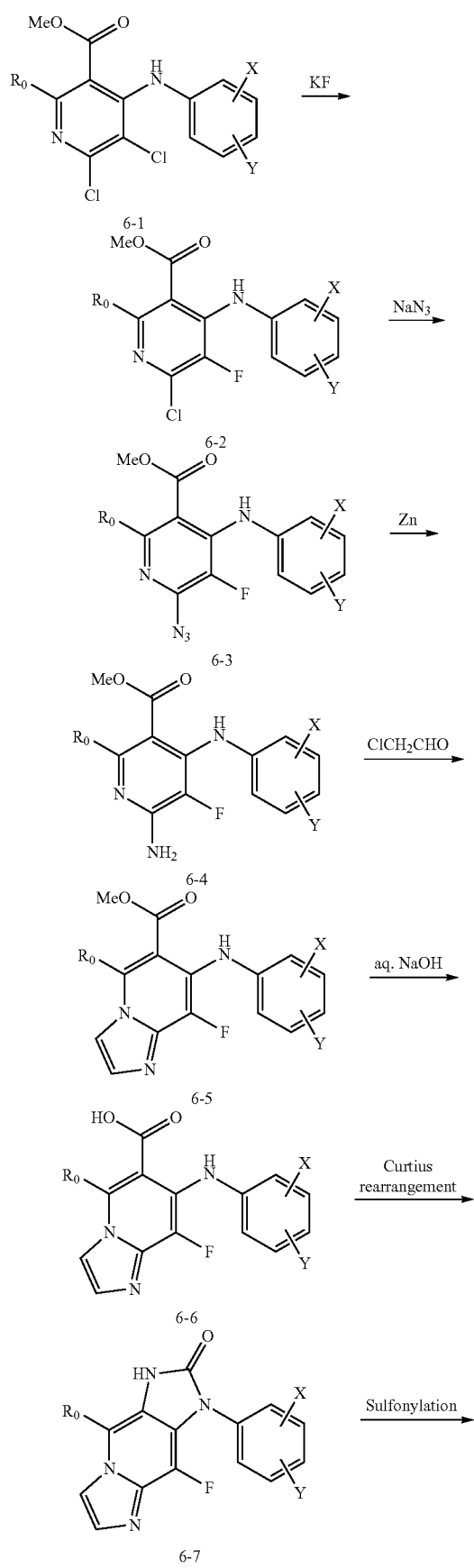
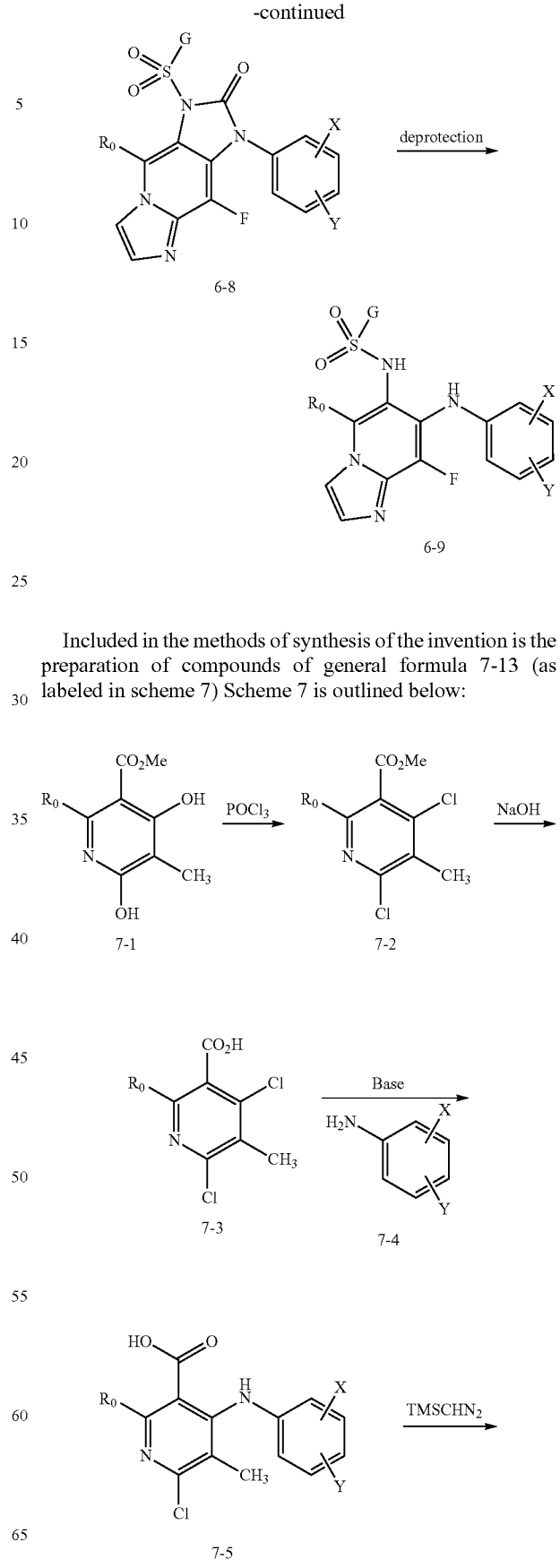
Included in the methods of synthesis of the invention is the preparation of compounds of general formula 7-13 (as labeled in scheme 7) Scheme 7 is outlined below:

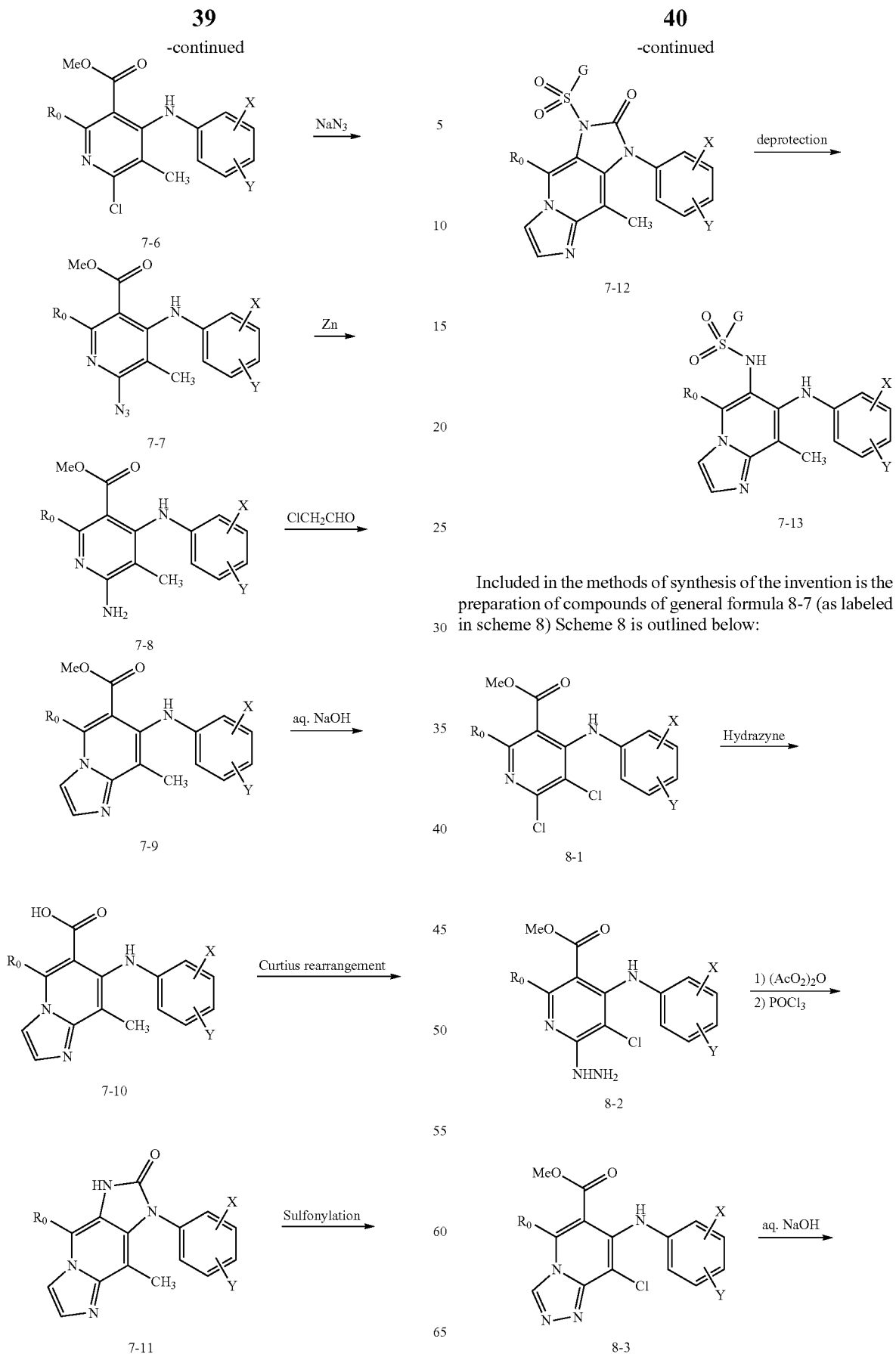
Included in the methods of synthesis of the invention is the preparation of compounds of general formula 8-7 (as labeled in scheme 8) Scheme 8 is outlined below:

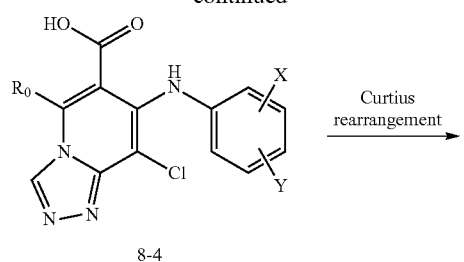
8-4
Curtius rearrangement →
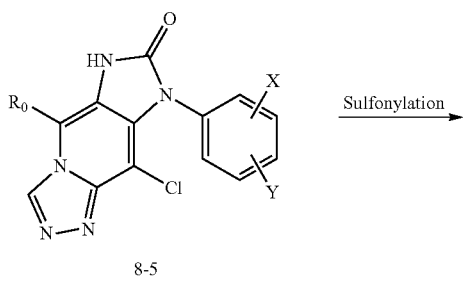
8-5
Sulfonylation →
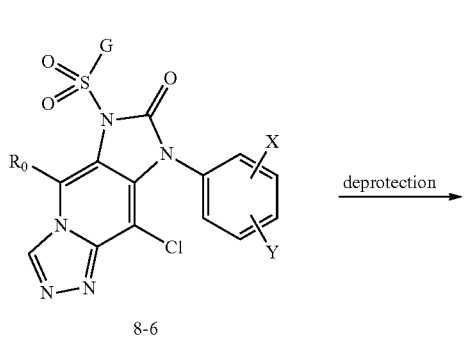
8-6
deprotection →
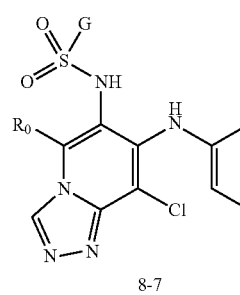
8-7
Included in the methods of synthesis of the invention is the preparation of compounds of general formula 9-7 (as labeled in scheme 9) Scheme 9 is outlined below:
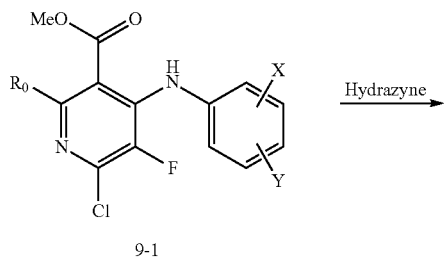
9-1
Hydrazyne →
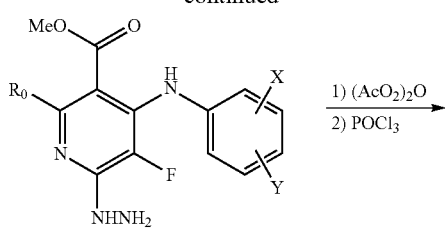
9-2
1) (AcO₂)₂O
2) POCl₃
→
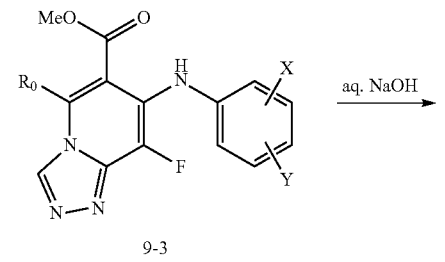
9-3
aq. NaOH →
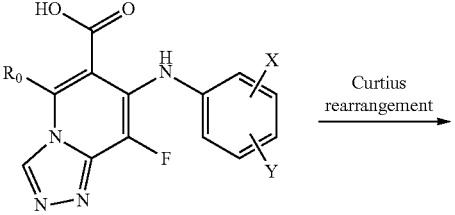
9-4
Curtius rearrangement →
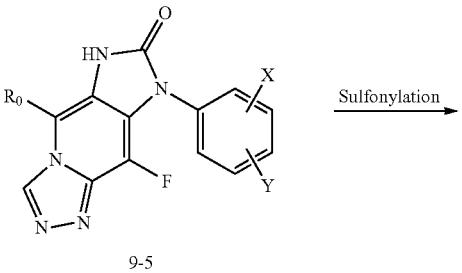
9-5
Sulfonylation →
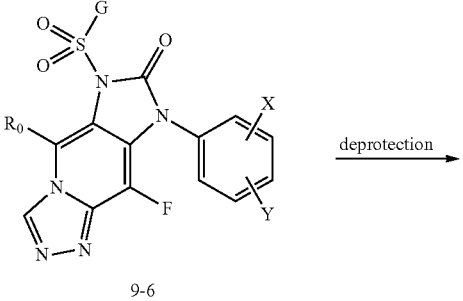
9-6
deprotection →
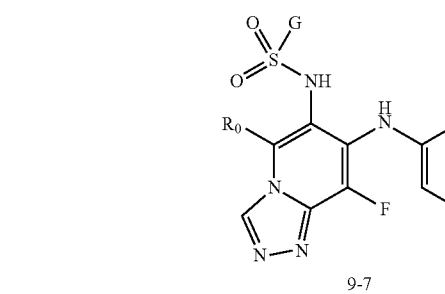
9-7

Included in the methods of synthesis of the invention is the preparation of compounds of general formula 10-7 (as labeled in scheme 10). Scheme 10 is outlined below:
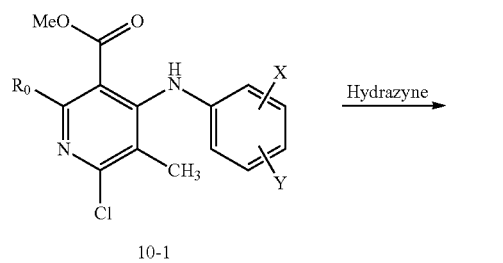
10-1
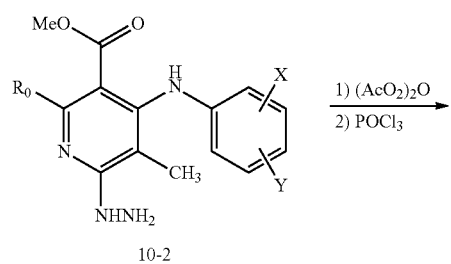
10-2
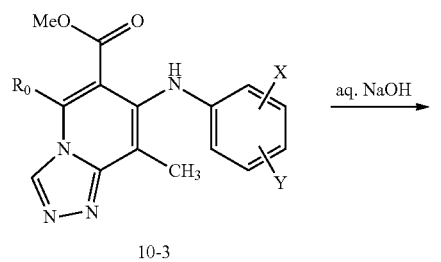
10-3
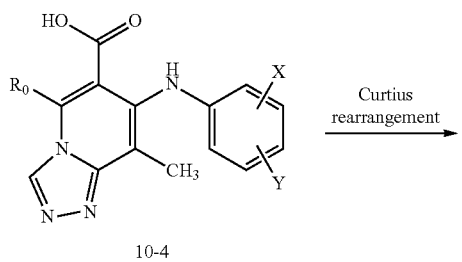
10-4
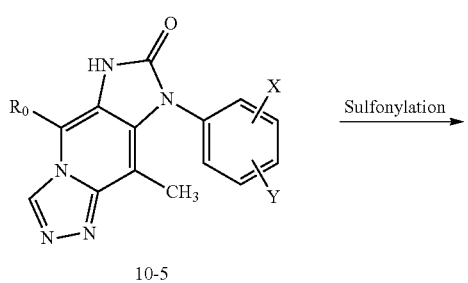
10-5
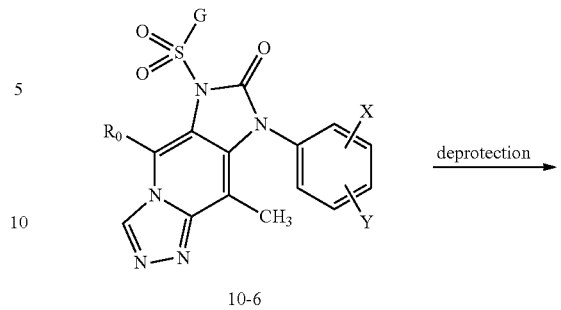
10-6
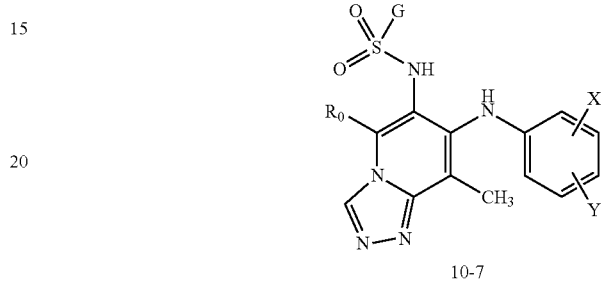
10-7
Included in the methods of synthesis of the invention is the preparation of compounds of general formula 11-14 (as labeled in scheme 11). Scheme 11 is outlined below:
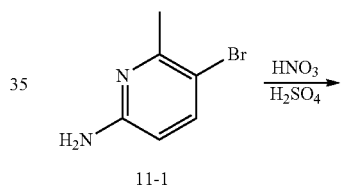
11-1
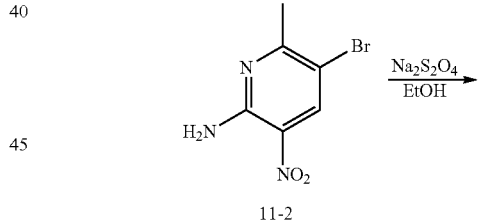
11-2
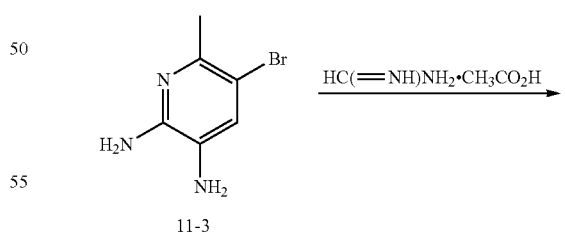
11-3
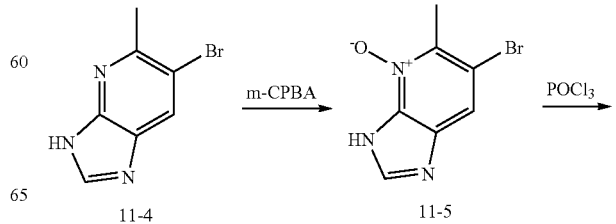
11-4    11-5

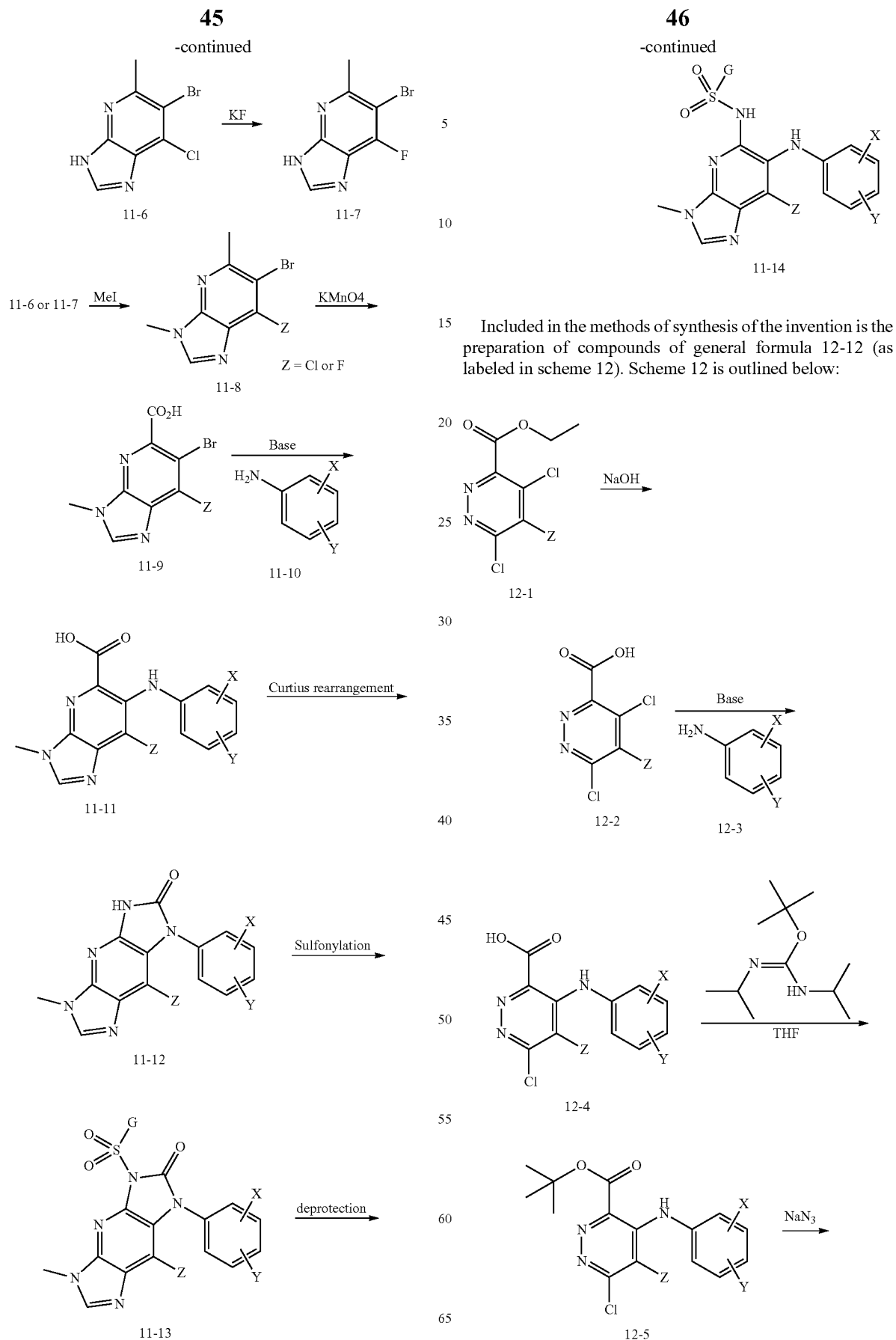
Included in the methods of synthesis of the invention is the preparation of compounds of general formula 12-12 (as labeled in scheme 12). Scheme 12 is outlined below:

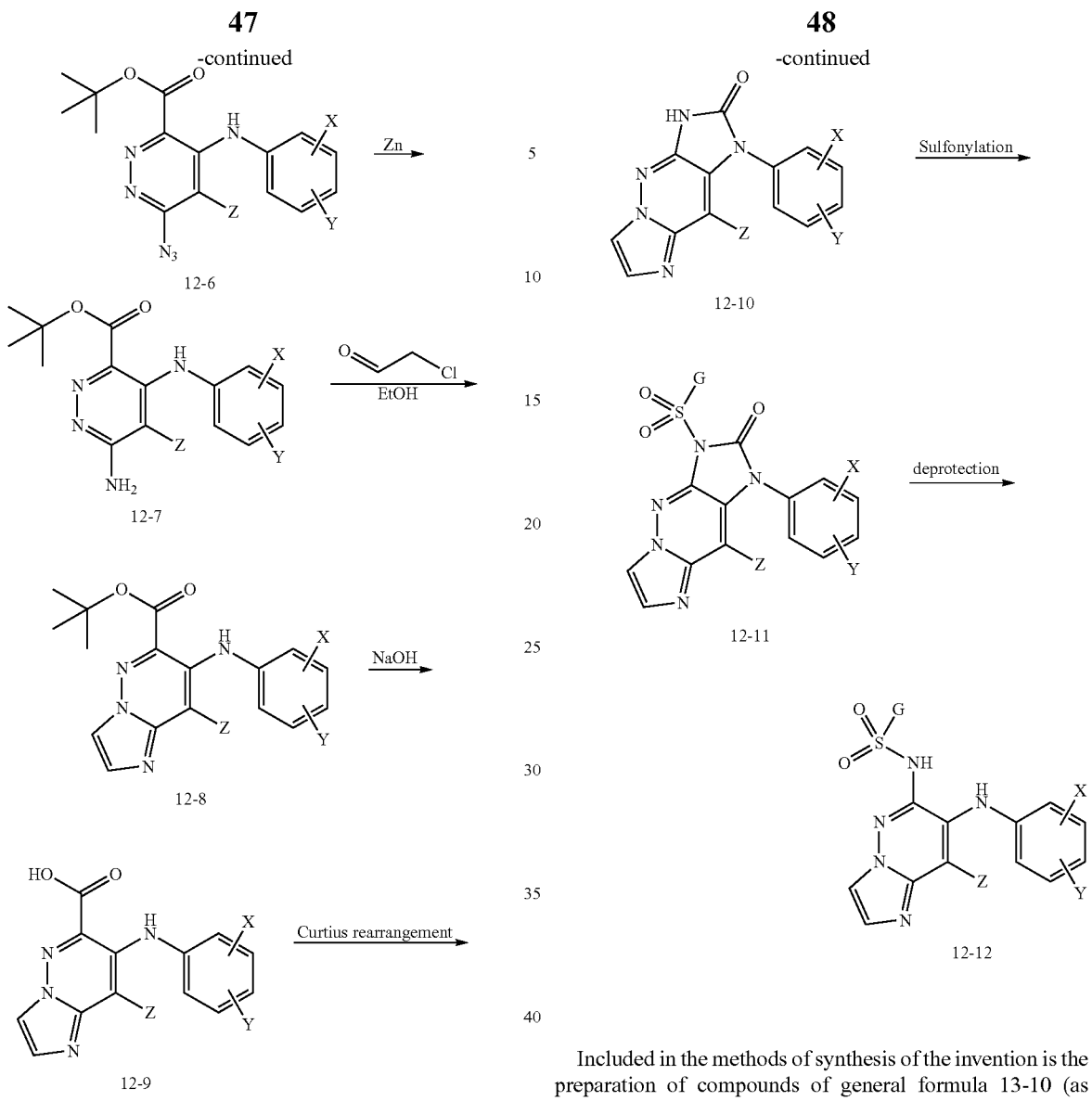
Included in the methods of synthesis of the invention is the preparation of compounds of general formula 13-10 (as labeled in scheme 13). Scheme 13 is outlined below:
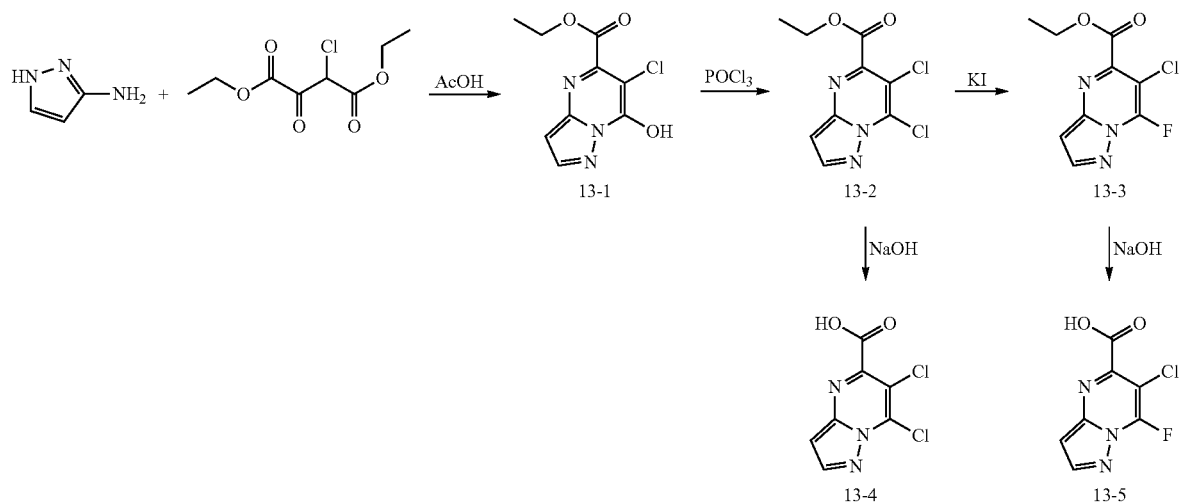

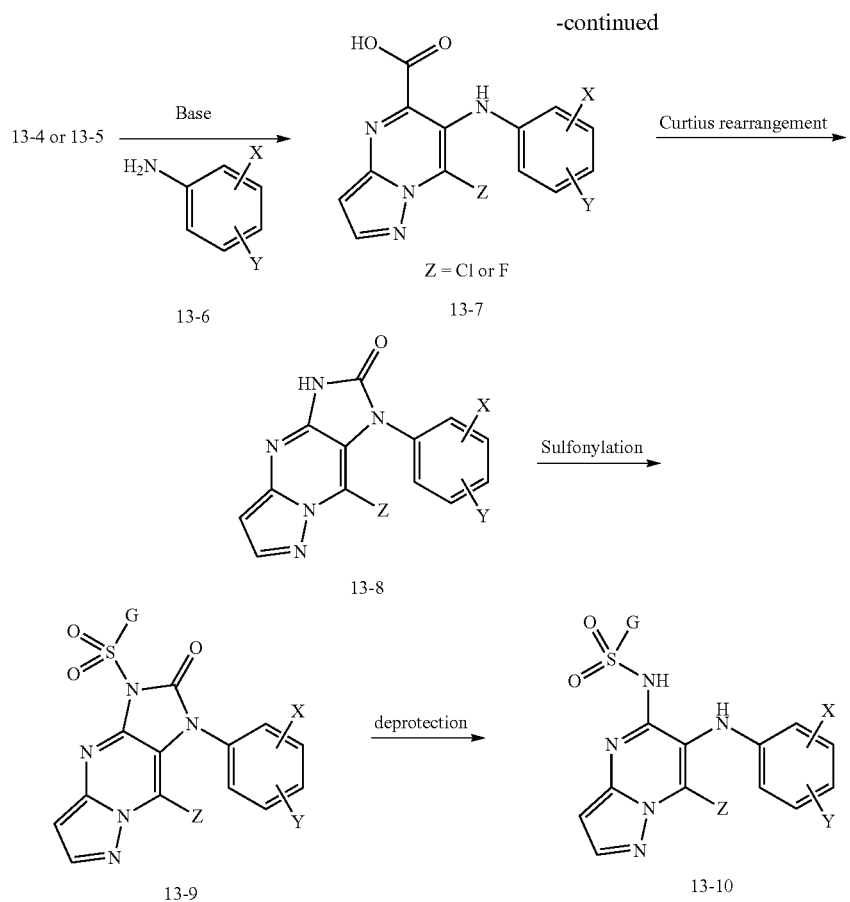
Included in the methods of synthesis of the invention is the preparation of compounds of general formula 14-14 (as labeled in scheme 14). Scheme 14 is outlined below:
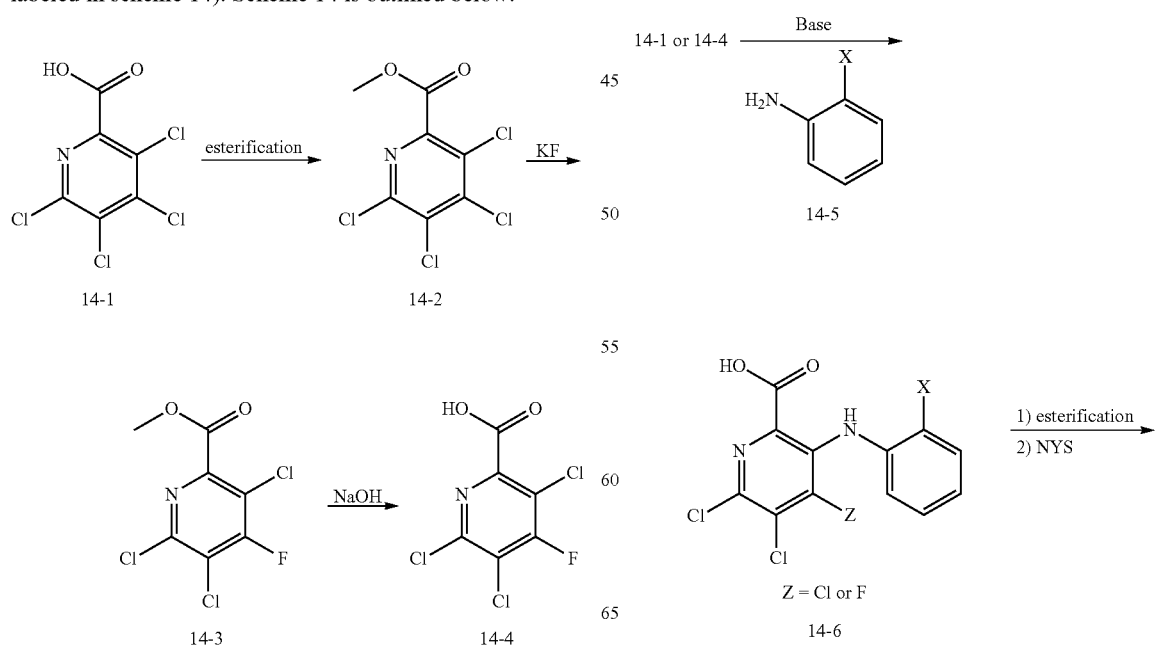

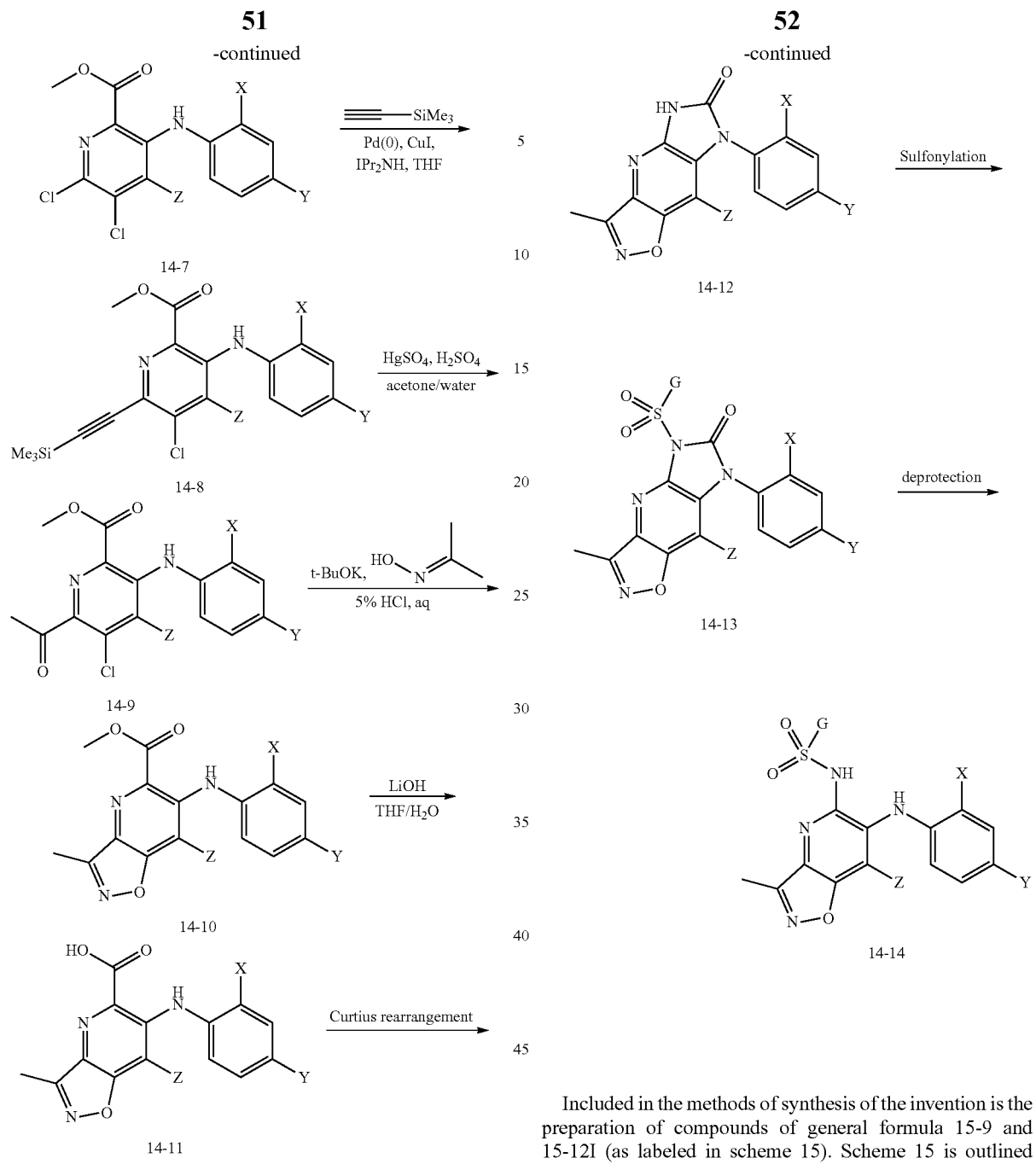
Included in the methods of synthesis of the invention is the preparation of compounds of general formula 15-9 and 15-12I (as labeled in scheme 15). Scheme 15 is outlined below:
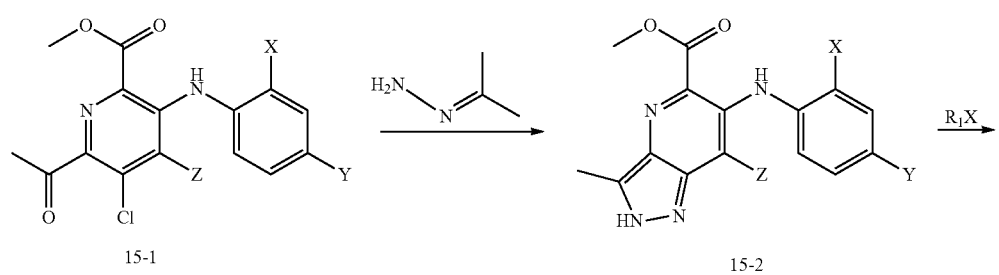

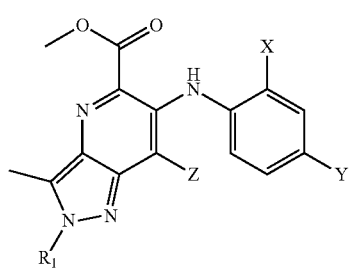 15-3
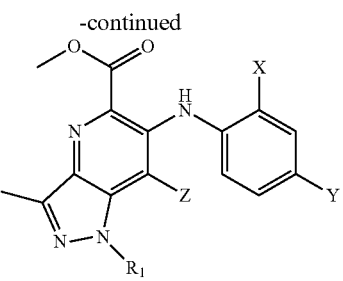 -continued
15-4
↓ NaOH    ↓ NaOH
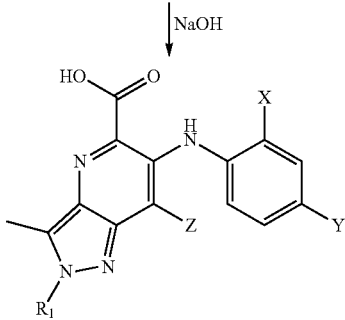 15-5
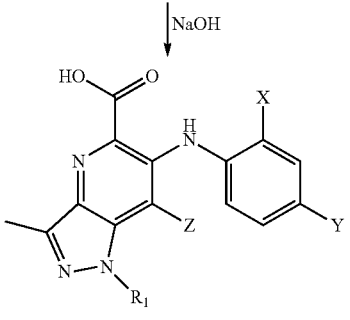 15-6
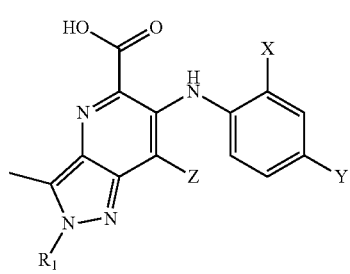 15-5
—Curtius Rearrangement→
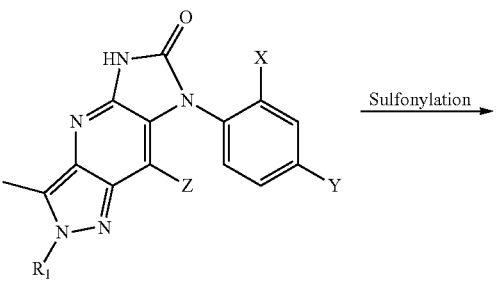 15-7
—Sulfonylation→
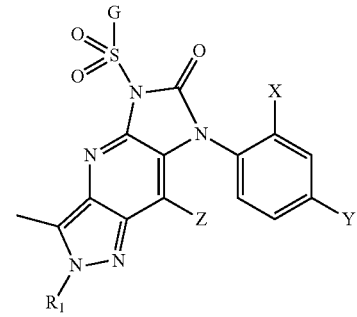 15-8
—Deprotection→
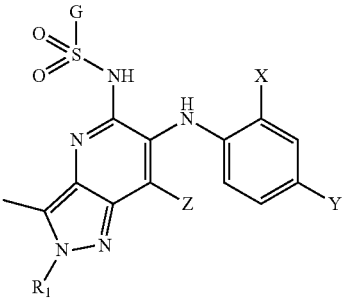 15-9
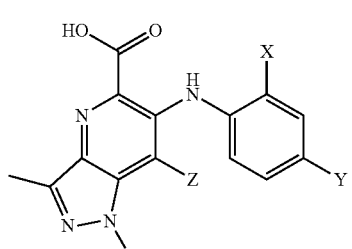 15-6
—Curtius Rearrangement→
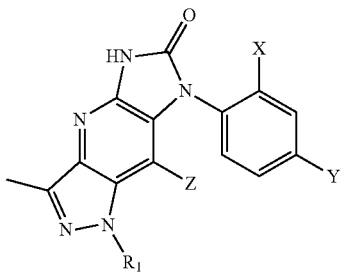 15-10
—Sulfonylation→

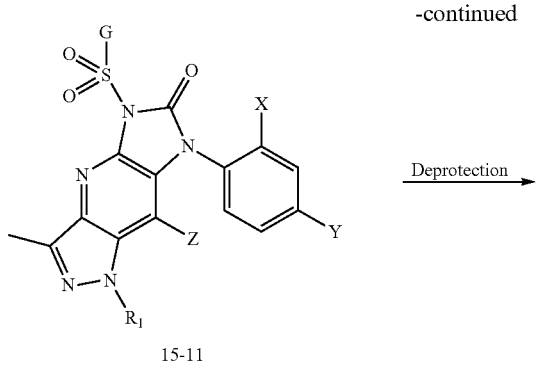
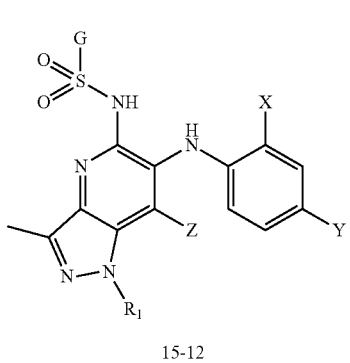
Included in the methods of synthesis of the invention is the preparation of compounds of general formula 16-7 (as labeled in scheme 16). Scheme 16 is outlined below:
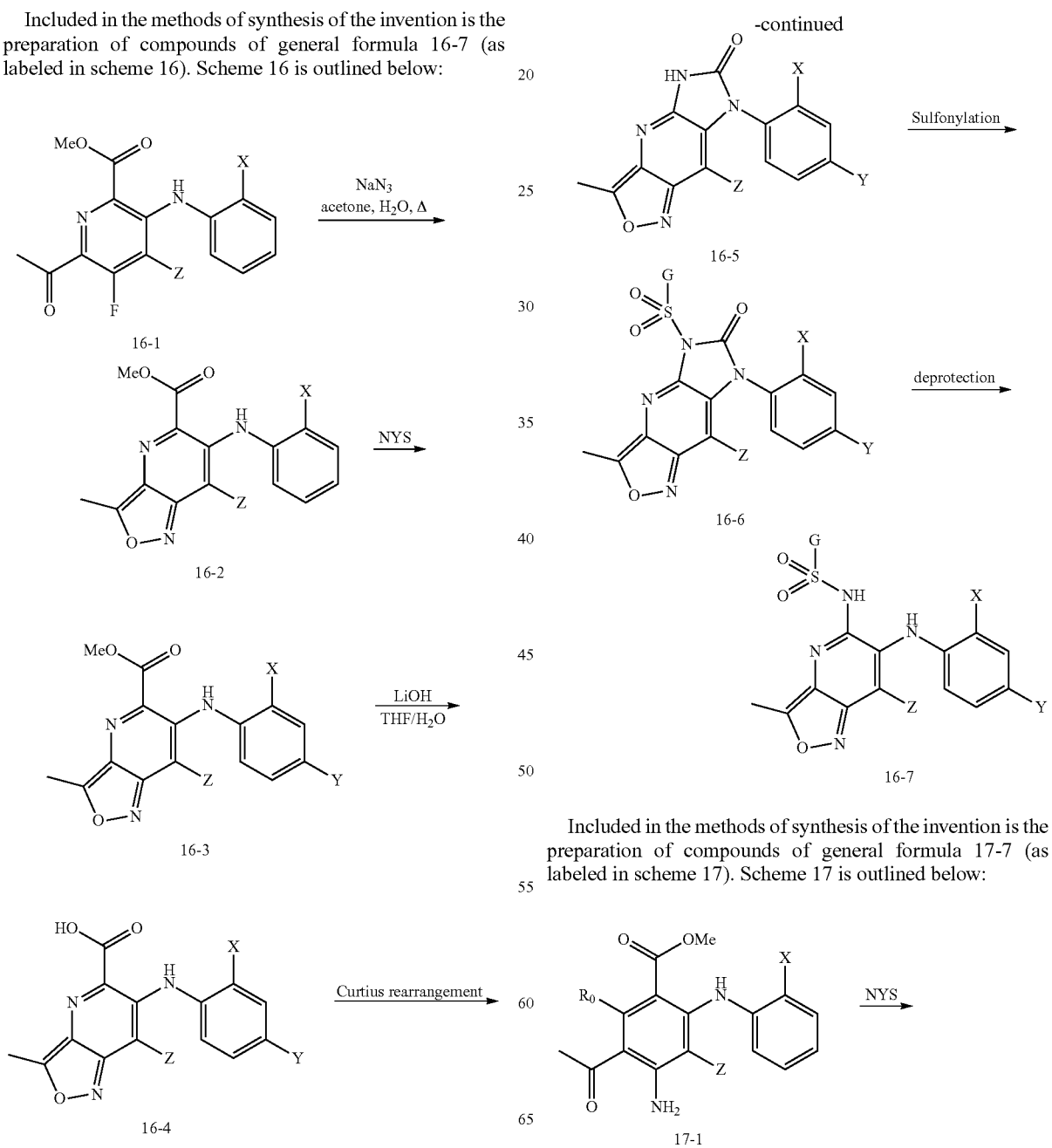
Included in the methods of synthesis of the invention is the preparation of compounds of general formula 17-7 (as labeled in scheme 17). Scheme 17 is outlined below:
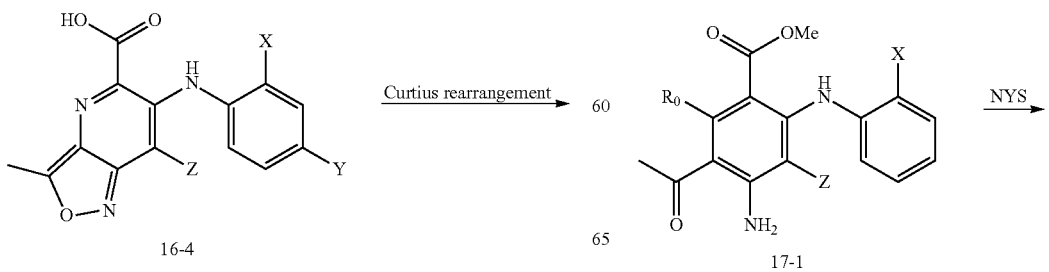

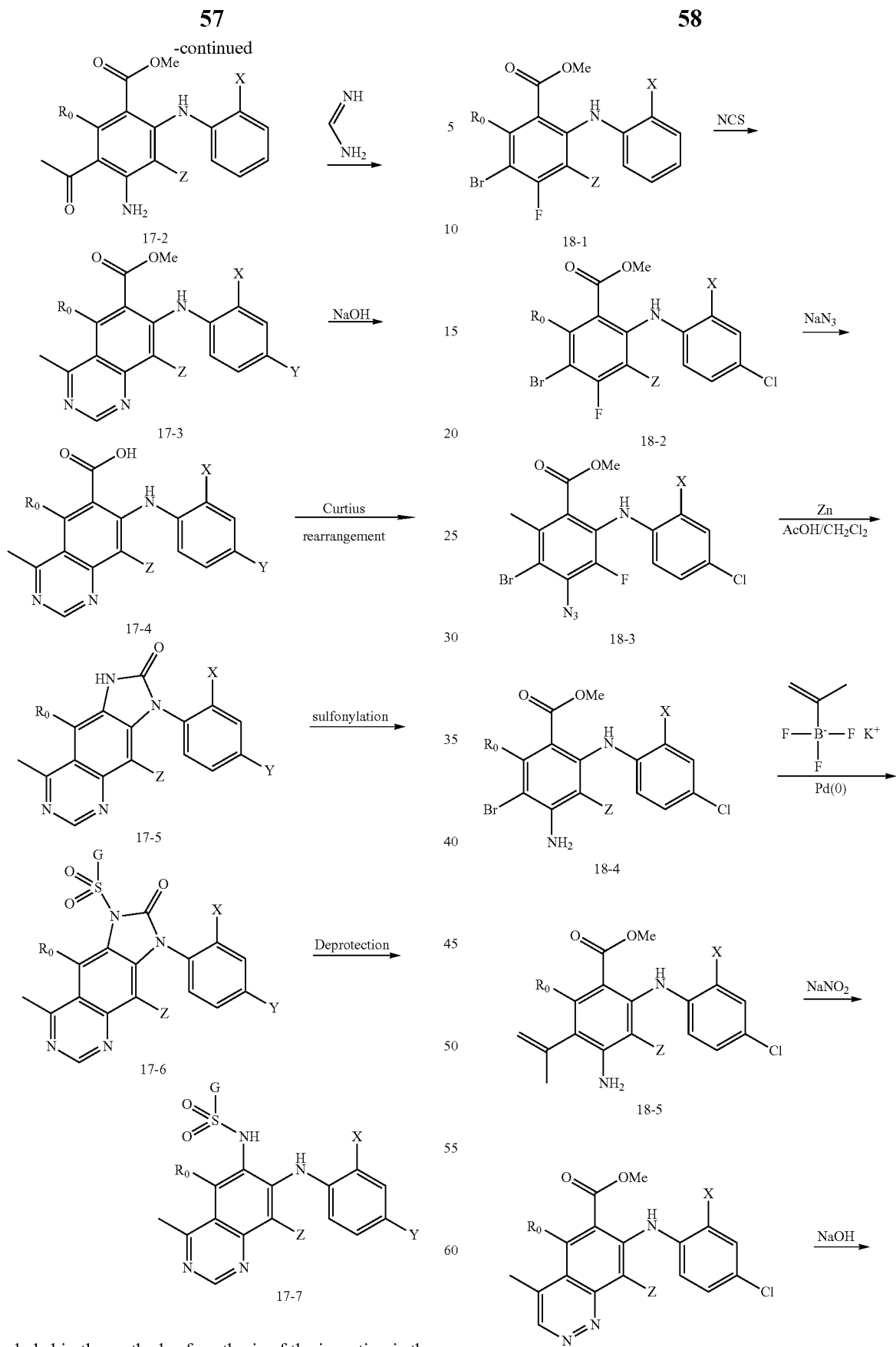
Included in the methods of synthesis of the invention is the preparation of compounds of general formula 18-10 (as labeled in scheme 18). Scheme 18 is outlined below:

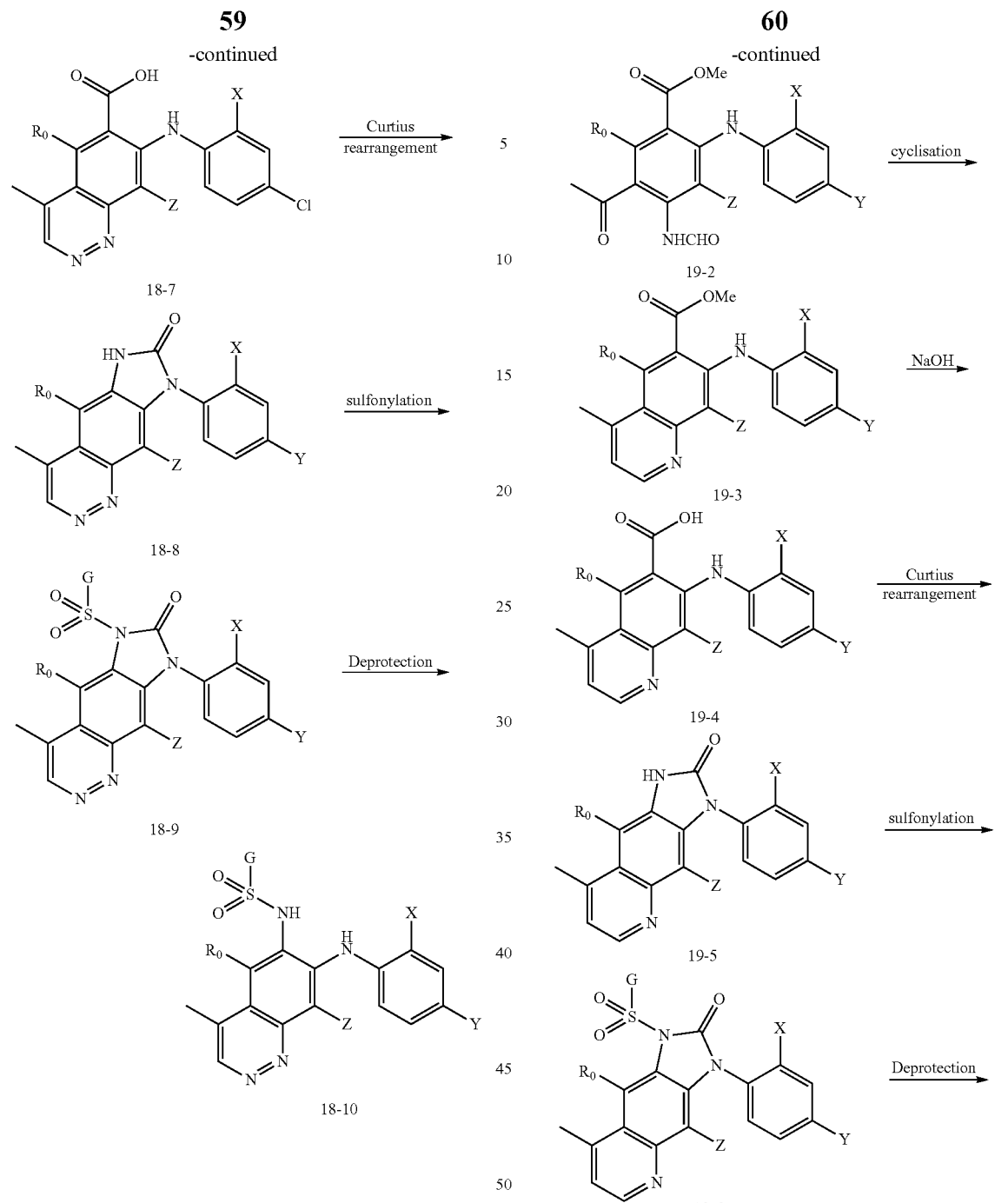
Included in the methods of synthesis of the invention is the preparation of compounds of general formula 19-7 (as labeled in scheme 19). Scheme 19 is outlined below:
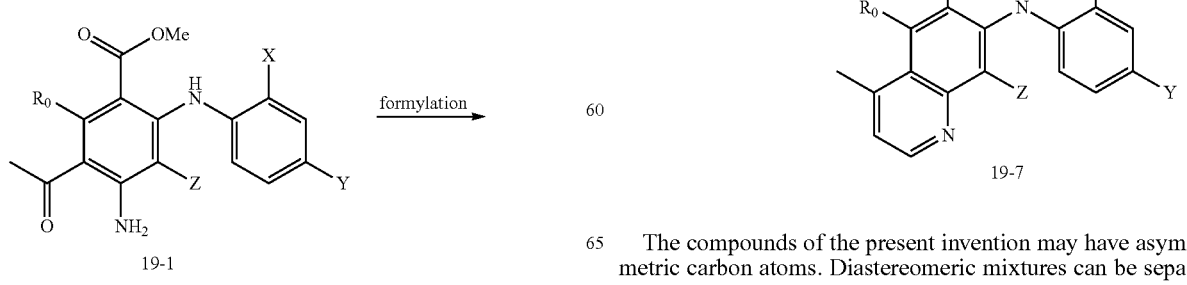
The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g. alcohol), separating the diastereomers and converting (e.g., hydrolyzing) the individual diastereomers to the corresponding pure enantiomers. All such isomers, including diastereomeric mixtures and pure enantiomers are considered as part of the invention.

The activity of the compounds of the present invention may be determined by the following procedure, as well as the procedure described in the examples below. N-terminal 6 His-tagged, constitutively active MEK1 (2-393) is expressed in $E.$ $coil$ and protein is purified by conventional methods (Ahn et al. $Science$ 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in $E.$ $coli$ and is purified by conventional methods, in the presence of MEK1. The assay is carried out in 96-well polypropylene plate. The incubation mixture (100, μL) comprises of 25 mM Hepes, pH 7.4, 10 mM $MgCl_2$, 5 mM β-glycerolphosphate, 100 μM Na-orthovanadate, 5 mM DTT, 5 nM MEK1, and 1 μM ERK2. Inhibitors are suspended in DMSO, and all reactions, including controls are performed at a final concentration of 1% DMSO. Reactions are initiated by the addition of 10 μM ATP (with 0.5 μCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filter plates, and excess labeled ATP washed off using a Tomtec MACH III harvestor. Plates are allowed to air-dry prior to adding 30 μL/well of Packard Microscint 20, and plates are counted using a Packard TopCount.

Administration of the compounds of the present invention (hereinafter the "active compound (s)") can be effected by any method that enables delivery of the compounds to the site of action. These methods include oral routes, intraduodenal mutes, parenteral injection (including intravenous, subcutaneous, intramuscular, intravascular or infusion), topical, and rectal administration.

The amount of the active compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

The active compound may be applied as a sole therapy or may involve one or more other anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

In still another aspect, the present invention provides kits for the treatment of disorders, such as the ones described herein. These kits comprise a compound or compounds described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

N-(4-fluoro-5-(2-fluoro-4-iodophenylamino)-1-methyl-1H-benzo[d]imidazol-6-yl)-1-(2-hydroxyethyl) cyclopropane-1-sulfonamide Step A: 2,3,4-Trifluoro-5-nitrobenzoic acid

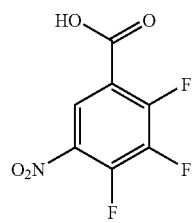

Fuming nitric acid (1.7 ml) is added dropwise to concentrated sulfuric acid (25 ml) while maintaining the temperature at 5-10° C. 2,3,4-Trifluorobenzoic acid (5 g, 28 mmoles) is added in small portion to this solution while keeping the reaction temperature at 5° C. After completion the reaction mixture is stirred at room temperature for an additional 2 hours and poured into ice. The mixture is extracted with ether (3×75 ml). The organic layers are combined, washed with brine, dried (MgSO$_4$). The solvent is removed, and the crude product is recrystallized from hot chloroform to obtain the title compound.

Step B: 3,4-Difluoro-2-(2-fluoro-4-iodophenylamino)-5-nitrobenzoic acid

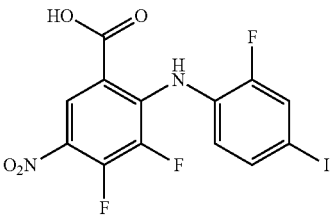

To a solution of 2-fluoro-4-iodoaniline (2.9 g, 11.8 mmoles) in 50 ml anhydrous THF at −60° C., 40 ml of a 1M solution of LHMDS in THF (40 mmoles) is added dropwise. In a separate flask, 2,3,4-trifluoro-5-nitrobenzoic acid (5 g, 22.6 mmoles), previously dissolved in THF (50 ml), is treated, at −60° C., with 25 ml of a 1M solution of LHMDS in THF (25 mmoles). Both solutions are stirred at −78° C. for 45 min and the second solution is transferred via cannula to the first reaction mixture. After completion of the addition the resulting mixture is stirred under argon at room temperature for 15 hours. The reaction mixture is quenched with water, then 1N HCl is added (pH=0-1) followed by brine (100 ml). The crude material is extracted with THF (3×100 ml), the organic layers are combined and dried (Na$_2$SO$_4$) and the solvent is removed to give the title compound.

Step C: Methyl 3,4-difluoro-2-(2-fluoro-4-iodophenylamino)-5-nitrobenzoate

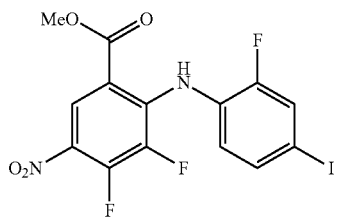

To a solution of 3,4-difluoro-2-(2-fluoro-4-iodophenylamino)-6-nitrobenzoic acid (8.5 g, 194 mmoles) in acetone (50 ml) is added sodium bicarbonate (5 g, 58.2 mmoles). The reaction mixture is stirred at room temperature for 10 min, dimethylsulfate (4.5 ml, 44.6 mmoles) is added and the mixture is heated under reflux for 3 hours. The solvent is removed under reduced pressure. The yellow residue is triturated in hot methanol. The solid is isolated by filtration, washed with MeOH and dried under vacuum to obtain the title compound.

Step D: Methyl 4-(allylamino)-3-fluoro-2-(2-fluoro-4-iodophenylamino)-5-nitrobenzoate

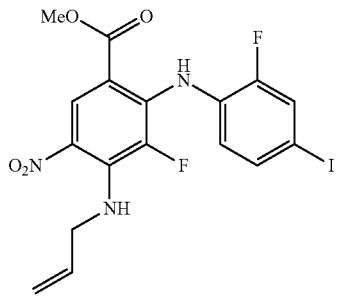

A suspension of methyl 3,4-difluoro-2-(2-fluoro-4-iodophenylamino)-5-nitrobenzoate (3.9 g, 8.62 mmoles) and allylamine (3.5 ml, 43 mmoles) in a mixture of THF (10 ml), MeOH (10 ml) and H$_2$O (2.5 ml) is stirred at room temperature for 30 min. The yellow suspension is filtered and washed with hexane to remove the excess of allylamine. The resulting solid is dried under vacuum to obtain the title compound.

Step E: Methyl 4-(allylamino)-5-amino-3-fluoro-2-(2-fluoro-4-iodophenylamino)benzoate A suspension of methyl 4-(allylamino)-3-fluoro-2-(2-fluoro-4-iodophenylamino)-5-nitrobenzoate and ammonium chloride (4.42 g, 79 mmoles) in a mixture of MeOH (20 ml) and dioxane (20 ml) is heated until it became a clear solution. Iron powder (4.42 g, 79 mmoles) is added and the resulting mixture is heated under reflux overnight. Water is added and the reaction mixture is filtered through celite. The solvent is removed under reduced pressure and the crude material is purified by flash chromatography to give the title compound.

Step F: Methyl 1-allyl-7-fluoro-6-(2-fluoro-4-iodophenylamino)-1H-benzo[d]imidazole-5-carboxylate

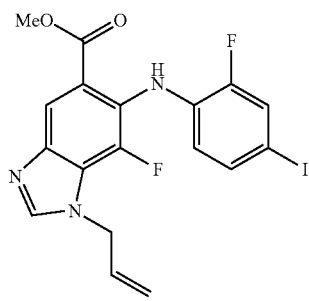

A stirred suspension of methyl 4-(allylamino)-5-amino-3-fluoro-2-(2-fluoro-4-iodophenylamino)benzoate (3.4 g, 7.4 mmoles)) and formamide acetate (3.8 g, 36.4 mmoles) in methanol (30 ml) is heated under reflux for 3 hours. The reaction mixture is cooled to room temperature and a saturated aqueous solution of sodium bicarbonate (30 ml) and water (30 ml) are added. The resulting precipitate is filtered and dried under vacuum to obtain the title compound.

Step G: Methyl 3-allyl-4-fluoro-5-(2-fluoro-4-iodophenylamino)-6-methoxycarbony-1-methyl-3H-benzoimidazol-1-ium iodide

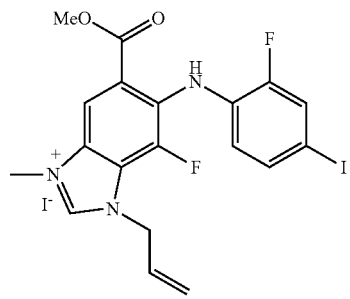

A mixture of methyl 1-allyl-7-fluoro-6-(2-fluoro-4-iodophenylamino)-1H-benzo[d]imidazole-5-carboxylate (2.67 g, 5.7 mmoles) acetonitrile (10 ml) and iodomethane (5.5 ml, 83 mmoles) are stirred at 50° C. in a sealed tube for 12 hours. The reaction mixture is cooled and placed under reduced pressure to remove the excess of iodomethane. The crude material is poured into ether and the solid is isolated by filtration. The brown solid is dried under vacuum to obtain the title compound.

Step H: Methyl 4-fluoro-5-(2-fluoro-4-iodophenylamino)-1-methyl-1H-benzo[d]imidazole-6-carboxylate

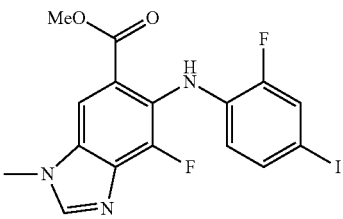

A mixture of methyl 3-allyl-4-fluoro-5-(2-fluoro-4-iodophenylamino)-6-methoxycarbony-1-methyl-3H-benzoimidazol-1-ium iodide, triphenyl phosphine (0.62 g, 2.5 mmoles), palladium tetrakis (0.47 g, 0.48 mmoles) in dichloromethane (15 ml) is cooled at −10° C. Pyrrolidine (0.65 ml) is added dropwise and the reaction mixture is stirred for 2 hours. Water is added and the mixture is extracted with dichloromethane. The organic phases are combined, washed with brine, dried Na₂SO₄ and concentrated under reduced pressure. The resulting solid is triturated with a mixture of Hexane/Ether (9/1) and isolated by filtration.

Step I: 4-Fluoro-5-(2-fluoro-4-iodophenylamino)-1-methyl-1H-benzo[d]imidazole-6-carboxylic acid

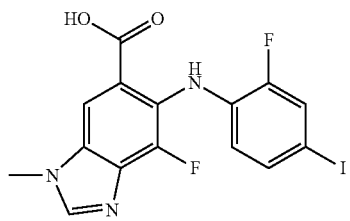

Methyl 4-fluoro-5-(2-fluoro-4-iodophenylamino)-1-methyl-1H-benzo[d]imidazole-6-carboxylate (2.15 g, 4.8 mmoles) is dissolved in a mixture of THF (30 ml), MeOH (10 ml) and H₂O (5 ml) and LiOH (1.16 g, 4.8 mmoles) is added. The mixture is stirred at room temperature for 2 hours. Solvents are removed under reduced pressure and 1N HCl is added. The aqueous layer is extracted with chloroform. The organic layers are combined, washed with brine, dried (Na₂SO₄) and concentrated under reduced pressure to obtain the title compound.

Step J: 1-(2-fluoro-4-iodophenylamino)-8-fluoro-5-methyl-benzimidazo[6,5-d]imidazole

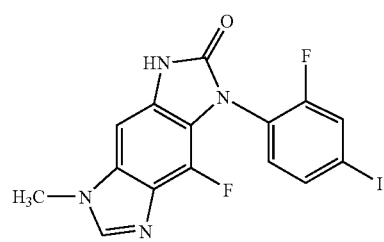

A mixture of 4-fluoro-5-(2-fluoro-4-iodophenylamino)-1-methyl-1H-benzo[d]imidazole-6-carboxylic acid (0.52 g, 1.2 mmoles), DPPA (0.52 ml, 2.4 mmoles) and triethylamine (1 ml, 06.0 mmoles) is refluxed for 3 hours. The solvent is removed under reduced pressure and the crude product is purified by flash chromatography using a gradient of EtOAc and hexane yielding the title compound.

Step K: 3-cyclopropanesulfonamide 1-(2-fluoro-4-iodophenylamino)-8-fluoro-5-methyl-benzimidazo[6,5-d]imidazole

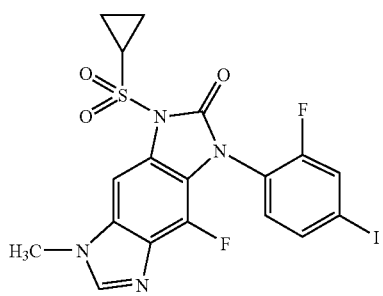

The previous compound (Step J) (50 mg, 0.117 mmoles) is dissolved in THF (2 ml) and the mixture is cooled at −78° C. LiHMDS (0.117 ml, 0.117 mmoles) is added dropwise followed by the addition of HMPA (0.5 ml). The mixture is warmed at room temperature and cyclopropyl sulfonyl chloride (0.013 ml, 0.14 mmoles) is added. After stirring at room temperature overnight, a saturated solution of ammonium chloride (5 ml) is added. The mixture is extracted with EtOAc (3×5 ml). The organic layers are combined, washed with brine, dried ($Na_2SO_4$) and concentrated under reduced pressure. The crude product is purified by flash chromatography using a gradient of EtOAc and hexane yielding to the title compound.

Step L: N-(4-fluoro-5-(2-fluoro-4-iodophenylamino)-1-methyl-1H-benzo[d]imidazol-6-yl)cyclopropanesulfonamide

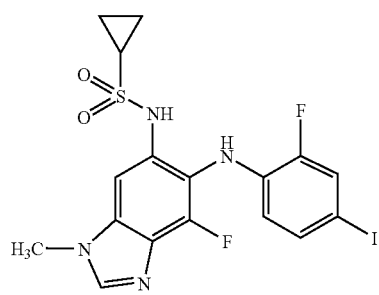

The previous compound (Step K) (26 mg, 0.049 mmoles), potassium trimethylsilanolate (21 mg, 0.149 mmoles) dissolved in THF (2 ml) are stirred at room temperature overnight. Brine (3 ml) is added and the mixture is extracted with EtOAc (3×5 ml). The organic layers are combined, dried ($Na_2SO_4$) and concentrated under reduced pressure. The crude product is purified by flash chromatography using a gradient of EtOAc and hexane yielding to the title compound.

Example 2

N-(4-fluoro-5-(2-fluoro-4-iodophenylamino)-1-methyl-1H-benzo[d]imidazol-6-yl)-1-(2-hydroxyethyl)cyclopropane-1-sulfonamide Step A: 2-(1-bromocyclopropyl)ethanol

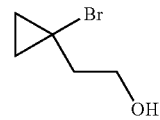

To a solution of neat diethyl zinc (3.3 ml, 3.977 g, 30 mmoles) in 100 ml anhydrous DCM was added very slowly trifluoroacetic acid (2.31 ml, 3.4188 g, 30 mmoles) dropwise at 0° C. (Caution: Violent gas evolution, exothermic!). After completed addition of the TFA, the suspension was stirred for 20 min at the same temperature, followed by the addition of diiodomethane (2.45 ml, 8.134 g, 30.4 mmoles). It was further stirred at 0° C. for 20 min, and then a solution of 3-bromobut-3-en-1-ol (1 ml, 1.523 g, 10.1 mmoles) in 10 ml DCM was added at the same temperature. After complete addition, the mixture was warmed to room temperature and stirred for 4 hours. The mixture was quenched with 100 ml MeOH and 40 ml brine, and it was further stirred for 30 min. The solvents were reduced, and the residue extracted using $CHCl_3$/aq. $NH_4Cl$. The organic layers were collected, washed with brine and water, and the solvent was removed to give 2-(1-bromocyclopropyl)-ethanol in sufficient purity (1.6564 g, 100%). $^1$H-NMR (500 MHz, $CDCl_3$): δ=3.90-3.83 (t, 2H), 1.91-1.87 (t, 2H), 1.71 (s, 1H, br), 1.14-1.09 (m, 2H), 0.83-0.79 (m, 2H).

Step B: (2-(1-bromocyclopropyl)ethoxy)(tert-butyl)dimethylsilane

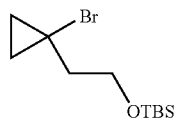

To a solution of the cyclopropyl alcohol (Step A) (1.303 g, 7.95 mmoles) in 30 ml anhydrous DCM was added anhydrous pyridine (1.2 ml, 1.1736 g, 14.8 mmoles), TBSOTf (2.7 ml, 3.1077 g, 11.76 mol) and the solution was stirred at room temperature for 16 h. It was extracted with $CHCl_3$/brine and the organic fraction was dried with $MgSO_4$. The solvent was reduced and the crude product purified using flash-column chromatography ($CHCl_3$/hexanes 1:10, $R_f$=0.4). Yield: 0.796 g, 36%. $^1$H-NMR (500 MHz, $CDCl_3$): δ=3.95-3.75 (t, 2H), 1.95-1.85 (t, 2H), 1.15-1.05 (m, 2H), 0.95-0.80 (m, 11H), 0.15-0.05 (s, 6H).

Step C: 1-(2-(tert-butyldimethylsilyloxy)ethyl)cyclopropane-1-sulfonyl chloride

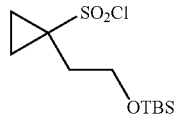

To a solution of the cyclopropyl bromide prepared in step B (1.1227 g, 4.04 mmoles) in 15 ml anhydrous diethyl ether was added a 1.7 M solution of t-BuLi in pentane (4.8 ml, 8.16 mmoles) at −78° C. The solution was stirred for 30 min at this temperature, and was then transferred via a transfer cannula into a solution of freshly distilled sulfuryl chloride (0.65 ml, 1.029 g, 8.1 mmoles) in 8 ml diethyl ether at −78° C. The yellow suspension was warmed to room temperature. The solvent was removed, and the residue was dried in vacuo to remove excessive sulfuryl chloride. Then, the residue was extracted two times with hexane, and after filtration the solvent was evaporated in vacuo to give the sulfonyl chloride in sufficient purity as a colorless oil. Yield: 870 mg (72%). $^1$H-NMR (300 MHz, CDCl$_3$): δ=3.95-3.85 (t, 2H), 2.35-2.25 (t, 2H), 1.80-1.70 (m, 2H), 1.45-1.38 (m, 2H), 0.90 (s, 9H), 0.10 (s, 6H).

Step D: 1-(2-(tert-butyldimethylsilyloxy)ethyl)-1-(2-fluoro-4-iodophenylamino)-8-fluoro-5-methyl-benzimidazo[6,5-d]imidazolecyclopropane-3-sulfonamide

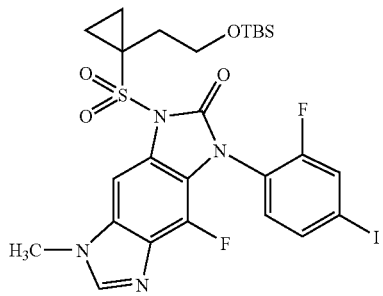

According to example 1 (step K), 1-(2-fluoro-4-iodophenylamino)-8-fluoro-5-methyl-benzimidazo[6,5-d]imidazole (81 mg, 0.19 mmoles) was reacted with the cyclopropylsulfonyl chloride (162 mg, 0.38 mmoles) prepared in step C to obtain the title product (46.6 mg, 36%). m/z=687 [M−1]$^-$.

Step E: 1-(2-(Tert-butyldimethylsilyloxy)ethyl)-N-(4-fluoro-5-(2-fluoro-4-iodophenylamino)-1-methyl-1H-benzo[d]imidazol-6-yl)cyclopropane-1-sulfonamide

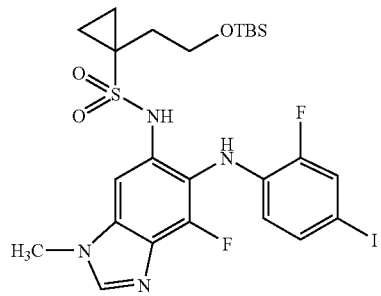

According to example 1 (step L) the previous compound (46.6 mg, 0.067 mmoles) was reacted with potassium trimethylsilanolate (26 mg, 0.230 mmoles) in THF (1.5 ml) to obtain the title compound (39 mg, 87%).

Step F: N-(4-fluoro-5-(2-fluoro-4-iodophenylamino)-1-methyl-1H-benzo[d]imidazol-6-yl)-1-(2-hydroxyethyl)cyclopropane-1-sulfonamide

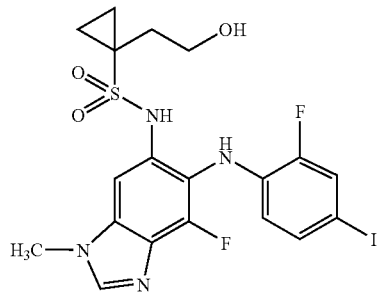

1-(2-(Tert-butyldimethylsilyloxy)ethyl)-N-(4-fluoro-5-(2-fluoro-4-iodophenylamino)-1-methyl-1H-benzo[d]imidazol-6-yl)cyclopropane-1-sulfonamide (39 mg, 0.06 mmoles) was dissolved in THF (0.5 ml) and aqueous hydrochloric acid (1.2 N, 0.5 ml) was added at 0° C. After stirring the reaction mixture for two hours, a saturated aqueous solution of sodium bicarbonate (5 ml) was added. The mixture was extracted with EtOAc (3×5 ml). The organic layers were combined, dried (Na$_2$SO$_4$) and concentrated under reduced pressure. The crude product was purified by flash chromatography using MeOH/CHCl$_3$ (1/9) yielding to the title compound (27 mg, 83%). m/z=549 [M+1]$^-$.

Example 3

N-(7-fluoro-6-(2-fluoro-4-iodophenylamino)-3-methylbenzo[d]isoxazol-5-yl)cyclopropanesulfonamide Step A: 5-Bromo-3,4-difluoro-2-(2-fluorophenylamino)benzoic acid

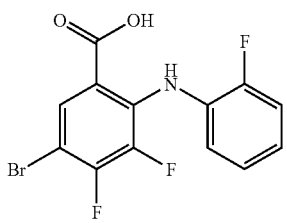

To a solution of 2-fluoroaniline (4.27 ml, 44.3 mmol) in THF (30 ml) at −78° C. was added LiHMDS (66.6 ml, 1 M in THF, 66.6 mmol) dropwise. The reaction mixture was stirred for 10 min and a solution of 5-bromo-2,3,4-trifluorobenzoic acid (5.63 g, 22.2 mmol) in THF (40 ml) was added to the mixture. The reaction was slowly warmed to room temperature and stirred at this temperature for 4 h. The mixture was concentrated, quenched with 10% HCl solution (70 ml), and extracted with EtOAc (2×200 ml). The combined organic solution was dried over MgSO$_4$ and concentrated to dryness. Purification by trituration with boiling CH$_2$Cl$_2$ gave 4.40 g (57%) of 5-bromo-3,4-difluoro-2-(2-fluorophenylamino) benzoic acid as a yellow solid.

Step B: Methyl 5-bromo-3,4-difluoro-2-(2-fluorophenylamino)benzoate

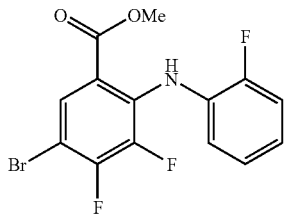

To a solution of 5-bromo-3,4-difluoro-2-(2-fluorophenylamino)benzoic acid (3.0 g, 8.67 mmol) in a mixture of THF (15 ml) and MeOH (5 ml) was added (trimethylsilyl)diazomethane (5.63 ml, 2 M in Hexanes, 11.3 ml). After stirring for 4 h, the reaction was quenched with AcOH and diluted with EtOAc (100 ml). The organic solution was washed with H₂O (50 ml) and brine (50 ml), dried over Na₂SO₄ and concentrated to dryness to give 2.83 g (91%) of methyl 5-bromo-3,4-difluoro-2-(2-fluorophenylamino)benzoate as a light yellow solid.

Step C: Methyl 3,4-difluoro-2-(2-fluorophenylamino)-5-((trimethylsilyl)ethynyl)benzoate

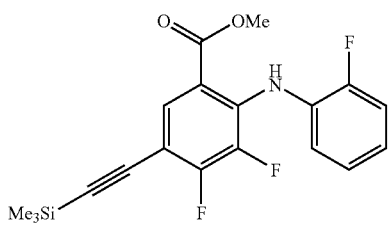

A mixture of methyl 5-bromo-3,4-difluoro-2-(2-fluorophenylamino)benzoate (2.70 g, 7.50 mmol), trimethylsilylacetylene (1.23 ml, 8.63 mmol), CuI (143 mg, 0.75 mmol), dichlorobis(triphenylphosphine)palladium (526 mg, 0.75 mmol) and i-Pr₂NH (2.12 ml, 15.0 mmol) in THF (40 ml) was stirred at room temperature for 16 h. The reaction was concentrated and diluted with EtOAc (100 ml). The organic solution was washed with saturated aqueous NH₄Cl (50 ml), dried over Na₂SO₄ and concentrated. Silica gel chromatography (EtOAc:Hexanes=5:95) yielded 2.40 g (85%) of methyl 3,4-difluoro-2-(2-fluorophenylamino)-5-((trimethylsilyl)ethynyl)benzoate as a tan solid.

Step D: Methyl 5-acetyl-3,4-difluoro-2-(2-fluorophenylamino)benzoate

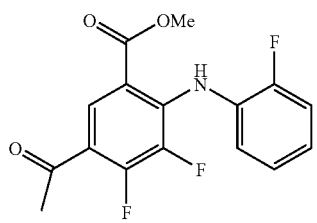

To a suspension of methyl 3,4-difluoro-2-(2-fluorophenylamino)-5-((trimethylsilyl)ethynyl)benzoate (1.20 g, 3.18 mmol) in 85% aqueous acetone (40 ml) were added HgSO₄ (943 mg, 3.18 mmol) and H₂SO₄ (0.33 ml, 6.36 mmol). The reaction was heated at reflux for 24 h. The mixture was cooled to room temperature, concentrated, and diluted with EtOAc (100 ml). The organic solution was washed with H₂O (50 ml), dried over Na₂SO₄ and concentrated. Silica gel chromatography (EtOAc:Hexanes=10:90) yielded 832 mg (81%) of methyl 5-acetyl-3,4-difluoro-2-(2-fluorophenylamino)benzoate as a white solid.

Step E: Methyl 7-fluoro-6-(2-fluorophenylamino)-3-methylbenzo[d]isoxazole-5-carboxylate

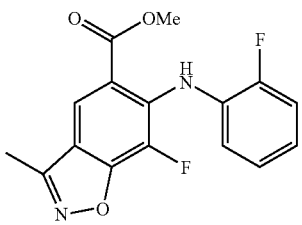

To a solution of acetone oxime (3.17 g, 43.3 mmol) in THF (40 ml) was added t-BuOK (43.3 ml, 1 M in THF, 43.3 mmol). After stirring at room temperature for 30 min, the mixture was cooled to −78° C. To the mixture was added a solution of methyl 5-acetyl-3,4-difluoro-2-(2-fluorophenylamino)benzoate (4.0 g, 12.4 mmol) in THF (70 ml) dropwise. After stirring at −78° C. for 15 min, the reaction was warmed to 0° C. and stirred at the temperature for 4 h. The reaction was quenched with saturated aqueous NH₄Cl solution (200 ml) and extracted with EtOAc (2×200 ml). The organic solution was washed with brine (100 ml), dried over MgSO₄ and concentrated. To the resulting oil was added a mixture of 5% HCl solution (100 ml) and MeOH (100 ml). The resulting suspension was heated at reflux for 1.5 h. The reaction was cooled to room temperature, concentrated to half volume, and diluted with EtOAc (200 ml). The organic solution was washed with brine (100 ml), dried over Na₂SO₄ and concentrated. Silica gel chromatography (EtOAc:Hexanes=25:75) yielded 2.84 g (72%) of methyl 7-fluoro-6-(2-fluorophenylamino)-3-methylbenzo[d]isoxazole-5-carboxylate as a white solid.

Step F: Methyl 7-fluoro-6-(2-fluoro-4-iodophenylamino)-3-methylbenzo[d]isoxazole-5-carboxylate

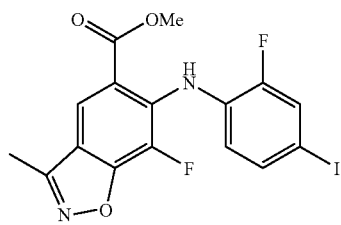

To a suspension of methyl 7-fluoro-6-(2-fluorophenylamino)-3-methylbenzo[d]isoxazole-5-carboxylate (2.84 g, 8.93 mmol) in DMF (50 ml) were added N-iodosuccinimide (3.01 g, 13.4 mmol) and TFA (3 ml). After stirring at room temperature for 4 h, the reaction was quenched with saturated aqueous NH$_4$Cl solution (100 ml) and extracted with EtOAc (2×100 ml). The combined organic solution was washed with brine (100 ml), dried over MgSO$_4$ and concentrated. Silica gel chromatography (EtOAc:Hexanes=25:75) yielded 3.77 g (95%) of methyl 7-fluoro-6-(2-fluoro-4-iodophenylamino)-3-methylbenzo[d]isoxazole-5-carboxylate as a tan solid.

Step G: 7-Fluoro-6-(2-fluoro-4-iodophenylamino)-3-methylbenzo[d]isoxazole-5-carboxylic acid

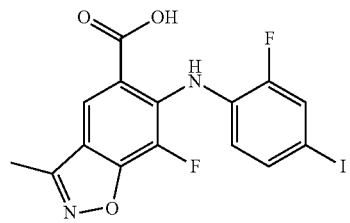

To a solution of methyl 7-fluoro-6-(2-fluoro-4-iodophenylamino)-3-methylbenzo[d]isoxazole-5-carboxylate (3.77 g, 8.49 mmol) in a mixture of THF (200 ml) and H$_2$O (100 ml) was added a solution of LiOH (1.20 g, 50 mmol) in H$_2$O (50 ml). After stirring at room temperature for 3 h, the reaction was concentrated, acidified with 1 M HCl solution, and extracted with EtOAc (2×100 ml). The organic solution was dried over Na$_2$SO$_4$ and concentrated to give 3.09 g (95%) of 7-fluoro-6-(2-fluoro-4-iodophenylamino)-3-methylbenzo[d]isoxazole-5-carboxylic acid as a light yellow solid.

Step H: 8-fluoro-1-(2-fluoro-4-iodophenyl)-5-methylbenzimidazolo[6,5-d][d]isoxazole

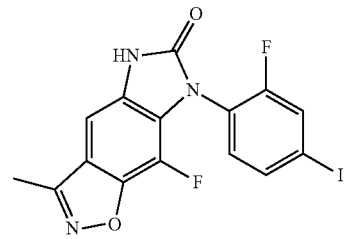

To a suspension of 7-fluoro-6-(2-fluoro-4-iodophenylamino)-3-methylbenzo[d]isoxazole-5-carboxylic acid (3.09 g, 8.08 mmol) in toluene (100 ml) was added triethylamine (3.37 ml, 24.2 mmol) and diphenylphosphoryl azide (2.18 ml, 10.1 mmol). The reaction was heated at reflux for 4 h. The mixture was cooled to room temperature and concentrated to dryness. Silica gel chromatography (EtOAc:Hexanes=75:25) yielded 2.06 g (60%) of 8-fluoro-1-(2-fluoro-4-iodophenyl)-5-methylbenzimidazolo[6,5-d][d]isoxazole as a tan solid.

Step I: 3-(Cyclopropanesulfonyl)-8-fluoro-1-(2-fluoro-4-iodophenyl)-5-methylbenzimidazolo[6,5-d][d]isoxazole

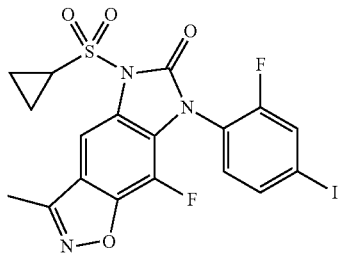

To a solution of 8-fluoro-1-(2-fluoro-4-iodophenyl)-5-methylbenzimidazolo[6,5-d][d]isoxazole (200 mg, 0.47 mmol) in THF (15 ml) at −78° C. was added LiHMDS (0.52 ml, 1 M in THF, 0.52 mmol). The reaction mixture was warmed to 0° C. and stirred at the temperature for 10 min. To the reaction was added cyclopropylsulfonyl chloride (99 mg, 0.71 mmol) and the mixture was warmed to room temperature. After stirring at room temperature for 16 h, the reaction was quenched with saturated aqueous NH$_4$Cl solution (20 ml) and extracted with EtOAc (2×30 ml). The combined organic solution was washed with brine (30 ml), dried over MgSO$_4$ and concentrated. Silica gel chromatography (EtOAc:Hexanes=25:75) yielded 222 mg (89%) of 3-(cyclopropanesulfonyl)-8-fluoro-1-(2-fluoro-4-iodophenyl)-5-methylbenzimidazolo[6,5-d][d]isoxazole as a white solid.

Step J: N-(7-fluoro-6-(2-fluoro-4-iodophenylamino)-3-methylbenzo[d]isoxazol-5-yl)cyclopropanesulfonamide

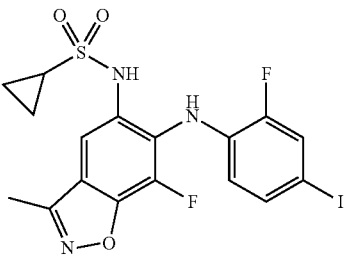

To a solution of 3-(cyclopropanesulfonyl)-8-fluoro-1-(2-fluoro-4-iodophenyl)-5-methylbenzimidazolo[6,5-d][d]isoxazole (139 mg, 0.26 mmol) in THF (15 ml) was added potassium trimethylsilanolate (101 mg, 0.78 mmol). The resulting cloudy solution was stirred at room temperature for 16 h. The reaction was quenched with saturated aqueous NH$_4$Cl solution (20 ml) and extracted with EtOAc (2×30 ml). The combined organic solution was washed with brine (30 ml), dried over MgSO$_4$ and concentrated. Silica gel chromatography (EtOAc:Hexanes=50:50) yielded 121 mg (92%) of N-(7-fluoro-6-(2-fluoro-4-iodophenylamino)-3-methylbenzo[d]isoxazol-5-yl)cyclopropanesulfonamide as a white solid. $^1$H NMR (DMSO-d$_6$, 400 MHz): δ 0.74 (m, 2H), 0.81

(m, 2H), 2.58 (m, 4H), 6.60 (m, 1H), 7.32 (d, J=8 Hz, 1H), 7.59 (d, J=12 Hz, 1H), 7.68 (s, 1H), 7.80 (s, 1H), 9.48 (s, 1H).

Example 4

1-(2-hydroxyethyl)-N-(7-fluoro-6-(2-fluoro-4-iodophenylamino)-3-methylbenzo[d]isoxazol-5-yl)cyclopropane-1-sulfonamide Step A: 3-(2-(tert-butyldimethylsilyloxy)ethyl)cyclopropanesulfonyl)-8-fluoro-1-(2-fluoro-4-iodophenyl)-5-methylbenzimidazolo[6,5-d][d]isoxazole

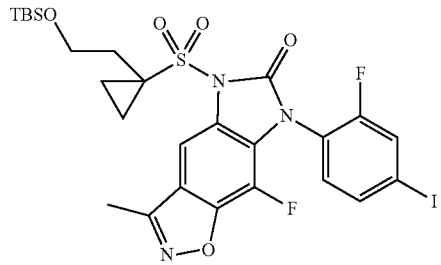

To a solution of 8-fluoro-1-(2-fluoro-4-iodophenyl)-5-methylbenzimidazolo[6,5-d][d]isoxazole (example 3, step H) (150 mg, 0.35 mmol) in THF (15 ml) at −78° C. was added LiHMDS (0.39 ml, 1 M in THF, 0.39 mmol). The reaction mixture was stirred at −78° C. for 30 min and 1-(2-(tert-butyldimethylsilyloxy)ethyl)cyclopropane-1-sulfonyl chloride (144 mg, 0.48 mmol) was added to the mixture. The reaction was slowly warmed to room temperature and stirred at the temperature for 16 h. The reaction was quenched with saturated aqueous NH$_4$Cl solution (20 ml) and extracted with EtOAc (2×30 ml). The combined organic solution was washed with brine (30 ml), dried over MgSO$_4$ and concentrated. Silica gel chromatography (EtOAc:Hexanes=10:90) yielded 43 mg (18%) of 3-(2-(tert-butyldimethylsilyloxy)ethyl)cyclopropanesulfonyl)-8-fluoro-1-(2-fluoro-4-iodophenyl)-5-methylbenzimidazolo[6,5-d][d]isoxazole as a light yellow oil.

Step B: 1-(2-(tert-butyldimethylsilyloxy)ethyl)-N-(7-fluoro-6-(2-fluoro-4-iodophenylamino)-3-methyl-benzo[d]isoxazol-5-yl)cyclopropane-1-sulfonamide

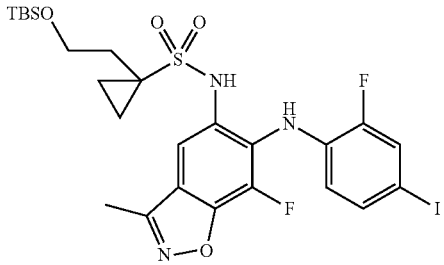

To a solution of 3-(2-(tert-butyldimethylsilyloxy)ethyl)cyclopropanesulfonyl)-8-fluoro-1-(2-fluoro-4-iodophenyl)-5-methylbenzimidazolo[6,5-d][d]isoxazole (43 mg, 0.062 mmol) in THF (5 ml) was added potassium trimethylsilanolate (40 mg, 0.31 mmol). The resulting solution was stirred at room temperature for 24 h. The reaction was quenched with saturated aqueous NH$_4$Cl solution (10 ml) and extracted with EtOAc (2×10 ml). The combined organic solution was washed with brine (10 ml), dried over MgSO$_4$ and concentrated. Silica gel chromatography (EtOAc:Hexanes=25:75) yielded 22 mg (53%) of 1-(2-(tert-butyldimethylsilyloxy)ethyl)-N-(7-fluoro-6-(2-fluoro-4-iodophenylamino)-3-methylbenzo[d]isoxazol-5-yl)cyclopropane-1-sulfonamide as a light yellow paste.

Step C: 1-(2-hydroxyethyl)-N-(7-fluoro-6-(2-fluoro-4-iodophenylamino)-3-methylbenzo[d]isoxazol-5-yl)cyclopropane-1-sulfonamide

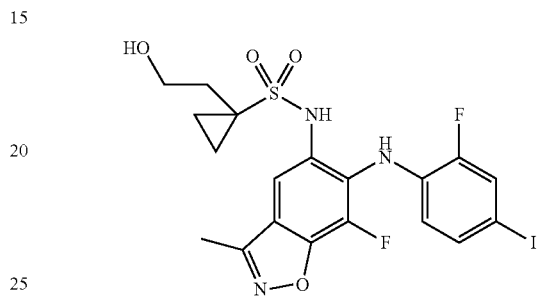

To a solution of 1-(2-(tert-butyldimethylsilyloxy)ethyl)-N-(7-fluoro-6-(2-fluoro-4-iodophenylamino)-3-methylbenzo[d]isoxazol-5-yl)cyclopropane-1-sulfonamide (20 mg, 0.030 mmol) in THF (2 ml) was added HCl (0.10 ml, 1.2 N in H$_2$O, 0.12 mmol). After stirring for 1 h, the reaction was quenched with saturated aqueous NaHCO$_3$ solution (3 ml) and extracted with EtOAc (2×10 ml). The combined organic solution was dried over Na$_2$SO$_4$ and concentrated. Silica gel chromatography (EtOAc:Hexanes=75:25) yielded 10 mg (61%) of 1-(2-hydroxyethyl)-N-(7-fluoro-6-(2-fluoro-4-iodophenylamino)-3-methylbenzo[d]isoxazol-5-yl)cyclopropane-1-sulfonamide as a white solid. $^1$H NMR (DMSO-d$_6$, 400 MHz): δ 0.75 (m, 2H), 0.87 (m, 2H), 1.84 (t, J=8 Hz, 2H), 2.57 (s, 3H), 3.38 (m, 2H), 4.52 (s, 1H), 6.59 (m, 1H), 7.34 (d, J=8 Hz, 1H), 7.60 (dd, J=4, 8 Hz, 1H), 7.68 (s, 1H), 7.84 (s, 1H), 9.58 (s, 1H).

Example 5

1-(2,3-dihydroxypropyl)-N-(7-fluoro-6-(2-fluoro-4-iodophenylamino)-3-methylbenzo[d]isoxazol-5-yl)cyclopropane-1-sulfonamide Step A: 3-(allylcyclopropanesulfonyl)-8-fluoro-1-(2-fluoro-4-iodophenyl)-5-methylbenzimidazolo[6,5-d][d]isoxazole

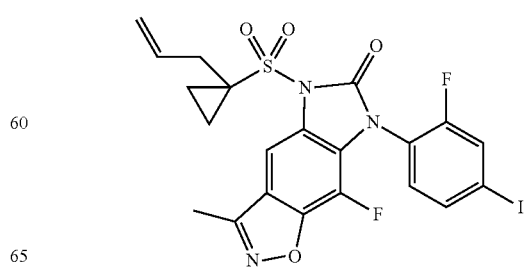

To a solution of 8-fluoro-1-(2-fluoro-4-iodophenyl)-5-methylbenzimidazolo[6,5-d][d]isoxazole (example 3, step H) (300 mg, 0.70 mmol) in THF (30 ml) at −78° C. was added LiHMDS (0.77 ml, 1 M in THF, 0.77 mmol). The reaction mixture was stirred at −78° C. for 30 min and 1-allylcyclopropane-1-sulfonyl chloride (253 mg, 1.40 mmol) was added to the mixture. The reaction was slowly warmed to room temperature and stirred at the temperature for 3 days. The reaction was quenched with saturated aqueous NH₄Cl solution (40 ml) and extracted with EtOAc (2×50 ml). The combined organic solution was washed with brine (50 ml), dried over MgSO₄ and concentrated. Silica gel chromatography (EtOAc:Hexanes=25:75) yielded 109 mg (27%) of 3-(allylcyclopropanesulfonyl)-8-fluoro-1-(2-fluoro-4-iodophenyl)-5-methylbenzimidazolo[6,5-d][d]isoxazole as a white solid.

Step B: 1-allyl-N-(7-fluoro-6-(2-fluoro-4-iodophenylamino)-3-methylbenzo[d]isoxazol-5-yl)cyclopropane-1-sulfonamide

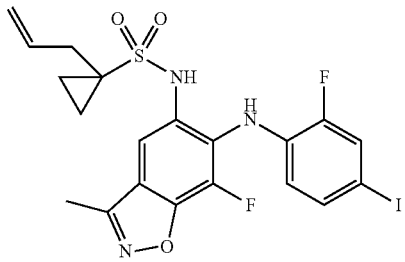

To a solution of 3-(allylcyclopropanesulfonyl)-8-fluoro-1-(2-fluoro-4-iodophenyl)-5-methylbenzimidazolo[6,5-d][d]isoxazole (133 mg, 0.23 mmol) in THF (10 ml) was added potassium trimethylsilanolate (36 mg, 0.28 mmol) at 0° C. The resulting solution was stirred at 0° C. for 5 h. The reaction was quenched with saturated aqueous NH₄Cl solution (10 ml) and extracted with EtOAc (2×10 ml). The combined organic solution was washed with brine (10 ml), dried over MgSO₄ and concentrated. Silica gel chromatography (EtOAc:Hexanes=50:50) yielded 53 mg (63%) of 1-allyl-N-(7-fluoro-6-(2-fluoro-4-iodophenylamino)-3-methylbenzo[d]isoxazol-5-yl)cyclopropane-1-sulfonamide as a light yellow paste.

Step C: 1-(2,3-dihydroxypropyl)-N-(7-fluoro-6-(2-fluoro-4-iodophenylamino)-3-methylbenzo[d]isoxazol-5-yl)cyclopropane-1-sulfonamide

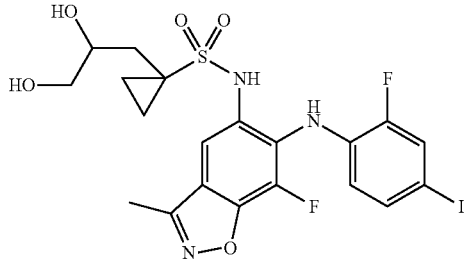

To a solution of 1-allyl-N-(7-fluoro-6-(2-fluoro-4-iodophenylamino)-3-methylbenzo[d]isoxazol-5-yl)cyclopropane-1-sulfonamide (92 mg, 0.17 mmol) in THF (5 ml) were added N-methylmorporine N-oxide (20 mg, 0.17 mmol) and osmium tetraoxide (0.11 mL, 4% in water, 0.017 mmol). After stirring for 16 h, the reaction was quenched with sodium sulfite solution (4 ml, 1M) and EtOAc (4 ml). The resulting mixture was stirred for 30 min and separated. The organic solution was dried over Na₂SO₄ and concentrated. Silica gel chromatography (MeOH:CH₂Cl₂=10:90) yielded 56 mg (57%) of 1-(2,3-dihydroxypropyl)-N-(7-fluoro-6-(2-fluoro-4-iodophenylamino)-3-methylbenzo[d]isoxazol-5-yl)cyclopropane-1-sulfonamide as a light purple paste. $^1$H NMR (DMSO-d₆, 400 MHz): δ 0.90 (m, 4H), 1.60 (m, 1H), 2.07 (m, 1H), 3.14 (m, 2H), 3.40 (m, 1H), 4.53 (t, 1H), 4.57 (d, 1H), 6.57 (m, 1H), 7.33 (d, J=8 Hz, 1H), 7.59 (d, J=11 Hz, 1H), 7.72 (s, 1H), 7.79 (s, 1H), 9.53 (s, 1H).

Example 6

N-(7-fluoro-6-(4-bromo-2-chlorophenylamino)-3-methylbenzo[d]isoxazol-5-yl)cyclopropanesulfonamide Step A: 8-fluoro-1-(4-bromo-2-chlorophenyl)-5-methylbenzimidazolo[6,5-d][d]isoxazole

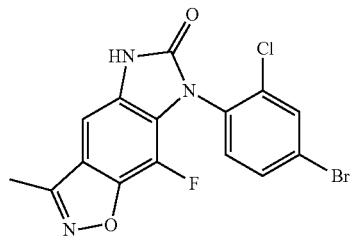

To a suspension of 7-fluoro-6-(4-bromo-2-chlorophenylamino)-3-methylbenzo[d]isoxazole-5-carboxylic acid (synthesized according to WO 2005/023759) (321 mg, 0.80 mmol) in toluene (20 ml) was added triethylamine (0.34 ml, 2.40 mmol) and diphenylphosphoryl azide (0.35 ml, 1.61 mmol). The reaction was heated at reflux for 4 h. The mixture was cooled to room temperature and concentrated to dryness. Silica gel chromatography (EtOAc:Hexanes=75:25) yielded 259 mg (82%) of 8-fluoro-1-(4-bromo-2-chlorophenyl)-5-methylbenzimidazolo[6,5-d][d]isoxazole as a tan solid.

Step B: 3-(Cyclopropanesulfonyl)-8-fluoro-1-(4-bromo-2-chlorophenyl)-5-methylbenzimidazolo[6,5-d][d]isoxazole

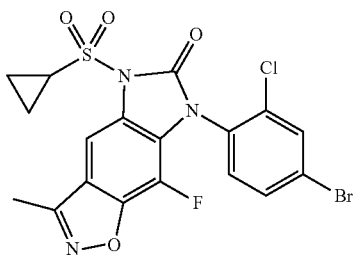

To a solution of 8-fluoro-1-(4-bromo-2-chlorophenyl)-5-methylbenzimidazolo[6,5-d][d]isoxazole (39 mg, 0.098 mmol) in THF (4 ml) at −78° C. was added LiHMDS (0.15 ml, 1 M in THF, 0.15 mmol). The reaction mixture was stirred at −78° C. for 10 min and cyclopropylsulfonyl chloride (28 mg, 0.20 mmol) was added to the mixture. The reaction was slowly warmed to room temperature and stirred at the temperature for 3 h. The reaction was quenched with saturated aqueous NH$_4$Cl solution (10 ml) and extracted with EtOAc (2×10 ml). The combined organic solution was washed with brine (10 ml), dried over MgSO$_4$ and concentrated. Silica gel chromatography (EtOAc:Hexanes=50:50) yielded 21 mg (43%) of 3-(cyclopropanesulfonyl)-8-fluoro-1-(4-bromo-2-chlorophenyl)-5-methylbenzimidazolo[6,5-d][d]isoxazole as a white solid.

Step C: N-(7-fluoro-6-(4-bromo-2-chlorophenylamino)-3-methylbenzo[d]isoxazol-5-yl)cyclopropanesulfonamide

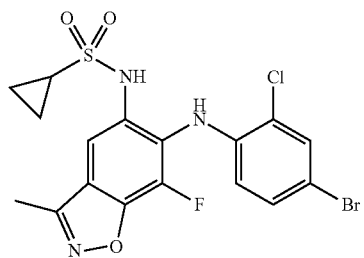

To a solution of 3-(cyclopropanesulfonyl)-8-fluoro-1-(4-bromo-2-chlorophenyl)-5-methylbenzimidazolo[6,5-d][d]isoxazole (21 mg, 0.042 mmol) in THF (3 ml) was added potassium trimethylsilanolate (16 mg, 0.13 mmol). The reaction was stirred at room temperature for 16 h, quenched with saturated aqueous NH$_4$Cl solution (10 ml) and extracted with EtOAc (2×10 ml). The combined organic solution was washed with brine (10 ml), dried over MgSO$_4$ and concentrated. Silica gel chromatography (EtOAc:Hexanes=75:25) yielded 20 mg (100%) of N-(7-fluoro-6-(4-bromo-2-chlorophenylamino)-3-methylbenzo[d]isoxazol-5-yl)cyclopropanesulfonamide as a white solid. $^1$H NMR (DMSO-d$_6$, 400 MHz): δ 0.83 (m, 4H), 2.60 (m, 4H), 6.68 (dd, J=4, 8 Hz, 1H), 7.29 (dd, J=4, 8 Hz, 1H), 7.59 (s, 1H), 7.68 (d, J=4 Hz, 1H), 7.72 (s, 1H), 9.68 (s, 1H).

Example 7

N-(7-fluoro-6-(2-fluoro-4-iodophenylamino)-3-methylbenzo[c]isoxazol-5-yl)cyclopropanesulfonamide Step A: Methyl 7-fluoro-6-(2-fluorophenylamino)-3-methylbenzo[c]isoxazole-5-carboxylate

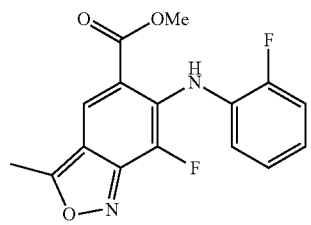

To a solution of methyl 5-acetyl-3,4-difluoro-2-(2-fluorophenylamino)benzoate (example 3, step D) (1.50 g, 4.64 mmol) in a mixture of acetone (36 ml) and H$_2$O (12 ml) was added NaN$_3$ (452 mg, 6.96 mmol). The reaction was heated at 65° C. for 16 h and cooled to room temperature. Acetone was concentrated and the resulting mixture was extracted with EtOAc (2×50 ml). The combined organic solution was washed with brine (50 ml), dried over MgSO$_4$ and concentrated to give a yellow solid. To the solid was added H$_2$O (24 ml) and the reaction was heated at reflux for 3 h. The reaction was cooled to room temperature, filtered, and washed with H$_2$O. The resulting solid was dried under high vacuum with P$_2$O$_5$ at 65° C. for 24 h to give 1.31 g (89%) of methyl 7-fluoro-6-(2-fluorophenylamino)-3-methylbenzo[c]isoxazole-5-carboxylate as a yellow solid.

Step B: methyl 7-fluoro-6-(2-fluoro-4-iodophenylamino)-3-methylbenzo[c]isoxazole-5-carboxylate

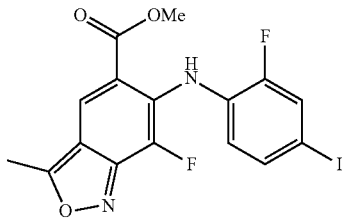

To a suspension of methyl 7-fluoro-6-(2-fluorophenylamino)-3-methylbenzo[c]isoxazole-5-carboxylate (1.31 g, 4.12 mmol) in DMF (40 ml) was added N-iodosuccinimide (1.39 g, 6.17 mmol) and TFA (2.4 ml). After stirring at room temperature for 4 h, the reaction was quenched with saturated aqueous NH$_4$Cl solution (100 ml) and extracted with EtOAc (2×100 ml). The combined organic solution was washed with brine (100 ml), dried over MgSO$_4$ and concentrated. Silica gel chromatography (EtOAc:Hexanes=25:75) yielded 1.71 g (93%) of methyl 7-fluoro-6-(2-fluoro-4-iodophenylamino)-3-methylbenzo[c]isoxazole-5-carboxylate as a brown solid.

Step C: 7-fluoro-6-(2-fluoro-4-iodophenylamino)-3-methylbenzo[c]isoxazole-5-carboxylic acid

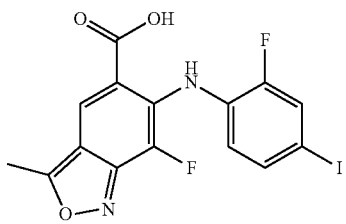

To a solution of methyl 7-fluoro-6-(2-fluoro-4-iodophenylamino)-3-methylbenzo[c]isoxazole-5-carboxylate (214 mg, 0.48 mmol) in a mixture of THF (10 ml) and H$_2$O (5 ml) was added a solution of LiOH (57.5 mg, 2.40 mmol) in H$_2$O (2.4 ml). After stirring at room temperature for 4 h, the reaction was concentrated, acidified with 1 M HCl solution, and extracted with EtOAc (2×20 ml). The organic solution was dried over MgSO$_4$ and concentrated to give 184 mg (100%) of 7-fluoro-6-(2-fluoro-4-iodophenylamino)-3-methylbenzo[c]isoxazole-5-carboxylic acid as an orange solid.

Step D: 8-fluoro-1-(2-fluoro-4-iodophenyl)-5-methylbenzimidazolo[6,5-d][c]isoxazole

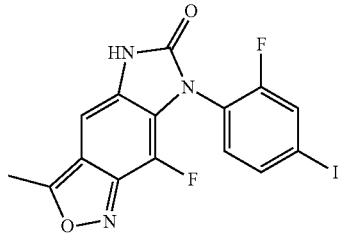

To a suspension of 7-fluoro-6-(2-fluoro-4-iodophenylamino)-3-methylbenzo[c]isoxazole-5-carboxylic acid (184 mg, 0.48 mmol) in toluene (10 ml) was added triethylamine (0.20 ml, 1.44 mmol) and diphenylphosphoryl azide (0.21 ml, 0.96 mmol). The reaction was heated at reflux for 4 h. The mixture was cooled to room temperature and concentrated to dryness. Silica gel chromatography (EtOAc:Hexanes=75:25) yielded 132 mg (64%) of 8-fluoro-1-(2-fluoro-4-iodophenyl)-5-methylbenzimidazolo[6,5-d][c]isoxazole as a tan solid.

Step E: 3-(cyclopropanesulfonyl)-8-fluoro-1-(2-fluoro-4-iodophenyl)-5-methylbenzimidazolo[6,5-d][c]isoxazole

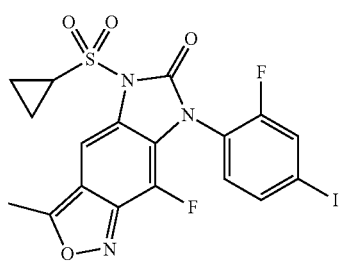

To a solution of 8-fluoro-1-(2-fluoro-4-iodophenyl)-5-methylbenzimidazolo[6,5-d][c]isoxazole (124 mg, 0.29 mmol) in THF (10 ml) at −78° C. was added LiHMDS (0.35 ml, 1 M in THF, 0.35 mmol). The reaction mixture was stirred at −78° C. for 10 min and cyclopropylsulfonyl chloride (61 mg, 0.44 mmol) was added to the mixture. The reaction is slowly warmed to room temperature and stirred at the temperature for 16 h. The reaction was quenched with saturated aqueous NH$_4$Cl solution (20 ml) and extracted with EtOAc (2×20 ml). The combined organic solution was washed with brine (20 ml), dried over MgSO$_4$ and concentrated. Silica gel chromatography (EtOAc:Hexanes=25:75) yielded 122 mg (79%) of 3-(cyclopropanesulfonyl)-8-fluoro-1-(2-fluoro-4-iodophenyl)-5-methylbenzimidazolo[6,5-d][c]isoxazole as a yellow solid.

Step F: N-(7-fluoro-6-(2-fluoro-4-iodophenylamino)-3-methylbenzo[c]isoxazol-5-yl)cyclopropanesulfonamide

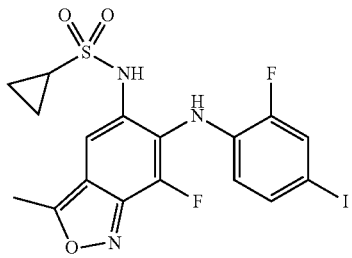

To a solution of 3-(cyclopropanesulfonyl)-8-fluoro-1-(2-fluoro-4-iodophenyl)-5-methylbenzimidazolo[6,5-d][c]isoxazole (120 mg, 0.23 mmol) in THF (15 ml) was added potassium trimethylsilanolate (87 mg, 0.68 mmol). The reaction was stirred at room temperature for 16 h, quenched with saturated aqueous NH$_4$Cl solution (20 ml), and extracted with EtOAc (2×30 ml). The combined organic solution was washed with brine (30 ml), dried over MgSO$_4$, and concentrated. Silica gel chromatography (EtOAc:Hexanes=50:50) yielded 106 mg (92%) of N-(7-fluoro-6-(2-fluoro-4-iodophenylamino)-3-methylbenzo[c]isoxazol-5-yl)cyclopropanesulfonamide as a light yellow solid. $^1$H NMR (DMSO-d$_6$, 400 MHz): δ 0.73 (m, 2H), 0.85 (m, 2H), 2.63 (m, 1H), 2.85 (s, 3H), 6.65 (m, 1H), 7.36 (d, J=8 Hz, 1H), 7.58 (s, 1H), 7.62 (m, 2H), 9.39 (s, 1H).

Example 8

N-(7-fluoro-6-(2-fluoro-4-iodophenylamino)-3-methylbenzo[c]isoxazol-5-yl)-1-(2-hydroxyethyl)cyclopropane-1-sulfonamide

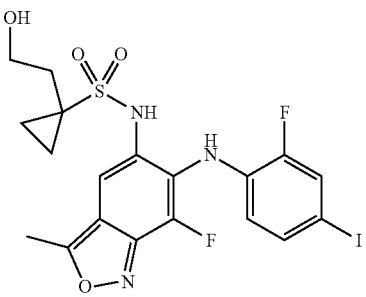

This compound is synthesized from 8-fluoro-1-(2-fluoro-4-iodophenyl)-5-methylbenzimidazolo[6,5-d][c]isoxazole according to example 4 (step A, B and C).

Example 9

N-(7-(4-bromo-2-chlorophenylamino)-8-chloroimidazo[1,2-a]pyridin-6-yl)cyclopropanesulfonamide Step A: Methyl 4,6-dichloronicotinate

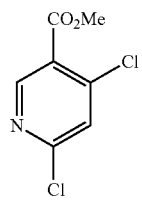

To a suspension of methyl 4,6-dihydroxynicotinate (19.99 g, 118.3 mmol) in 100 ml POCl₃ was added NEt₃ (15.2 ml) dropwise at 0° C. over a period of 20 min. The thick suspension was warmed to room temperature and then to 80° C. for 3 h with stirring. Then, it was cooled down to room temperature and stirred for an additional 18 h. The mixture was poured into 1.5 l crushed ice, extracted with EtOAc (3×150 ml), dried (Na₂SO₄) and concentrated under reduced pressure. The crude product was filtrated over silica using DCM to obtain the title compound as a yellow oil (19.2 g, 79%). $R_f$ (EtOAc/Hexanes 1:1)=0.55. ¹H-NMR (500 MHz, CDCl₃): δ=8.82 (s, 1H), 7.45 (s, 1H), 3.90 (s, 3H).

Step B: 4,6-Dichloronicotinic acid

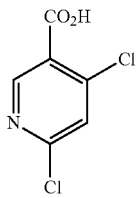

To a solution of methyl 4,6-dichloronicotinate in a mixture of THF (400 ml), MeOH (100 ml) and H₂O (100 ml) was added a solution of NaOH (10 g) in 40 ml H₂O. The mixture was stirred for 40 min, at room temp. Then, the solvents were reduced and it was acidified with conc. HCl to a pH of about 2. It was extracted using a mixture of Et₂O/EtOAc and the organic layer was dried with Na₂SO₄. The solvents were removed and the residue dried in vacuo to obtain the title compound as a white solid (12.3 g, 69%). $R_f$(CHCl₃/MeOH 10:1)=0.85. ¹H-NMR (300 MHz, DMSO-D6): δ=8.80 (s, 1H), 7.90 (s, 1H).

Step C: 4-(4-Bromo-2-chlorophenylamino)-6-chloronicotinic acid

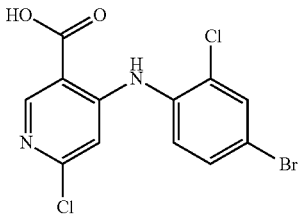

To a solution of 2-chloro-4-bromoaniline (6.776 g, 33.1 mmol) in 50 ml anhydrous THF was added LHMDS (50 ml, 50 mmol, 1M/THF) over a period of 15 min at −78° C. It was stirred for an additional 30 min., then a solution of 4,6-dichloronicotinic acid (3 g, 15.7 mmol) in 50 ml THF was added dropwise. After complete addition the mixture was gradually allowed to warm to room temperature and the reaction mixture was stirred for an additional 12 hours. The mixture was quenched with H₂O and 1N HCl was added (pH 0-1) followed by brine. It was extracted using THF and dried with Na₂SO₄. The solvent was removed and the solid crude product was suspended in 200 ml EtOAc. The suspension was heated with stirring at the reflux temperature for 5 min. It was cooled to room temperature and the precipitate was filtered and washed with EtOAc and dried at 50° C. for 5 h in oil pump vacuo to obtain the title compound as an off-white solid (4.05 g, 72%). $R_f$(CHCl₃/MeOH 10:1)=0.3. ¹H-NMR (500 MHz, DMSO-D6): δ=10.12 (s, 1H), 8.65 (s, 1H), 7.88 (s, 1H), 7.62-7.57 (dd, 1H), 7.55-7.48 (dd, 1H), 6.67 (s, 1H).

Step D: 4-(4-Bromo-2-chlorophenylamino)-5,6-dichloronicotinic acid

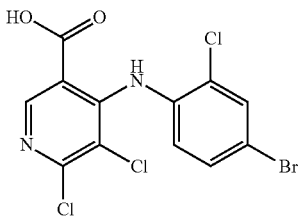

To a thick suspension of 4-(4-bromo-2-chlorophenylamino)-6-chloronicotinic acid (13.25 g, 36.8 mmol) in 350 ml DMF was added NCS (4.94 g, 37 mmol) and the suspension was stirred at room temperature for 3 days. Since the reaction did not go to completion (NMR control), an additional 1.987 g NCS was added and the mixture was stirred for 18 h, upon which the reaction went to completion. The mixture was poured into a solution of 20 g sodium metabisulfite in H₂O (1 l) and the thick suspension was rest for 30 min. It was filtered, and the precipitate was washed with water, then with hexanes and it was dried in oil pump vacuo at 50° C. for 24 hours to obtain the desired compound as a white solid (13.11 g, 90%). ¹H-NMR (500 MHz, DMSO-D6): δ=9.90 (s, br, 1H), 8.63 (s, 1H), 7.74 (s, 1H), 7.43-7.42 (dd, 1H), 6.99-6.97 (dd, 1H).

Step E: Methyl 4-(4-bromo-2-chlorophenylamino)-5,6-dichloronicotinate

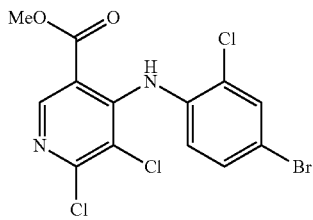

To a suspension of 4-(4-bromo-2-chlorophenylamino)-5,6-dichloronicotinic acid (4.3975 g, 11.2 mmol) in a mixture 70 ml MeOH and 70 ml toluene was added TMS-diazomethane (10 ml, 20 mmol, 2M/hexanes) in small portions at room temperature. At the end of the addition the suspension turned into a solution, and then a precipitate was formed again. The suspension was diluted with hexanes and filtered. And the precipitate was washed with hexanes and dried in vacuo to obtain the title compound 3.03 g (66%).

$R_f$ (EtOAc/Hexanes 1:3)=0.5. ¹H-NMR (500 MHz, DMSO-D6): δ=9.29 (s, 1H), 8.55 (s, 1H), 7.80-7.79 (d, 1H), 7.45-7.40 (dd, 1H), 7.05-7.03 (d, 1H), 3.65 (s, 3H).

Step F: Methyl 6-azido-4-(4-bromo-2-chlorophenylamino)-5-chloronicotinate

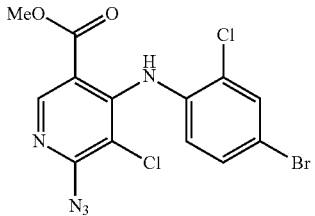

Methyl 4-(4-bromo-2-chlorophenylamino)-5,6-dichloronicotinate (1.690 g, 4.14 mmol) was suspended in 30 ml DMF and the suspension was heated until everything went into solution. It was cooled down to room temperature and to that solution was added solid sodium azide (0.533 g, 8.2 mmol). The yellow solution was stirred for 17 h at room temperature and was diluted with water. The precipitate was filtered, washed with water and hexanes and dried in oil-pump vacuo at 50° C. for 2 h to obtain the title compound as a light-brown solid (1.5422 g, 90%). $^1$H-NMR (300 MHz, DMSO-D6): δ=9.85 (s, 1H), 8.90 (s, 1H), 7.80-7.79 (d, 1H), 7.46-7.40 (dd, 1H), 6.95-6.90 (d, 1H), 3.80 (s, 3H).

Step G: Methyl 6-amino-4-(4-bromo-2-chlorophenylamino)-5-chloronicotinate

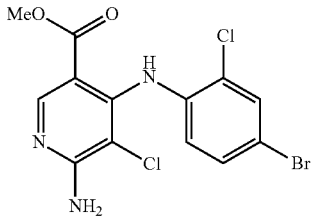

To a suspension of methyl 6-azido-4-(4-bromo-2-chlorophenylamino)-5-chloronicotinate (316 mg, 0.76 mmol) in a mixture of DCM (6 ml) and AcOH (2 ml) was added Zn dust (255 mg, 3.9 mmol) in small portions. After complete addition it was furthers stirred at room temperature for 30 min. Then, the mixture was poured into EtOAc (30 ml), washed with H$_2$O, saturated sodium bicarbonate solution and brine. The organic fractions were dried with Na$_2$SO$_4$ and the solvents were removed and the product was dried in oil-pump vacuo (246 mg, 83%). R$_f$ (CHCl3/MeOH 30:1)=0.3. $^1$H-NMR (500 MHz, DMSO-D6): δ=9.17 (s, 1H), 8.45 (s, 1H), 7.70-7.70 (d, 1H), 7.38-7.36 (dd, 1H), 7.1 (s, 1H, br), 6.68-6.67 (d, 1H), 3.76 (s, 3H).

Step H: Methyl 7-(4-bromo-2-chlorophenylamino)-8-chloroimidazo[1,2-a]pyridine-6-carboxylate

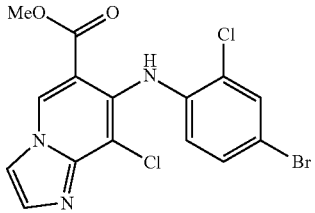

To a suspension of methyl 6-amino-4-(4-bromo-2-chlorophenylamino)-5-chloronicotinate (966 mg, 2.48 mmol) in 13 ml DMF was added chloroacetaldehyde (50% aq. solution, 0.32 ml, 396 mg, 2.52 mmol) and the mixture was heated in a closed vessel to 80° C. for 3 h. The dark solution was cooled to room temperature and the DMF was removed by vacuum distillation. The residue was dissolved in THF and directly purified by column chromatography (EtOAc/hexanes 10:1+ 2% TEA) which delivered the desired product (638 mg, 62%). R$_f$ (EtOAc/Hexanes 10:1)=0.4. $^1$H-NMR (500 MHz, MeOH-D3): δ=9.16 (s, 1H), 7.86-7.85 (d, 1H), 7.54-7.53 (d, 1H), 7.50-7.48 (d, 1H), 7.19-7.17 (dd, 1H), 6.51-6.50 (d, 1H), 3.82 (s, 3H).

Step I: 7-(4-Bromo-2-chlorophenylamino)-8-chloroimidazo[1,2-a]pyridine-6-carboxylic acid

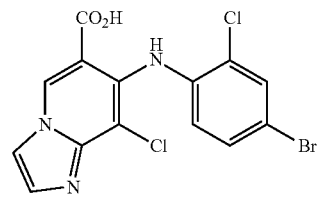

To a solution of methyl 7-(4-bromo-2-chlorophenylamino)-8-chloroimidazo[1,2-a]pyridine-6-carboxylate (366 mg, 0.81 mmol) in a mixture of MeOH (30 ml) and THF (10 ml) was added 10 ml of 1M aq. NaOH solution and the solution was stirred for 18 hours at room temperature. The solvents were reduced in vacuo, and it was extracted using 1M HCl/EtOAc/THF. The organic layers were washed with brine and dried with Na$_2$SO$_4$, and the solvents were removed in vacuo to give the crude product which was used without further purification (200 mg, 62%). $^1$H-NMR (500 MHz, DMSO-D6): δ=9.33 (s, 1H), 8.11 (s, 1H), 7.69-7.68 (d, 1H), 7.35-7.33 (dd, 1H), 6.67-6.65 (d, br, 1H).

Step J: 3-(4-Bromo-2-chlorophenyl)-4-chloro-1H-diimidazo[1,2-a:4',5'-d]pyridin-2(3H)-one

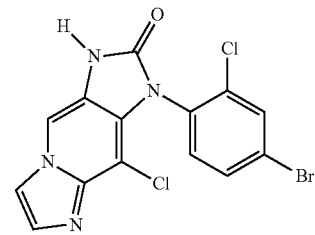

To a suspension of 7-(4-bromo-2-chlorophenylamino)-8-chloroimidazo[1,2-a]pyridine-6-carboxylic acid (152 mg, 0.35 mmol) (HCl salt) in 5 ml EtOAc was added NEt$_3$ (0.14 ml, 102 mg, 1 mmol) and the mixture was stirred for 5 min upon the suspension turned into a solution. The solvents were removed in vacuo and the residue was dried in oil-pump vacuo. This residue was suspended in 4.5 ml anhydrous toluene and it was ultrasonicated for 1 min. DPPA (0.1 ml, 124 mg, 0.44 mmol) was added and the suspension was heated with stirring under argon at 125° C. oil bath temperature to reflux for 5 h. The initial suspension turns into a dark solution after about 30 min. heating, and then a precipitate is formed after about another 30 min. reaction time. After 5 h the reaction mixture was cooled to room temperature and the volatiles were removed in vacuo. To the dark residue was washed with Et₂O (ultrasonication) and again dried in oil pump vacuo. The crude product was used without purification for the next step in the same reaction vessel. R$_f$(CHCl₃/MeOH 4:1)=0.5

Step K: 3-(4-bromo-2-chlorophenyl)-4-chloro-1-(cyclopropylsulfonyl)-1H-diimidazo[1,2-a:4',5'-d]pyridin-2(3H)-one

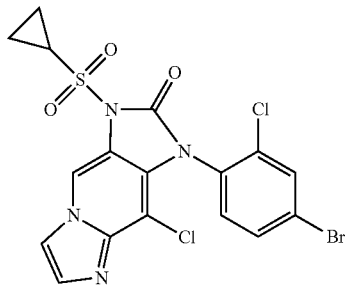

To a solution of the crude product (Step J) in 3 ml anhydrous THF was added LHMDS (0.4 ml, 0.4 mmol, 1M/THF) at 0° C. and the mixture was stirred for 5 min. The cyclopropyl sulfonamide (83 mg, 0.59 mol) was added neat and the mixture was warmed to room temperature and stirred for 15 h. The mixture was quenched with brine, diluted with H₂O and extracted using a mixture of EtOAc/THF (3:1). The organic phase was washed with brine and dried with Na₂SO₄. Subsequent column chromatography (100% EtOAc) gave the title product as a brown oil (36 mg, 20% over the 2 last steps). R$_f$ (100% EtOAc)=0.35. ¹H-NMR (500 MHz, MeOH-D3): δ=8.80 (s, 1H), 7.89 (s, 1H), 7.86-7.85 (d, 1H), 7.68-7.66 (dd, 1H), 7.60-7.58 (d, 1H), 7.46 (s, 1H), 1.51-1.37 (m, 2H), 1.23-1.15 (m, 2H).

Step L: N-(7-(4-bromo-2-chlorophenylamino)-8-chloroimidazo[1,2-a]pyridin-6-yl)cyclopropanesulfonamide

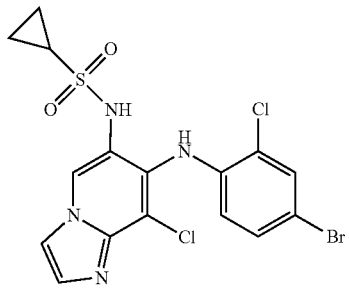

To a solution of N-(7-(4-bromo-2-chlorophenylamino)-8-chloroimidazo[1,2-a]pyridin-6-yl)cyclopropanesulfonamide (25 mg, 0.05 mmol) was added solid KOTMS (21 mg, 0.16 mmol) and the cloudy solution was stirred at 40° C. for 2.5 h. It was quenched with aqueous NH₄Cl, extracted with EtOAc and dried with Na₂SO₄. The crude product was purified by column chromatography (CHCl₃/MeOH 20:1) to give the title compound as a brown paste (11 mg, 47%). R$_f$(CHCl₃/MeOH 15:1)=0.25. ¹H-NMR (500 MHz, CDCl₃): δ=8.46 (s, 1H), 7.70 (s, 1H), 7.66 (s, 1H), 7.56-7.55 (s, 1H), 7.18-7.16 (dd, 1H), 6.30-6.29 (d, 1H), 6.45 (s, br, 1H), 6.10 (s, br, 1H), 2.43-2.39 (m, 1H), 1.13-1.10 (m, 2H), 1.00-0.93 (m, 2H).

Example 10

N-(7-(4-bromo-2-chlorophenylamino)-8-chloroimidazo[1,2-a]pyridin-6-yl)-1-(2-hydroxyethyl)cyclopropane-1-sulfonamide

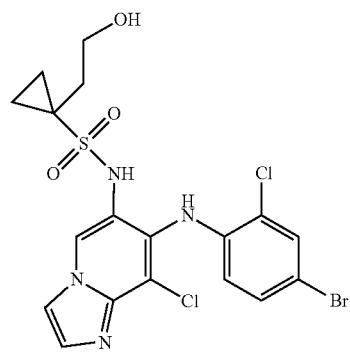

This compound was synthesized from 3-(4-bromo-2-chlorophenyl)-4-chloro-1-(cyclopropylsulfonyl)-1H-diimidazo[1,2-a:4',5'-d]pyridin-2(3H)-one (see example 9) according to example 4 (step A, B and C). ¹H NMR (400 MHz, MeOD) δ ppm 0.87-0.98 (m, 2H) 1.11-1.24 (m, 2H) 1.99-2.13 (m, 2H) 3.35 (s, 2H) 3.71 (s, 3H) 6.46 (d, J=8.71 Hz, 1H) 7.24 (d, J=2.28 Hz, 1H) 7.54-7.67 (m, 1H) 7.95 (d, J=1.45 Hz, 1H) 8.70 (s, 1H). m/z=519 [M−1]⁻.

Example 11

N-(8-chloro-7-(2-fluoro-4-iodophenylamino)imidazo[1,2-a]pyridin-6-yl)cyclopropanesulfonamide

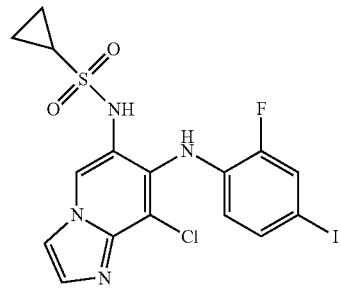

This compound is synthesized from methyl 6-amino-5-chloro-4-(2-fluoro-4-iodophenylamino)nicotinate: (see below) according to example 9 (step H through L).

Methyl 6-amino-5-chloro-4-(2-fluoro-4-iodophenylamino)nicotinate

Step A:
6-Dichloro-4-(2-fluoro-4-iodophenylamino)nicotinic acid

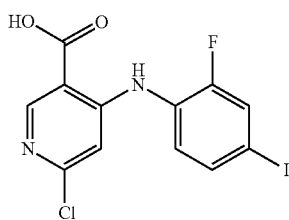

To a solution of 2-fluoro-4-iodoaniline (11.3 g, 50.3 mmol) in 85 ml anhydrous THF is added LiHMDS (83 ml, 83 mmol, 1M/THF) over a period of 30 min at −78° C. It is stirred for another 30 min, then a solution of methyl 4,6-dichloronicotinate (step B, example 9) (5.00 g, 26.2 mmol) in 85 ml THF is added dropwise. After complete addition the mixture is gradually allowed to warm to room temperature and stirred for another 18 hrs. It is quenched with $H_2O$, then 1N HCl is added to (pH=1) followed by brine. It is extracted using THF and dried with $Na_2SO_4$. The solvents are removed and the crude solid is suspended in 300 ml of EtOAc. The suspension is heated with stirring at the reflux temperature for 5 min. It is cooled to room temperature and the precipitate is filtered and washed with EtOAc and dried at 50° C. for 5 h in oil pump vacuo.

Step B: 5,6-Dichloro-4-(2-fluoro-4-iodophenylamino)nicotinic acid

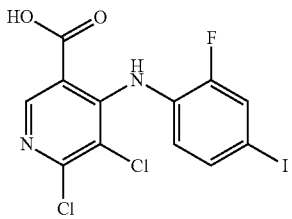

This compound is synthesized from 6-dichloro-4-(2-fluoro-4-iodophenylamino)nicotinic acid (8.1 g, 23.5 mmol) according to example 9, step D. The title compound is obtained.

Step C: Methyl 5,6-dichloro-4-(2-fluoro-4-iodophenylamino)nicotinate

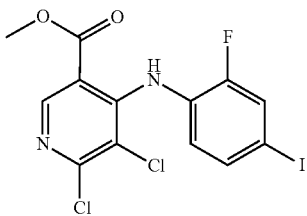

This compound is synthesized from 5,6-dichloro-4-(2-fluoro-4-iodophenylamino)nicotinic acid (3.00 g, 7.64 mmol) according to example 9, step E.

Step D: Methyl 6-azido-5-chloro-4-(2-fluoro-4-iodophenylamino)nicotinate

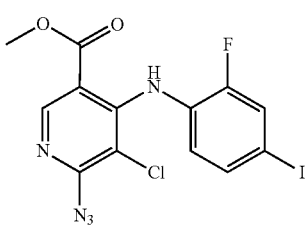

This compound is synthesized from methyl 5,6-dichloro-4-(2-fluoro-4-iodophenylamino)nicotinate (2.9 g, 6.5 mmol) according to example 9, step F.

Step E: Methyl 6-amino-5-chloro-4-(2-fluoro-4-iodophenylamino)nicotinate

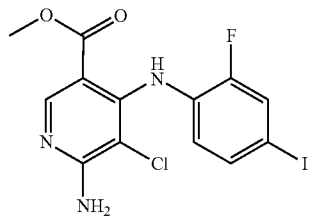

This compound is synthesized from methyl 6-azido-5-chloro-4-(2-fluoro-4-iodophenylamino)nicotinate (2.65 g, 5.9 mmol) according to example 9, step G.

Example 12

N-(8-chloro-7-(2-fluoro-4-iodophenylamino)imidazo[1,2-a]pyridin-6-yl)-1-(2-hydroxyethyl)cyclopropane-1-sulfonamide

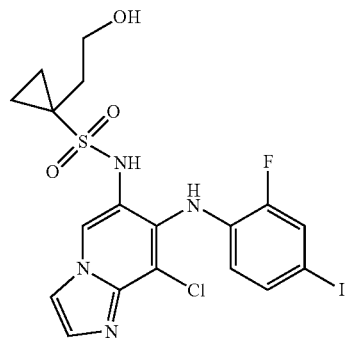

This compound was synthesized according to example 4 (step A, B and C) starting from 4-chloro-3-(2-fluoro-4-iodophenyl)-1H-diimidazo[1,2-a:4',5'-d]pyridin-2(3H)-one (Example 10). m/z=549 [M−1]⁻. $^1H$ NMR (400 MHz, MeOD) δ ppm 0.85-0.96 (m, 2H) 1.12-1.24 (m, 2H) 2.02 (t, J=6.63 Hz, 2H) 3.69 (t, J=6.63 Hz, 2 H) 6.43 (t, J=8.71 Hz, 1H) 7.32 (d, J=8.50 Hz, 1H) 7.47 (dd, J=10.68, 1.76 Hz, 1H) 7.60 (s, 1H) 7.93 (s, 1H) 8.65 (s, 1H).

Example 13

N-(8-fluoro-7-(2-fluoro-4-iodophenylamino)imidazo[1,2-a]pyridin-6-yl)cyclopropanesulfonamide

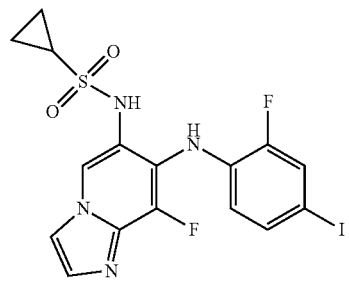

This compound is synthesized according to example 9 (step H through L) starting from methyl 6-amino-5-fluoro-4-(2-fluoro-4-iodophenylamino)nicotinate (see below).

Methyl 6-amino-5-fluoro-4-(2-fluoro-4-iodophenylamino)nicotinate

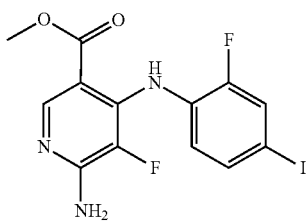

To a solution of methyl 6-amino-5-chloro-4-(2-fluoro-4-iodophenylamino)nicotinate (2.0 g, 4.74 mmol) (Example 11, step E) in a mixture of MeOH/water (1/1) (20 ml) is added select fluor (1.6 g, 4.74 mmol). The mixture is stirred at room temperature overnight, diluted with EtOAc and washed with 0.5 N HCl and brine. The organic extracts are dried ($Na_2SO_4$) and concentrated under reduced pressure. The crude material was purified by HPLC (reverse phase) to obtain the title compound.

Example 14

N-(7-(2-fluoro-4-iodophenylamino)-8-methylimidazo[1,2-a]pyridin-6-yl)cyclopropanesulfonamide

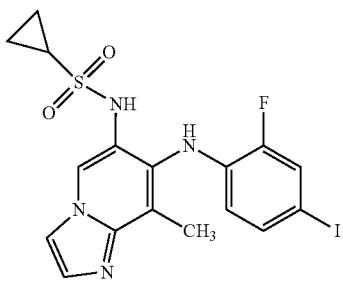

This compound was synthesized according to example 9 (step C through L) starting from methyl 4,6-dichloro-5-methylnicotinate (Journal of Heterocyclic Chemistry (1999), 36(4), 953-957). m/z=485 [M−1]⁻. ¹H NMR (DMSO-$d_6$, 400 MHz): δ 0.69 (m, 2H), 0.85 (m, 2H), 2.23 (s, 3H), 2.48 (m, 1H), 6.22 (m, 1H), 6.53 (m, 1H), 7.22 (d, 1H), 7.45 (m, 1H), 7.55 (m, 2H), 8.00 (s, 1H), 8.56 (s, 1H).

Example 15

N-(7-(2-fluoro-4-iodophenylamino)-8-methylimidazo[1,2-a]pyridin-6-yl)-1-(2-hydroxyethyl)cyclopropane-1-sulfonamide

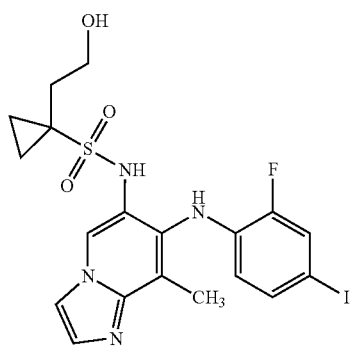

This compound is synthesized according to example 4 (step A, B and C) starting from 3-(2-fluoro-4-iodophenyl)-4-methyl-1H-diimidazo[1,2-a:4',5'-d]pyridin-2(3H)-one.

Example 16

1-(2,3-dihydroxypropyl)-N-(7-(2-fluoro-4-iodophenylamino)-8-methylimidazo[1,2-a]pyridin-6-yl)cyclopropane-1-sulfonamide

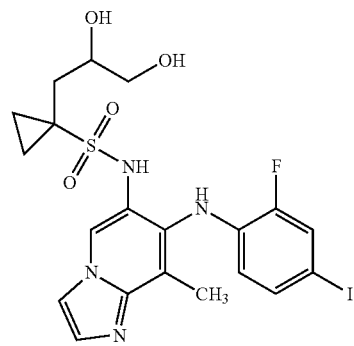

This compound was synthesized according to example 5 (step A, B and C) starting from 3-(2-fluoro-4-iodophenyl)-4-methyl-1H-diimidazo[1,2-a:4',5'-d]pyridin-2(3H)-one.
m/z=559 [M−1]⁻. ¹H NMR (DMSO-$d_6$, 400 MHz): δ 0.97 (m, 4H), 1.60 (m, 1H), 2.08 (m, 1H), 2.24 (s, 3H), 3.28 (m, 2H), 3.54 (m, 1H), 4.53 (m, 2H), 6.16 (m, 1H), 7.24 (m, 1H), 7.38 (s, 1H), 7.54 (s, 2H), 7.97 (s, 1H), 8.57 (s, 1H), 9.34 (s, 1H).

Example 17

N-(7-(4-bromo-2-chlorophenylamino)-8-methylimidazo[1,2-a]pyridin-6-yl)cyclopropanesulfonamide

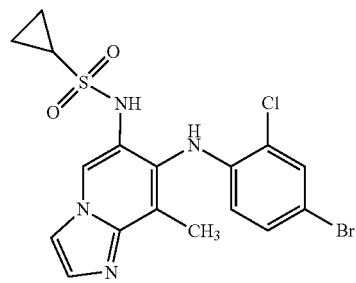

This compound was synthesized according to example 9 (step C through L) starting from methyl 4,6-dichloro-5-methylnicotinate (Journal of Heterocyclic Chemistry (1999), 36(4), 953-957) m/z=454 [M−1]⁻. ¹H NMR (DMSO-$d_6$, 400 MHz): δ 0.78 (m, 2H), 0.86 (m, 2H), 2.22 (s, 3H), 6.29 (d, J=8 Hz, 1H), 7.22 (d, J=8 Hz, 1H), 7.31 (s, 1H), 7.56 (s, 1H), 7.64 (s, 1H), 8.01 (s, 1H), 8.60 (s, 1H), 9.34 (s, 1H).

Example 18

N-(7-(4-bromo-2-chlorophenylamino)-8-methylimidazo[1,2-a]pyridin-6-yl)-1-(2-hydroxyethyl)cyclopropane-1-sulfonamide

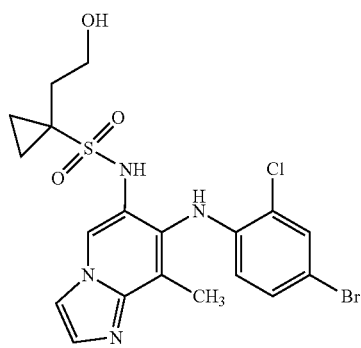

This compound was synthesized according to example 4 (step A, B and C) starting from 3-(4-bromo-2-chlorophenyl)-4-methyl-1H-diimidazo[1,2-a:4',5'-d]pyridin-2(3H)-one. m/z=499 [M−1]⁻. $^1$H NMR (DMSO-d$_6$, 400 MHz): δ 0.88 (m, 4H), 1.94 (m, 2H), 2.24 (s, 3H), 3.48 (m, 2H), 4.54 (m, 1H), 6.30 (d, J=8 Hz, 1H), 7.29 (d, J=8 Hz, 1H), 7.37 (s, 1H), 7.59 (s, 1H), 8.03 (s, 1H), 8.61 (s, 1H), 9.35 (s, 1H).

Example 19

N-(8-chloro-7-(2-fluoro-4-iodophenylamino)-3-methyl-[1,2,4]diazole[4,3-a]pyridin-6-yl)cyclopropanesulfonamide

Step A: 5-chloro-4-(2-fluoro-4-iodophenylamino)hydrazinylnicotinic acid

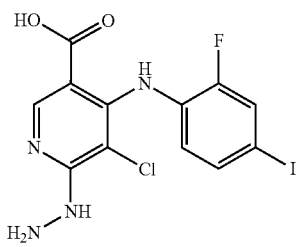

Hydrazine monohydrate (0.2 ml, 4.12 mmol) is added to a solution of methyl 6-amino-5-chloro-4-(2-fluoro-4-iodophenylamino)nicotinate (example 10, step A, B and C) (2 g, 4.5 mmol) in N,N-dimethylacetamide (2.00 ml). After stirring at 90° C. for 1 h, the reaction mixture is cooled to room temperature and diluted with EtOAc. The organic layer is washed with H$_2$O, brine, dried with Na$_2$SO$_4$ and concentrated under reduced pressure. The crude material is washed with DCM to obtain the title material.

Step B: 8-Chloro-7-(2-fluoro-4-iodophenylamino)-3-methyl-[1,2,4]triazolo[4,3-a]pyridine-6-carboxylic acid

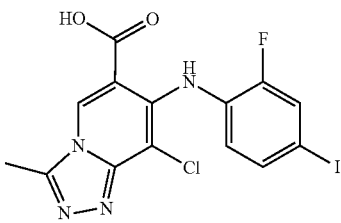

Acetic anhydride (0.95 mmol) is added to a solution of 5-chloro-4-(2-fluoro-4-iodophenylamino)-6-hydrazinylnicotinic acid (0.4 g, 0.95 mmol) and triethylamine (1.9 mmol) in DCM (10 ml) at 0° C. The reaction mixture is warmed to room temperature, stirred for an additional 10 min and POCl$_3$ (0.95 mmol) is added. After stirring overnight at room temperature the mixture is refluxed for 3 days. It was diluted with EtOAc and NaHCO$_3$ and stirred for 20 min. The organic layer is washed with H$_2$O, brine, dried with Na$_2$SO$_4$ and concentrated under reduced pressure. The crude product is purified by column chromatography.

Step C: 9-chloro-8-(2-fluoro-4-iodophenyl)-3-methyl-6H-imidazo[4,5-d][1,2,4]triazolo[4,3-a]pyridin-7(8H)-one

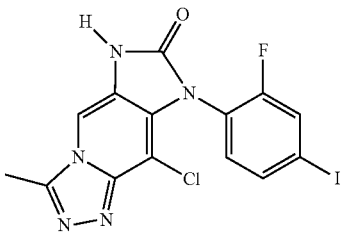

Synthesize according to example 3, step H from 9-chloro-8-(2-fluoro-4-iodophenyl)-3-methyl-6H-imidazo[4,5-d][1,2,4]triazolo[4,3-a]pyridin-7(8H)-one (0.34, 0.76 mmol) to afford the title compound.

Step D: 9-chloro-6-(cyclopropylsulfonyl)-8-(2-fluoro-4-iodophenyl)-3-methyl-6H-imidazo[4,5-d][1,2,4]triazolo[4,3-a]pyridin-7(8H)-one

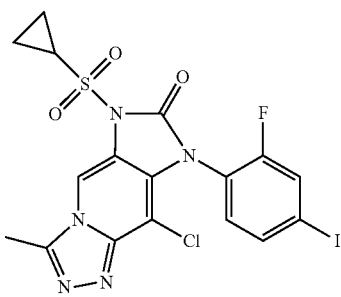

Synthesize according to example 3, step I from 9-chloro-8-(2-fluoro-4-iodophenyl)-3-methyl-6H-imidazo[4,5-d][1,2,4]triazolo[4,3-a]pyridin-7(8H)-one (100 mg, 0.22 mmol) to afford the title compound.

Step E: N-(8-chloro-7-(2-fluoro-4-iodophenylamino)-3-methyl-[1,2,4]triazolo[4,3-a]pyridin-6-yl)cyclopropanesulfonamide

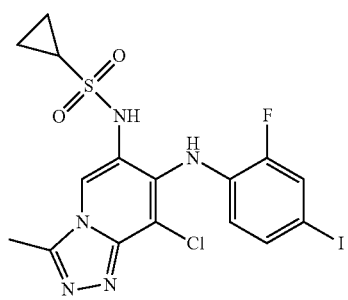

Synthesize according to example 3, step J from 9-chloro-6-(cyclopropylsulfonyl)-8-(2-fluoro-4-iodophenyl)-3-methyl-6H-imidazo[4,5-d][1,2,4]triazolo[4,3-a]pyridin-7(8H)-one (98 mg, 018 mmol) to afford the title compound.

Example 20

N-(8-chloro-7-(2-fluoro-4-iodophenylamino)-3-methyl-[1,2,4]triazolo[4,3-a]pyridin-6-yl)-1-(2-hydroxyethyl)cyclopropane-1-sulfonamide

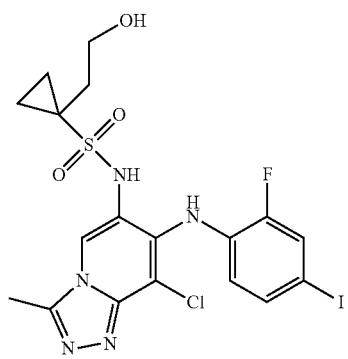

Synthesize according to example 4, step A, B and C from 9-chloro-8-(2-fluoro-4-iodophenyl)-3-methyl-6H-imidazo[4,5-d][1,2,4]triazolo[4,3-a]pyridin-7(8H)-one to afford the title compound.

Example 21

N-(7-chloro-6-(2-fluoro-4-iodophenylamino)-3-methyl-3a,7a-dihydro-3H-imidazo[4,5-b]pyridin-5-yl)cyclopropanesulfonamide Step A: 7-Chloro-6-(2-fluoro-4-iodophenylamino)-3-methyl-3H-imidazo[4,5-b]pyridine-5-carboxylic acid

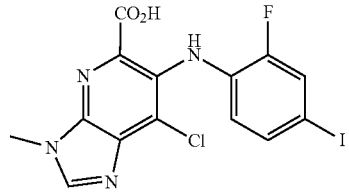

To a solution of 2-fluoro-4-iodo-aniline (2.9 g, 22.1 mmol) in THF (20 ml) at −78° C. is added LiHMDS (33.3 ml, 1 M in THF, 33.3 mmol) dropwise. The reaction mixture is stirred for 10 min and a solution of 6-bromo-7-chloro-3-methyl-3H-imidazo[4,5-b]pyridine-5-carboxylic acid (WO 2005/051906) (5.63 g, 10.1 mmol) in THF (30 ml) is added to the mixture. The reaction is slowly warmed to room temperature and stirred at this temperature for 16 h. The mixture is concentrated, quenched with 10% HCl solution (70 ml), and extracted with EtOAc (2×200 ml). The combined organic solution is dried over MgSO$_4$ and concentrated to dryness. Purification by trituration with boiling CH$_2$Cl$_2$ gives the title compound.

Step B: 8-Chloro-1-(2-fluoro-4-iodophenyl)-5-methyl-3,5-dihydrodiimidazo[4,5-b:4',5'-e]pyridin-2(1H)-one

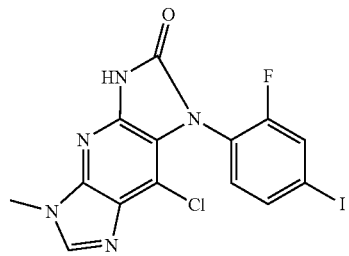

To a suspension of 7-chloro-6-(2-fluoro-4-iodophenylamino)-3-methyl-3H-imidazo[4,5-b]pyridine-5-carboxylic acid (2.75 g, 6.16 mmol) in toluene (80 ml) is added triethylamine (2.57 ml, 18.5 mmol) and diphenylphosphoryl azide (1.56 ml, 7.7 mmol). The reaction is heated at reflux for 4 h. The mixture is cooled to room temperature and concentrated to dryness. Silica gel chromatography yields the title compound.

Step C: 8-Chloro-3-(cyclopropylsulfonyl)-1-(2-fluoro-4-iodophenyl)-5-methyl-3,4a,5,7a-tetrahydrodiimidazo[4,5-b:4',5'-e]pyridin-2(1H)-one

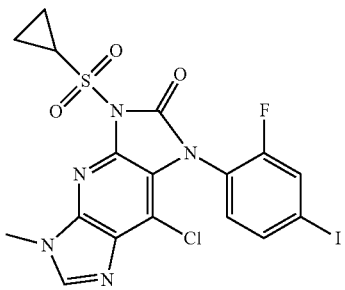

To a solution of 8-chloro-1-(2-fluoro-4-iodophenyl)-5-methyl-3,5-dihydrodiimidazo[4,5-b:4',5'-e]pyridin-2(1H)-one (200 mg, 0.36 mmol) in THF (6 ml) at −78° C. is added LiHMDS (0.54 ml, 1 M in THF, 0.54 mmol). The reaction mixture is stirred at −78° C. for 10 min and cyclopropylsulfonyl chloride (100 mg, 0.72 mmol) is added to the mixture. The reaction is slowly warmed to room temperature and stirred at the temperature for 3 h. The reaction is quenched with saturated aqueous NH$_4$Cl solution (10 ml) and extracted with EtOAc (2×10 ml). The combined organic solution is washed with brine (10 ml), dried over MgSO$_4$ and concentrated. Silica gel chromatography yields the title compound.

Step D: N-(7-Chloro-6-(2-fluoro-4-iodophenylamino)-3-methyl-3a,7a-dihydro-3H-imidazo[4,5-b]pyridin-5-yl)cyclopropanesulfonamide

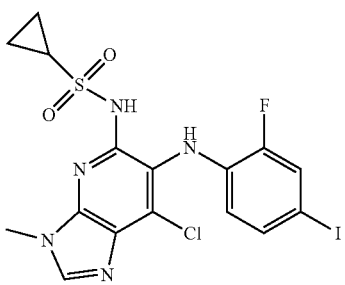

To a solution of 8-chloro-3-(cyclopropylsulfonyl)-1-(2-fluoro-4-iodophenyl)-5-methyl-3,4a,5,7a-tetrahydrodiimidazo[4,5-b:4',5'-e]pyridin-2(1H)-one (79 mg, 0.144 mmol) in THF (5 ml) is added potassium trimethylsilanolate (55 mg, 0.43 mmol). The reaction is stirred at room temperature for 16 h, quenched with saturated aqueous NH$_4$Cl solution (10 ml) and extracted with EtOAc (2×10 ml). The combined organic solution is washed with brine (10 ml), dried over MgSO$_4$ and concentrated. Silica gel chromatography yields the title compound.

Example 22

N-(7-chloro-6-(2-fluoro-4-iodophenylamino)-3-methyl-3a,7a-dihydro-3H-imidazo[4,5-b]pyridin-5-yl)-1-(2-hydroxyethyl)cyclopropane-1-sulfonamide

Step A: 3-(1-(2-(Tert-butyldimethylsilyloxy)ethyl)cyclopropylsulfonyl)-8-chloro-1-(2-fluoro-4-iodophenyl)-5-methyl-3,4a,5,7a-tetrahydrodiimidazo[4,5-b:4',5'-e]pyridin-2(1H)-one

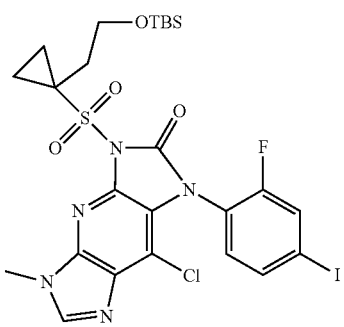

To a solution of 8-chloro-1-(2-fluoro-4-iodophenyl)-5-methyl-3,5-dihydrodiimidazo[4,5-b:4',5'-e]pyridin-2(1H)-one (example 16, step B) (150 mg, 0.35 mmol) in THF (5 ml) at −78° C. is added LiHMDS (0.39 ml, 1 M in THF, 0.39 mmol). The reaction mixture is stirred at −78° C. for 30 min and 1-(2-(tert-butyldimethylsilyloxy)ethyl)cyclopropane-1-sulfonyl chloride (144 mg, 0.48 mmol) is added to the mixture. The reaction is slowly warmed to room temperature and stirred at the temperature for 16 h. The reaction is quenched with saturated aqueous NH$_4$Cl solution (20 ml) and extracted with EtOAc (2×30 ml). The combined organic solution is washed with brine (30 ml), dried over MgSO$_4$ and concentrated. Silica gel chromatography yields the desired product.

Step B: 1-(2-(Tert-butyldimethylsilyloxy)ethyl)-N-(7-chloro-6-(2-fluoro-4-iodophenylamino)-3-methyl-3a,7a-dihydro-3H-imidazo[4,5-b]pyridin-5-yl)cyclopropane-1-sulfonamide

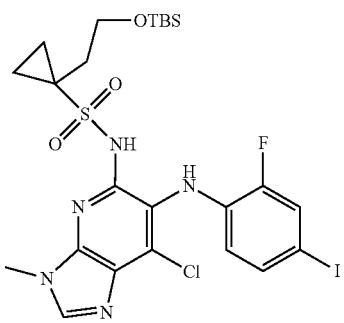

To a solution of 3-(1-(2-(tert-butyldimethylsilyloxy)ethyl)cyclopropylsulfonyl)-8-chloro-1-(2-fluoro-4-iodophenyl)-5-methyl-3,4a,5,7a-tetrahydrodiimidazo[4,5-b:4',5'-e]pyridin-2(1H)-one (86 mg, 0.124 mmol) in THF (5 ml) is added potassium trimethylsilanolate (80 mg, 0.62 mmol). The resulting solution is stirred at room temperature for 24 h. The reaction is quenched with saturated aqueous NH₄Cl solution (10 ml) and extracted with EtOAc (2×10 ml). The combined organic solution is washed with brine (10 ml), dried over MgSO₄ and concentrated. Silica gel chromatography yields the desired product.

Step C: N-(7-chloro-6-(2-fluoro-4-iodophenylamino)-3-methyl-3a,7a-dihydro-3H-imidazo[4,5-b]pyridin-5-yl)-1-(2-hydroxyethyl)cyclopropane-1-sulfonamide

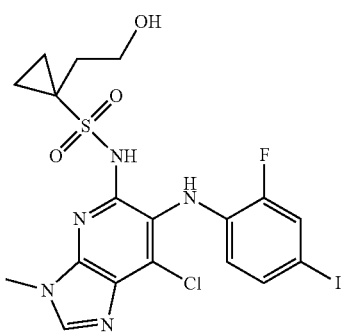

To a solution of 1-(2-(tert-butyldimethylsilyloxy)ethyl)-N-(7-chloro-6-(2-fluoro-4-iodophenylamino)-3-methyl-3a,7a-dihydro-3H-imidazo[4,5-b]pyridin-5-yl)cyclopropane-1-sulfonamide (40 mg, 0.060 mmol) in THF (2 ml) is added HCl (0.20 ml, 1.2 N in H₂O, 0.24 mmol). After stirring for 1 h, the reaction is quenched with saturated aqueous NaHCO₃ solution (3 ml) and extracted with EtOAc (2×10 ml). The combined organic solution is dried over Na₂SO₄ and concentrated. Silica gel chromatography yields the title compound.

Example 23

N-(7-(4-bromo-2-fluorophenylamino)imidazo[1,2-b]pyridazin-6-yl)cyclopropanesulfonamide Step A: Preparation of 4,6-dichloro-pyridazine-3-carboxylic acid

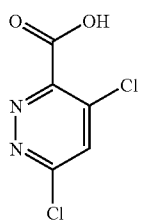

To a solution of methyl 4,6-dichloro-pyridazine-3-carboxylate (6.01 g, 29.03 mmol, WO 2004/031174) in THF (29 ml) at 0° C. is added 29 ml of aqueous 1.0 M LiOH with stirring. The resulted mixture is stirred continuously at 0° C. for 40 min and monitored by TLC. The reaction mixture is diluted with water, and acidified to pH 1-2 with aqueous 1.0 M HCl. The crude product is suspended between the organic and aqueous layers. After filtration and washed with water and hexane, and dried under vacuum, the product is obtained.

Step B: 4-(4-Bromo-2-fluoro-phenylamino)-6-chloro-pyridazine-3-carboxylic acid

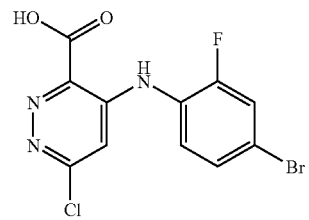

To the stirred solution of 4-bromo-2-fluorophenylamine (3.15 g, 16.58 mmol) in THF (50 ml) under argon at −78° C. is added dropwise LiHMDS (24.9 ml, 24.9 mmol, 1.0 M in hexane). After stirring for one hour at −78° C., a solution of 4,6-dichloropyridazine-3-carboxylic acid (1.6 g, 8.29 mmol) in THF (10 ml) is added dropwise. The resulting mixture is allowed to warm to room temperature slowly and was stirred continuously for 18 hours. The reaction is quenched by addition of 5 ml of water, diluted with ethyl acetate, acidified with aqueous 1.0 M HCl to pH 1-2. The layers are separated and aqueous layer is extracted with ethyl acetate (30 ml×3). The combined organic layers are washed with brine (30 ml×3), dried over Na₂SO₄, and concentrated under reduced pressure. The residue is purified by flash column chromatography to give the product.

Step C: 4-(4-Bromo-2-fluoro-phenylamino)-6-chloro-pyridazine-3-carboxylic acid tert-butyl ester

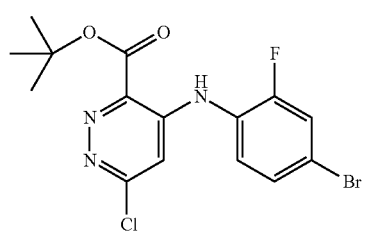

To the stirred solution of 4-(4-bromo-2-fluoro-phenylamino)-6-chloro-pyridazine-3-carboxylic acid (516 gm, 1.49 mmol) in THF (10 ml) under argon at room temperature is added a solution of 2-tert-butyl-1,3-diisopropylisourea (1.49 g, 7.45 mmol) in THF (1.0 ml). The resulted mixture is refluxed for 6 hours. The reaction mixture is then cooled to room temperature and diluted with ethyl acetate. The organic layer is washed with 10% K₂CO₃ (20 ml×2) and saturated NaCl (30 ml×3), dried over Na₂SO₄ and concentrated in vacuum. The residue is dissolved in 30 ml of dichloromethane and the resulting white solid (urea byproduct) is filtered out. The filtrate is concentrated under reduced pressure. The residue is purified by flash column chromatography to provide the desired product.

Step D: 6-Azido-4-(4-Bromo-2-fluoro-phenylamino)-pyridazine-3-carboxylic acid tert-butyl ester

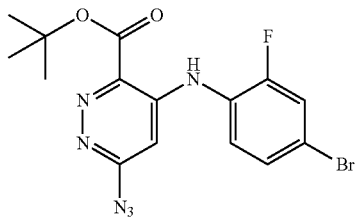

To a solution of 4-(4-bromo-2-fluoro-phenylamino)-6-chloro-pyridazine-3-carboxylic acid tert-butyl ester (300 mg, 034 mmol) in DMF (5 ml) under argon at room temperature is added sodium azide (96 mg, 1.48 mmol) with stirring. The reaction mixture is stirred at 50° C. for 6 hours. After cooling to room temperature, the reaction mixture is diluted with ethyl acetate and washed with water, saturated NaHCO₃ (20 ml×3) and saturated NaCl (30 ml×3). The organic layer is dried over Na₂SO₄ and concentrated. The residue is purified by flash column chromatography to provide the desired product.

Step E: 6-Amino-4-(4-Bromo-2-fluoro-phenylamino)-6-chloro-pyridazine-3-carboxylic acid tert-butyl ester

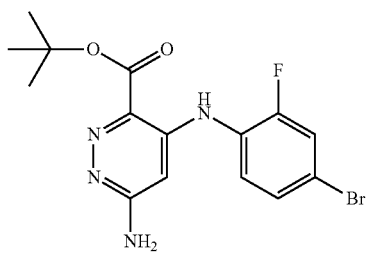

To the stirred solution of 6-azido-4-(4-bromo-2-fluoro-phenylamino)-6-chloro-pyridazine-3-carboxylic acid tert-butyl ester (122 mg, 0.30 mmol) in 5 ml of mixed solvents (3:1 v/v, dichloromethane/acetic acid) is added zinc powder (98 mg, 1.5 mmol) at room temperature. After three hours, the reaction mixture is poured into ethyl acetate (50 ml). The organic layer is washed with water, saturated NaHCO₃ (30 ml×3) and saturated NaCl (30 ml×3). The organic layer is dried over Na₂SO₄, and concentrated. The residue is purified by flash column chromatography to provide the desired product.

Step F: 7-(4-Bromo-2-fluoro-phenylamino)-imidazo[1,2-b]pyridazine-6-carboxylic acid

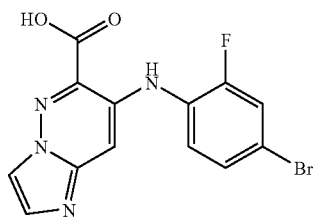

To a suspended solution of 6-amino-4-(4-bromo-2-fluoro-phenylamino)-6-chloro-pyridazine-3-carboxylic acid tert-butyl ester (61 mg, 0.16 mmol) in ethanol (5 ml) in a bomb reactor is added at room temperature chloroacetaldehyde (0.12 ml of 50% aqueous solution, 5.0 equivalents). The reaction mixture is sealed and stirred at 80° C. for two days, and then cooled to room temperature. The solvent is removed, and the residue is diluted with ethyl acetate (20 ml). The organic layer is washed with saturated NaCl (20 ml×3), dried over Na₂SO₄, and concentrated. The residue is purified by flash column chromatography to provide the desired product.

Step G: 1-(4-Bromo-2-fluoro-phenyl)-1H,3H-1,3,4,4a,7-pentaaza-s-indacen-2-one

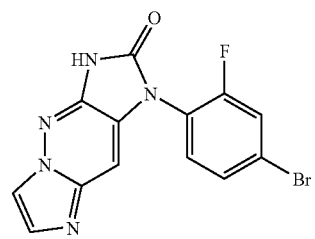

Synthesize according to example 21, step B from 7-(4-bromo-2-fluoro-phenylamino)-imidazo[1,2-b]pyridazine-6-carboxylic acid to afford the title compound.

Step H: 1-(4-Bromo-2-fluoro-phenyl)-3-(butane-2-sulfonyl)-1H,3H-1,3,4,4a,7-pentaaza-s-indacen-2-one

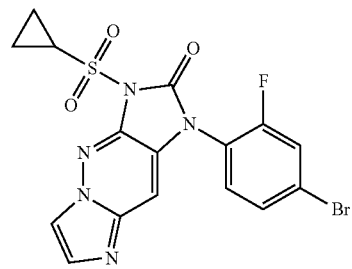

Synthesize according to example 21, step C from 1-(4-bromo-2-fluoro-phenyl)-1H,3H-1,3,4,4a,7-pentaaza-s-indacen-2-one to afford the title compound.

Step I: Cyclopropanesulfonic acid [7-(4-bromo-2-fluoro-phenylamino)-imidazo[1,2-b]pyridazin-6-yl]-amide

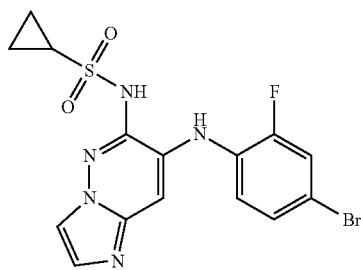

Synthesize according to example 4, step D from 1-(4-bromo-2-fluoro-phenyl)-3-(butane-2-sulfonyl)-1H,3H-1,3,4,4a,7-pentaaza-s-indacen-2-one to afford the title compound.

Example 24

N-(7-(4-bromo-2-fluorophenylamino)imidazo[1,2-b]pyridazin-6-yl)-1-(2-hydroxyethyl)cyclopropane-1-sulfonamide

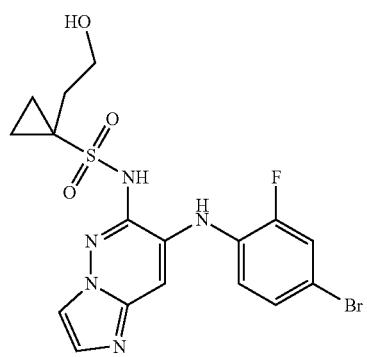

Synthesize according to example 22, step A, B and C from 1-(4-bromo-2-fluoro-phenyl)-1H,3H-1,3,4,4a,7-pentaaza-s-indacen-2-one to afford the title compound.

Example 25

N-(7-fluoro-6-(2-fluoro-4-iodophenylamino)pyrazolo[1,5-a]pyrimidin-5-yl)cyclopropanesulfonamide

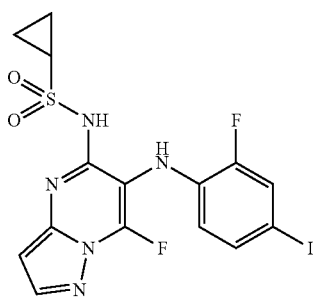

This compound is synthesized according to example 21 (step A through D) starting from 6-chloro-7-fluoropyrazolo[1,5-a]pyrimidine-5-carboxylic acid (WO 2005/051906).

Example 26

N-(7-fluoro-6-(2-fluoro-4-iodophenylamino)pyrazolo[1,5-a]pyrimidin-5-yl)-1-(2-hydroxyethyl)cyclopropane-1-sulfonamide

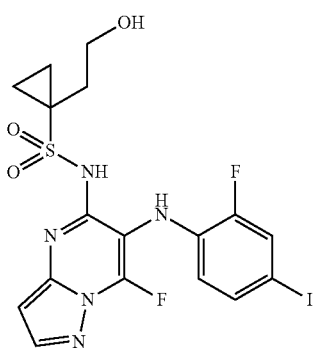

This compound is synthesized according to example 22 (step A through C) starting from 3-(cyclopropylsulfonyl)-9-fluoro-1-(2-fluoro-4-iodophenyl)-1H-pyrazolo[1,5-a]purin-2(3H)-one (example 25).

Example 27

N-(6-(4-bromo-2-fluorophenylamino)-7-fluoro-3-methylisoxazolo[4,5-b]pyridin-5-yl)cyclopropane-sulfonamide

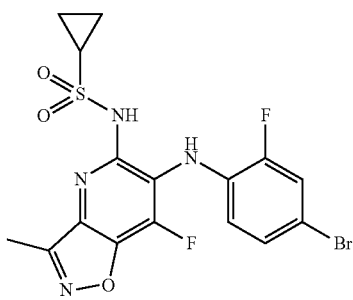

This compound is synthesized according to example 4 (step B through D) starting from 6-(4-bromo-2-fluorophenylamino)-7-fluoro-3-methylisoxazolo[4,5-b]pyridine-5-carboxylic acid (WO 2005/051906).

Example 28

N-(6-(4-bromo-2-fluorophenylamino)-7-fluoro-3-methylisoxazolo[4,5-b]pyridin-5-yl)-1-(2-hydroxyethyl)cyclopropane-sulfonamide

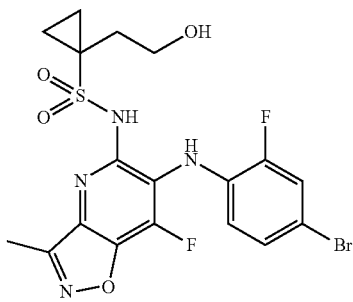

This compound is synthesized according to example 4 (step A through C) starting from 7-(4-bromo-2-fluorophenyl)-8-fluoro-3-methyl-5H-imidazo[4,5-e]isoxazolo[4,5-b]pyridin-6(7H)-one (example 27).

Example 29

N-(6-(2-fluoro-4-iodophenylamino)-7-fluoro-2,3-dimethyl-2H-indazol-5-yl)cyclopropanesulfonamide Step A: 7-fluoro-6-(2-fluoro-phenylamino)-3-methyl-2H-indazole-5-carboxylic acid methyl ester

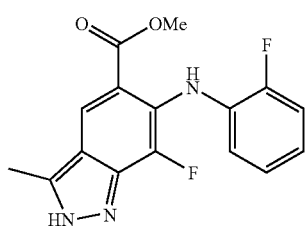

To a solution of methyl 5-acetyl-2-(2-fluorophenylamino)-3,4-difluorobenzoate (500 mg, 1.55 mmol, from step D in example 3) in DMF (10 ml) was added hydrazine (0.06 mL, 1.85 mmol). After stirring at room temperature for 16 h, the reaction was quenched with NH₄Cl solution and extracted with EtOAc. The organic layer was dried (MgSO₄) and concentrated under reduced pressure to afford 740 mg (75%) of the title compound.

Step B: 7-fluoro-6-(2-fluoro-phenylamino)-2,3-dimethyl-2H-indazole-5-carboxylic acid methyl ester

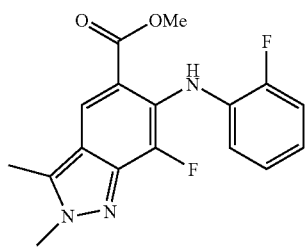

To a solution of 7-fluoro-6-(2-fluoro-phenylamino)-3-methyl-2H-indazole-5-carboxylic acid methyl ester (146 mg, 0.46 mmol) in DMF (5 ml) were added potassium carbonate (95 mg, 069 mmol) and iodomethane (0.034 mL, 0.55 mmol). The reaction was stirred at room temp overnight, diluted with EtOAc and washed with H₂O. The organic fraction was dried over MgSO₄ and concentrated under reduced pressure. Silica gel chromatography (EtOAc:Hexanes=75:25) yielded 40 mg (26%) of the title compound and 81 mg (53%) of 7-fluoro-6-(2-fluoro-phenylamino)-1,3-dimethyl-1H-indazole-5-carboxylic acid methyl ester.

Step C: 7-fluoro-6-(2-fluoro-4-iodophenylamino)-2,3-dimethyl-2H-indazole-5-carboxylic acid methyl ester

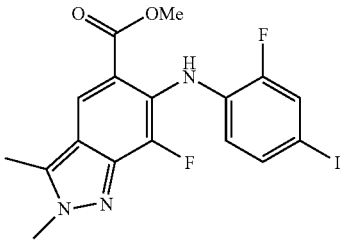

To a solution of 7-fluoro-6-(2-fluoro-phenylamino)-2,3-dimethyl-2H-indazole-5-carboxylic acid methyl ester (141 mg, 0.43 mmol) in DMF (5 ml) were added NIS (144 mg, 0.64 mmol) and TFA (0.20 mL), and the reaction was stirred at room temp for 4 h. The crude was diluted with EtOAc and washed with H₂O. The organic fraction is dried over MgSO₄ and concentrated under reduced pressure. Silica gel chromatography (EtOAc:Hexanes=75:25) yielded 137 mg (70%) of the title compound as a yellow solid.

Step D: 7-fluoro-6-(2-fluoro-4-iodophenylamino)-2,3-dimethyl-2H-indazole-5-carboxylic acid

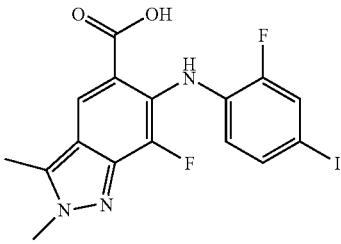

To a solution of 7-fluoro-6-(2-fluoro-4-iodophenylamino)-2,3-dimethyl-2H-indazole-5-carboxylic acid methyl ester (137 mg, 0.30 mmol) in a mixture of THF (10 ml) and H₂O (5 ml) was added a solution of LiOH (1.50 mL, 1M in H₂O, 1.50 mmol). After stirring at room temperature for 4 h, the reaction was concentrated, acidified with 1 M HCl solution, and extracted with EtOAc (2×20 ml). The organic solution was dried over MgSO₄ and concentrated to give 126 mg (96%) the title compound as an orange solid.

Step E: 8-fluoro-7-(2-fluoro-4-iodophenyl)-2,3-dimethyl-2,7-dihydro-5H-imidazo[4,5-f]indazol-6-one

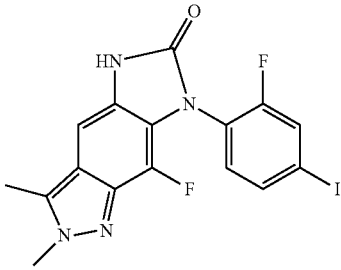

To a suspension of 7-fluoro-6-(2-fluoro-4-iodophenylamino)-2,3-dimethyl-2H-indazole-5-carboxylic acid (126 mg, 0.29 mmol) in toluene (10 ml) was added triethylamine (0.13 ml, 0.90 mmol) and diphenylphosphoryl azide (0.081 ml, 0.38 mmol). The reaction was heated at reflux for 4 h. The mixture was cooled to room temperature and concentrated to dryness. Silica gel chromatography (EtOAc:Hexane=75:25) yields 51 mg (39%) of the title compound as a light yellow solid.

Step F: 5-cyclopropanesulfonyl-8-fluoro-7-(2-fluoro-4-iodophenyl)-2,3-dimethyl-2,7-dihydro-5H-imidazo[4,5-f]indazol-6-one

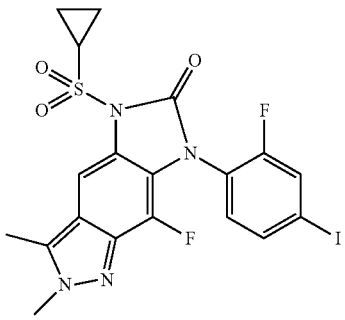

To a solution of 8-fluoro-7-(2-fluoro-4-iodophenyl)-2,3-dimethyl-2,7-dihydro-5H-imidazo[4,5-f]indazol-6-one (34 mg, 0.077 mmol) in THF (5 ml) at −78° C. was added LiHMDS (0.12 ml, 1 M in THF, 0.12 mmol). The reaction mixture was stirred at −78° C. for 10 min and cyclopropylsulfonyl chloride (22 mg, 0.15 mmol) was added to the mixture. The reaction was slowly warmed to room temperature and stirred at the temperature for 16 h. The reaction was quenched with saturated aqueous NH$_4$Cl solution (10 ml) and extracted with EtOAc (2×10 ml). The combined organic solution was washed with brine (20 ml), dried over MgSO$_4$ and concentrated. Silica gel chromatography (EtOAc:Hexanes=25:75) yields 24 mg (57%) of the title compound as a yellow solid.

Step G: N-(6-(2-fluoro-4-iodophenylamino)-7-fluoro-2,3-dimethyl-2H-indazol-5-yl)cyclopropanesulfonamide

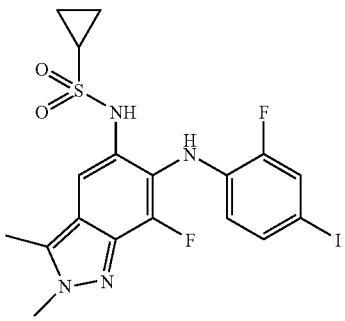

To a solution of 5-cyclopropanesulfonyl-8-fluoro-7-(2-fluoro-4-iodophenyl)-2,3-dimethyl-2,7-dihydro-5H-imidazo[4,5-f]indazol-6-one (24 mg, 0.044 mmol) in THF (3 ml) was added potassium trimethylsilanolate (11 mg, 0.088 mmol). The reaction was stirred at room temperature for 5 h, quenched with saturated aqueous NH$_4$Cl solution (5 ml), and extracted with EtOAc (2×10 ml). The combined organic solution was washed with brine (15 ml), dried over MgSO$_4$, and concentrated. Silica gel chromatography (EtOAc:Hexanes=50:50) yielded 19 mg (83%) of the title compound. m/z=517 [M−1]$^−$. $^1$H NMR (DMSO-d$_6$, 400 MHz): δ 0.78 (m, 4H), 2.48 (m, 1H), 2.68 (s, 3H), 4.13 (s, 3H), 6.38 (m, 1H), 7.32 (d, J=8 Hz, 1H), 7.41 (s, 1H), 7.59 (m, 2H), 9.23 (s, 1H).

Example 30

N-(6-(2-fluoro-4-iodophenylamino)-7-fluoro-1,3-dimethyl-1H-indazol-5-yl)cyclopropanesulfonamide

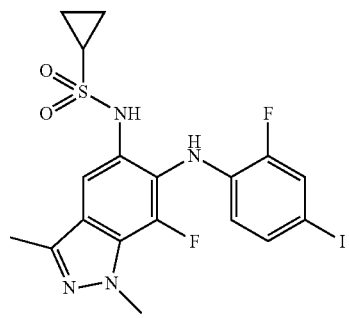

This compound was synthesized according to example 29 (step C through G) starting from 7-fluoro-6-(2-fluoro-phenylamino)-1,3-dimethyl-1H-indazole-5-carboxylic acid methyl ester (step B, example 29). m/z=517 [M−1]$^−$. $^1$H NMR (DMSO-d$_6$, 400 MHz): δ 0.71 (m, 2H), 0.79 (m, 2H), 2.49 (m, 1H), 2.47 (s, 3H), 4.05 (s, 3H), 6.49 (m, 1H), 7.26 (d, J=8 Hz, 1H), 7.48 (s, 1H), 7.55 (s, 1H), 7.57 (s, 1H), 9.26 (s, 1H)

Example 31

N-(6-(2-fluoro-4-iodophenylamino)-7-fluoro-2,3-dimethyl-2H-indazol-5-yl)-1-(2-hydroxyethyl)cyclopropane-1-sulfonamide

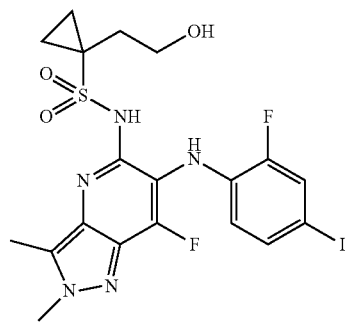

This compound is synthesized according to example 4 (step A through C) starting from 8-fluoro-7-(2-fluoro-4-iodophenyl)-2,3-dimethyl-2,7-dihydro-5H-imidazo[4,5-f]indazol-6-one (example 29).

Example 32

N-(7-fluoro-6-(2-fluoro-4-iodophenylamino)-3-methylisoxazolo[4,3-b]pyridin-5-yl)cyclopropanesulfonamide

Step A: Methyl 7-fluoro-6-(2-fluorophenylamino)-3-methylisoxazolo[4,3-b]pyridine-5-carboxylate

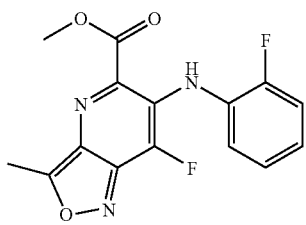

To a solution of methyl 6-acetyl-5-chloro-4-fluoro-3-(2-fluorophenylamino)picolinate (WO 2005/051906) (2 g, 5 mmole) in a mixture of acetone (36 ml) and H$_2$O (12 ml) is added NaN$_3$ (487 mg, 7.5 mmol). The reaction is heated at 65° C. for 16 h and cooled to room temperature. Acetone is concentrated and the resulting mixture is extracted with EtOAc (2×50 ml). The combined organic solution is washed with brine (50 ml), dried over MgSO$_4$ and concentrated to give a yellow solid. To the solid is added H$_2$O (24 ml) and the reaction is heated at reflux for 3 h. The reaction is cooled to room temperature, filtered, and washed with H$_2$O. The resulting solid is dried under high vacuum with P$_2$O$_5$ at 65° C. for 24 h to give the title compound.

Step B: Methyl 7-fluoro-6-(2-fluoro-4-iodophenylamino)-3-methylisoxazolo[4,3-b]pyridine-5-carboxylate

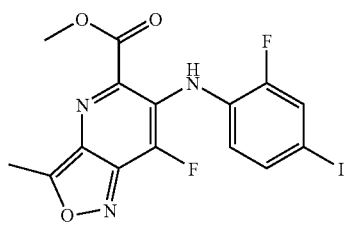

To a suspension of methyl 7-fluoro-6-(2-fluorophenylamino)-3-methylisoxazolo[4,3-b]pyridine-5-carboxylate (1.35 g, 4.25 mmol) in DMF (40 ml) is added N-iodosuccinimide (1.43 g, 6.37 mmol) and TFA (2.5 ml). After stirring at room temperature for 4 h, the reaction is quenched with saturated aqueous NH$_4$Cl solution (100 ml) and extracted with EtOAc (2×100 ml). The combined organic solution is washed with brine (100 ml), dried over MgSO$_4$ and concentrated. Silica gel chromatography yields the title compound.

Step C: 7-Fluoro-6-(2-fluoro-4-iodophenylamino)-3-methylisoxazolo[4,3-b]pyridine-5-carboxylic acid

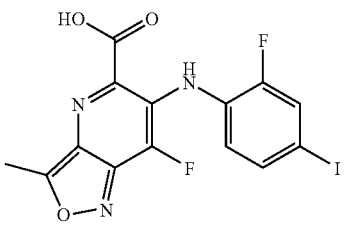

To a solution of methyl 7-fluoro-6-(2-fluoro-4-iodophenylamino)-3-methylisoxazolo[4,3-b]pyridine-5-carboxylate (250 mg, 0.56 mmol) in a mixture of THF (10 ml) and H$_2$O (5 ml) is added a solution of LiOH (67 mg, 2.8 mmol) in H$_2$O (2.4 ml). After stirring at room temperature for 4 h, the reaction is concentrated, acidified with 1 M HCl solution, and extracted with EtOAc (2×20 ml). The organic solution is dried over MgSO$_4$ and concentrated to give the title compound.

Step D: 8-Fluoro-7-(2-fluoro-4-iodophenyl)-3-methyl-5H-imidazo[4,5-b]isoxazolo[3,4-e]pyridin-6(7H)-one

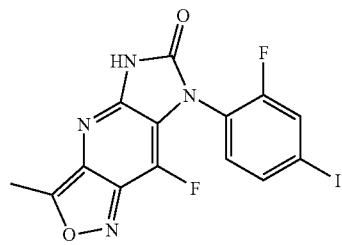

To a suspension of 7-fluoro-6-(2-fluoro-4-iodophenylamino)-3-methylisoxazolo[4,3-b]pyridine-5-carboxylic acid (241 mg, 0.56 mmol) in toluene (10 ml) is added triethylamine (0.23 ml, 1.68 mmol) and diphenylphosphoryl azide (0.26 ml, 1.21 mmol). The reaction is heated at reflux for 4 h. The mixture is cooled to room temperature and concentrated to dryness. Silica gel chromatography yields the title compound.

Step E: 5-(Cyclopropylsulfonyl)-8-fluoro-7-(2-fluoro-4-iodophenyl)-3-methyl-5H-imidazo[4,5-b]isoxazolo[3,4-e]pyridin-6(7H)-one

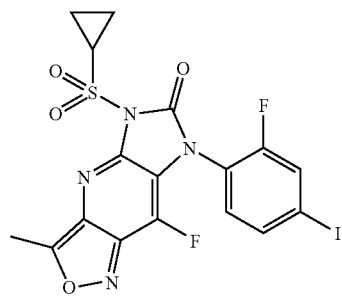

To a solution of 8-fluoro-7-(2-fluoro-4-iodophenyl)-3-methyl-5H-imidazo[4,5-b]isoxazolo[3,4-e]pyridin-6(7H)-one (143 mg, 0.33 mmol) in THF (10 ml) at −78° C. is added LiHMDS (0.38 ml, 1 M in THF, 0.38 mmol). The reaction mixture is stirred at −78° C. for 10 min and cyclopropylsulfonyl chloride (69 mg, 0.50 mmol) is added to the mixture. The reaction is slowly warmed to room temperature and stirred at the temperature for 16 h. The reaction is quenched with saturated aqueous $NH_4Cl$ solution (20 ml) and extracted with EtOAc (2×20 ml). The combined organic solution is washed with brine (20 ml), dried over $MgSO_4$ and concentrated. Silica gel chromatography yields the title compound.

Step F: N-(7-fluoro-6-(2-fluoro-4-iodophenylamino)-3-methylisoxazolo[4,3-b]pyridin-5-yl)cyclopropanesulfonamide

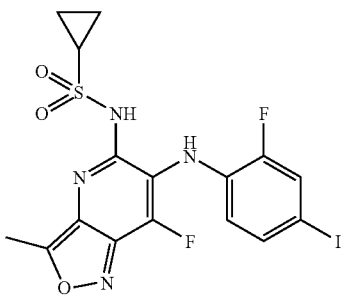

To a solution of 3-(cyclopropanesulfonyl)-8-fluoro-1-(2-fluoro-4-iodophenyl)-5-methylbenzimidazolo[6,5-d][c] isoxazole (131 mg, 0.25 mmol) in THF (15 ml) is added potassium trimethylsilanolate (95 mg, 0.75 mmol). The reaction is stirred at room temperature for 16 h, quenched with saturated aqueous $NH_4Cl$ solution (20 ml), and extracted with EtOAc (2×30 ml). The combined organic solution is washed with brine (30 ml), dried over $MgSO_4$, and concentrated. Silica gel chromatography yields the title compound.

Example 33

N-(7-fluoro-6-(2-fluoro-4-iodophenylamino)-3-methylisoxazolo[4,3-b]pyridin-5-yl)-1-(2-hydroxyethyl)cyclopropane-1-sulfonamide

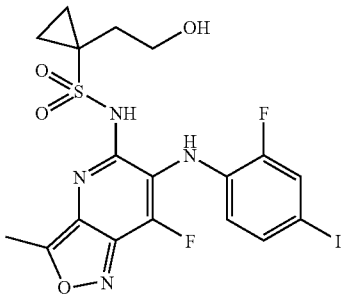

This compound is synthesized according to example 4 (step A through C) starting from 8-fluoro-7-(2-fluoro-4-iodophenyl)-3-methyl-5H-imidazo[4,5-b]isoxazolo[3,4-e]pyridin-6(7H)-one (example 32).

Example 34

N-(7-(2-fluoro-4-iodophenylamino)-8-fluoro-4-methylquinazolin-6-yl)cyclopropanesulfonamide Step A: 5-Bromo-2,3,4-trifluorobenzoic acid

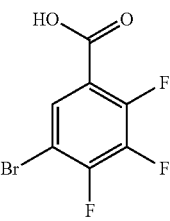

To a solution of $iPr_2NH$ (56.8 mmol, 8 ml) in THF (50 ml) at −78° C. was added dropwise a solution of nBuLi (1.6M in hexane, 56.8 ml, 35.5 mmol). The dry ice bath was removed and the mixture was stirred at 0° C. for ~15 min. The mixture is transferred via cannula to a solution of 1-bromo-2,3,4-trifluorobenzene (47.4 mmol, 10 g) in THF (50 ml) cooled at −78° C. The orange solution was stirred at −78° C. for 1 h, then transferred, via cannula, to freshly grinded dry $CO_2$. The reaction was warmed up to room temperature and stirred overnight. The reaction mixture was cooled at 0° C., quenched with 10% HCl (300 ml), extracted with ether (100 ml×3), dry over $MgSO_4$ and concentrated under reduced pressure to obtain (10.6 g, 88%) of the title compound.

Step B: 5-Bromo-2-(2-fluorophenylamino)-3,4-difluorobenzoic acid

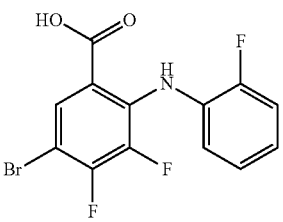

To a solution of 2-fluoro-aniline (177 mmol, 17.0 ml) in THF (80 mL) at −78° C. was added LiHMDS (265 mmol, 265 ml) and stirred for 30 min. To the reaction was added a solution of 5-bromo-2,3,4-trifluorobenzoic acid (78.4 mmol, 20.1 g) in THF (60 ml) at −78° C. The reaction was warmed to room temperature and stirred at the temperature over night. The reaction is concentrated and slowly 10% HCl (180 ml) is added. The mixture was extracted with ethyl acetate (100 ml×3), dried over $MgSO_4$ and concentrated under reduced pressure. The crude material was taken in $CH_2CH_2$ (~250 ml) and heated up to 45° C. for 10 min. Purification by trituration with $CH_2Cl_2$ gave 11 g (72%) of the desired product as a light yellow solid.

Step C: Methyl 5-bromo-2-(2-fluorophenylamino)-3,4-difluorobenzoate

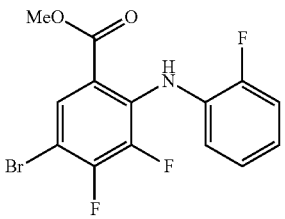

To a solution of 5-bromo-2-(2-fluorophenylamino)-3,4-difluorobenzoic acid (30.3 mmol, 11 g) in THF:MeOH (60:20), cooled to 0° C., was added dropwise a solution of 2M TMSCHN₂ in hexane (39.39 mmol, 19.7 ml). After the addition is completed, the reaction mixture was warmed to room temperature and stirred for an additional 4 hours. The crude reaction was quenched with acetic acid and extracted with EtOAc. The organic layers are combined, washed with H₂O, dry over MgSO₄ and concentrated under reduced pressure. The crude material was dried under vacuum and yields to 11 g (96%) of the title product.

Step D: Methyl 2-(2-fluorophenylamino)-3,4-difluoro-5-((trimethylsilyl)ethynyl)benzoate

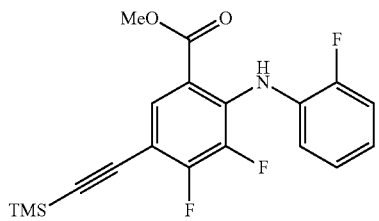

To an oven dried flask charged with a solution of methyl 5-bromo-2-(2-fluorophenylamino)-3,4-difluorobenzoate (21.68 mmol, 8.1 g) in THF (116 ml), was added CuI (2.16 mmol, 0.4 g) and iPr₂NH (43.36 mmol, 6.1 ml). After addition is completed, reaction was purged with Argon and Pd(PPh₃)₂Cl₂ (3.73 mmol, 2.62 g) and TMS-acetylene (26.88 mmol, 3.7 ml) are added. The reaction mixture was stirred at room temperature for 16 h, concentrated and taken up in EtOAc. The organic fraction was washed with sat NH₄Cl, brine, dried over MgSO₄ and conc. The crude was purified by flash chromatography using 5% to 20% EtOAc in Hexane to afford the desired product 6.96 g (85%).

Step E: Methyl 5-acetyl-2-(2-fluorophenylamino)-3,4-difluorobenzoate

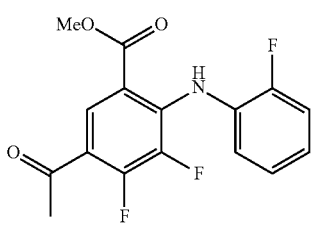

A mixture of methyl 2-(2-fluorophenylamino)-3,4-difluoro-5-((trimethylsilyl)ethynyl)benzoate (9 mmol, 3.5 g), HgSO₄ (9 mmol, 2.67 g), and conc. H₂SO₄ (18 mmol, 0.96 ml) in acetone:H₂O (70:12 ml) was refluxed at 65° C. overnight. The mixture was concentrated, diluted with EtOAc, and washed with water and brine. The organic fractions are combined, dried over MgSO₄ and concentrated under reduced pressure. The crude material (brown solid) was triturated with MeOH and the precipitate was filtered, washed with additional MeOH and dried to yield the desired product in 60% (1.78 g).

Step F: Methyl 5-acetyl-2-(2-fluoro-4-iodophenylamino)-3,4-difluorobenzoate

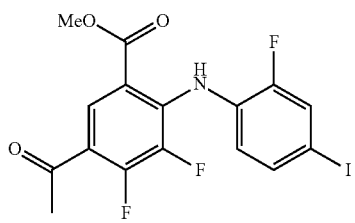

To a solution of methyl 5-acetyl-2-(2-fluorophenylamino)-3,4-difluorobenzoate (0.47 mmol, 0.16 g) in DMF (10 ml) was added NIS (0.56 mmol, 0.13 g) and TFA (0.10 ml), and the reaction was stifled at room temp overnight. The crude was diluted with EtOAc and washed with H₂O. The organic fraction was dried over MgSO₄ and concentrated under reduced pressure to yield the desired product in 90% (0.23 g).

Step G: Methyl 7-(2-fluoro-4-iodophenylamino)-8-fluoro-4-methylquinazoline-6-carboxylate

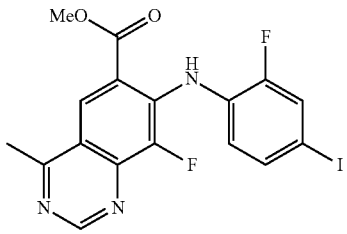

A mixture of methyl 5-acetyl-2-(2-fluoro-4-iodophenylamino)-3,4-difluorobenzoate (230 mg, 0.55 mmol) and formamide acetate (68 mg, 0.66 mmol) in DMA (5 ml) was heated at 95° C. for 6 hours. The reaction mixture was diluted with EtOAc and washed with water and brine. The organic layer was dried (MgSO₄) and concentrated under reduced pressure to afford 205 mg (88%) of the title compound.

Step H: 7-(2-Fluoro-4-iodophenylamino)-8-fluoro-4-methylquinazoline-6-carboxylic acid

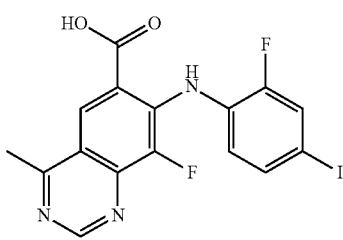

To a solution of methyl 7-(2-fluoro-4-iodophenylamino)-8-fluoro-4-methylquinazoline-6-carboxylate (205 mg, 0.48 mmol) in a mixture of THF (10 ml) and H₂O (5 ml) was added a solution of LiOH (57 mg, 2.4 mmol) in H₂O (2.4 ml). After stirring at room temperature for 4 h, the reaction was concentrated, acidified with 1 M. HCl solution, and extracted with EtOAc (2×20 ml). The organic solution was dried over MgSO₄ and concentrated to give 190 mg (96%) the title compound as an orange solid.

Step I: 3-(2-Fluoro-4-iodophenyl)-4-fluoro-8-methyl-1H-imidazo[4,5-g]quinazolin-2(3H)-one

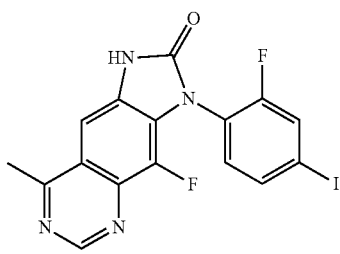

To a suspension of 7-(2-fluoro-4-iodophenylamino)-8-fluoro-4-methylquinazoline-6-carboxylic acid (190 mg, 0.47 mmol) in toluene (10 ml) was added triethylamine (0.19 ml, 1.41 mmol) and diphenylphosphoryl azide (0.20 ml, 0.94 mmol). The reaction was heated at reflux for 4 h. The mixture was cooled to room temperature and concentrated to dryness. Silica gel chromatography (EtOAc:Hexane=75:25) yields 143 mg (75%) of the title compound as a tan solid.

Step J: 3-(2-Fluoro-4-iodophenyl)-1-(cyclopropylsulfonyl)-4-fluoro-8-methyl-1H-imidazo[4,5-g]quinazolin-2(3H)-one

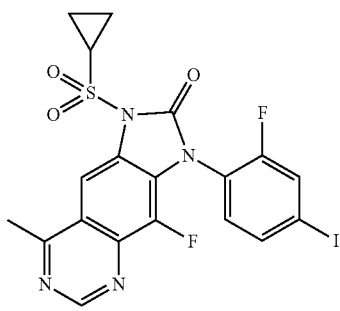

To a solution of 3-(2-fluoro-4-iodophenyl)-4-fluoro-8-methyl-1H-imidazo[4,5-g]quinazolin-2(3H)-one (50 mg, 0.12 mmol) in THF (10 ml) at −78° C. was added LiHMDS (0.16 ml, 1 M in THF, 0.16 mmol). The reaction mixture was stirred at −78° C. for 10 min and cyclopropylsulfonyl chloride (25 mg, 0.18 mmol) was added to the mixture. The reaction was slowly warmed to room temperature and stirred at the temperature for 16 h. The reaction was quenched with saturated aqueous NH₄Cl solution (10 ml) and extracted with EtOAc (2×10 ml). The combined organic solution was washed with brine (20 ml), dried over MgSO₄ and concentrated. Silica gel chromatography (EtOAc:Hexanes=25:75) yields 46 mg (75%) of the title compound as a yellow solid.

Step K: N-(7-(2-Fluoro-4-iodophenylamino)-8-fluoro-4-methylquinazolin-6-yl)cyclopropanesulfonamide

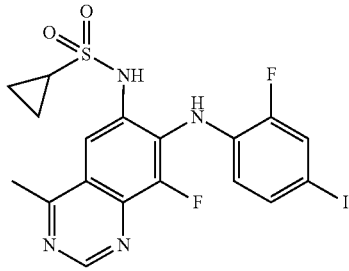

To a solution of 3-(2-fluoro-4-iodophenyl)-1-(cyclopropylsulfonyl)-4-fluoro-8-methyl-1H-imidazo[4,5-g]quinazolin-2(3H)-one (46 mg, 0.09 mmol) in THF (5 ml) was added potassium trimethylsilanolate (35 mg, 0.27 mmol). The reaction was stirred at room temperature for 16 h, quenched with saturated aqueous NH₄Cl solution (5 ml), and extracted with EtOAc (2×10 ml). The combined organic solution was washed with brine (15 ml), dried over MgSO₄, and concentrated. Silica gel chromatography (EtOAc:Hexanes=50:50) yielded 39 mg (90%) of the title compound as a light yellow solid. m/z=515 [M−1]⁻. ¹H NMR (DMSO-d₆, 400 MHz): δ 0.85 (m, 4H), 2.75 (m, 1H), 2.87 (s, 3H), 6.61 (m, 1H), 7.36 (d, J=8 Hz, 1H), 7.67 (d, J=11 Hz, 1H), 8.02 (s, 2H), 9.07 (s, 1H), 9.78 (s, 1H).

Example 35

N-(7-(2-fluoro-4-iodophenylamino)-8-fluoro-4-methylquinazolin-6-yl)-1-(2-hydroxyethyl)cyclopropane-1-sulfonamide Step A: 3-(2-Fluoro-4-iodophenyl)-1-(1-(2-(tert-butyldimethylsilyloxy)ethyl)cyclopropylsulfonyl)-4-fluoro-8-methyl-1H-imidazo[4,5-g]quinazolin-2(3H)-one

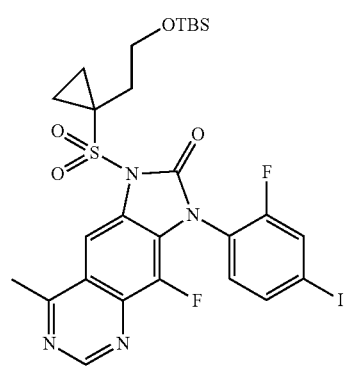

To a solution of 3-(2-fluoro-4-iodophenyl)-4-fluoro-8-methyl-1H-imidazo[4,5-g]quinazolin-2(3H)-one (example 34, step H) (90 mg, 0.22 mmol) in THF (5 ml) at −78° C. is added LiHMDS (0.29 ml, 1 M in THF, 0.29 mmol). The reaction mixture is stirred at −78° C. for 30 min and 1-(2-(tert-butyldimethylsilyloxy)ethyl)cyclopropane-1-sulfonyl chloride (99 mg, 0.33 mmol) is added to the mixture. The reaction is slowly warmed to room temperature and stirred at the temperature for 16 h. The reaction is quenched with saturated aqueous NH₄Cl solution (20 ml) and extracted with EtOAc (2×30 ml). The combined organic solution is washed with brine (30 ml), dried over MgSO₄ and concentrated. Silica gel chromatography yields the desired product.

Step B: N-(7-(2-Fluoro-4-iodophenylamino)-8-fluoro-4-methylquinazolin-6-yl)-1-(2-(tert-butyldimethylsilyloxy)ethyl)cyclopropane-1-sulfonamide

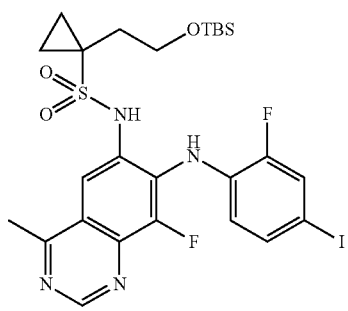

To a solution of 3-(2-fluoro-4-iodophenyl)-1-(1-(2-(tert-butyldimethylsilyloxy)ethyl)cyclopropylsulfonyl)-4-fluoro-8-methyl-1H-imidazo[4,5-g]quinazolin-2(3H)-one (66 mg, 0.1 mmol) in THF (5 ml) is added potassium trimethylsilanolate (65 mg, 0.5 mmol). The resulting solution is stirred at room temperature for 24 h. The reaction is quenched with saturated aqueous NH₄Cl solution (10 ml) and extracted with EtOAc (2×10 ml). The combined organic solution is washed with brine (10 ml), dried over MgSO₄ and concentrated. Silica gel chromatography yields the desired product.

Step C: N-(7-(2-Fluoro-4-iodophenylamino)-8-fluoro-4-methylquinazolin-6-yl)-1-(2-hydroxyethyl)cyclopropane-1-sulfonamide

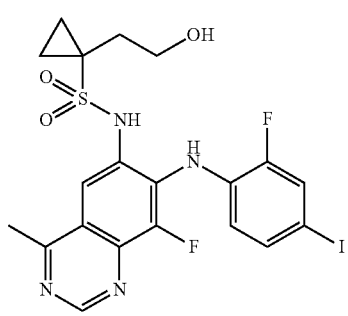

To a solution of N-(7-(2-fluoro-4-iodophenylamino)-8-fluoro-4-methylquinazolin-6-yl)-1-(2-(tert-butyldimethylsilyloxy)ethyl)cyclopropane-1-sulfonamide (36 mg, 0.056 mmol) in THF (2 ml) is added HCl (0.18 ml, 1.2 N in H₂O, 0.22 mmol). After stirring for 1 h, the reaction is quenched with saturated aqueous NaHCO₃ solution (3 ml) and extracted with EtOAc (2×10 ml). The combined organic solution is dried over Na₂SO₄ and concentrated. Silica gel chromatography yields the title compound.

Example 36

N-(7-(2,4-dichlorophenylamino)-8-fluoro-4-methylcinnolin-6-yl)cyclopropanesulfonamide

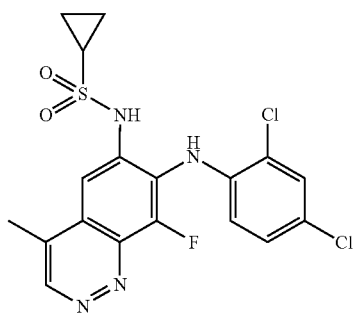

This compound is synthesized according to example 34 starting from 7-(4-bromo-2-chlorophenylamino)-8-fluoro-4-methylcinnoline-6-carboxylic acid (WO 2005/051302).

Example 37

N-(7-(2,4-dichlorophenylamino)-8-fluoro-4-methylcinnolin-6-yl)-1-(2-hydroxyethyl)cyclopropane-1-sulfonamide

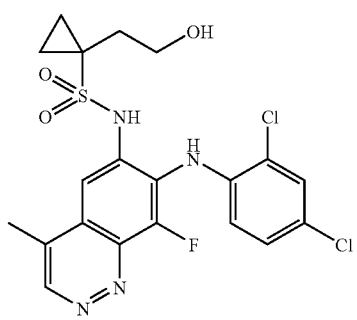

This compound is synthesized according to example 35 (step A through C) starting from 8-(2,4-dichlorophenyl)-9-fluoro-4-methyl-6H-imidazo[4,5-g]cinnolin-7(8H)-one (example 36).

Example 38

N-(7-(4-bromo-2-fluorophenylamino)-8-fluoro-4-methylquinolin-6-yl)cyclopropanesulfonamide

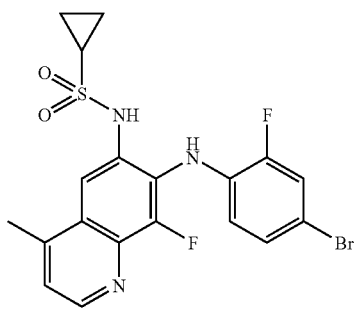

This compound is synthesized according to example 34 starting from 7-(4-bromo-2-fluorophenylamino)-8-fluoro-4-methylquinoline-6-carboxylic acid (WO 2005/051302).

Example 39

N-(7-(4-bromo-2-fluorophenylamino)-8-fluoro-4-methylquinolin-6-yl)-1-(2-hydroxyethyl)cyclopropane-1-sulfonamide

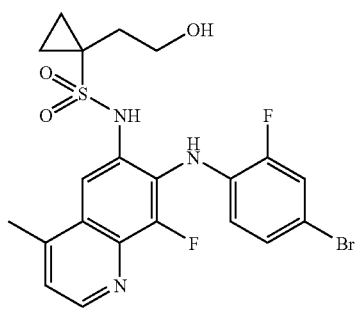

This compound is synthesized according to example 35 (step A through C) starting from 3-(4-bromo-2-fluorophenyl)-4-fluoro-8-methyl-1H-imidazo[4,5-g]quinolin-2(3H)-one (example 38).

Example 40

Biological Activity

Generation of IC50 Data

Materials and preparation of reagents: Human GST-MEK1 and the constitutively active allele GST-MEK1$^{CA}$ (harboring the mutations Ser218Asp and Ser222Asp) can be subcloned into the yeast expression vector pGEM4Z (Promega, Madison, Wis.) from the wild type human MEK1 cDNA. GST-MEK1CA was expressed in *Escherichia coli* and can be partially purified using Glutathione Sepharose 4B affinity resin (Amersham Pharmacia Biotech, Piscataway, N.J.). The ERK2 allele can be subcloned from MAPK2/Erk2 cDNA (wild type) in 10 pUSEamp (Upstate Biotechnology, Inc., Waltham, Mass.) into the vector pET21a (Novagen, Madison, Wis.) resulting in an N-terminal histidine-tagged mouse ERK2 allele. ERK2 can be expressed and purified to homogeneity [Zhang, 1993 #33]. Myelin basic protein (MBP) can be purchased from Gibco BRL (Rockville, Md.). EasyTides adenosine 5'-triphosphate (ATP) ([γ-33P]) (NEN Perkin Elmer, Wellesley, Mass.) is the source of radiolabel for all kinase reactions. Activated Raf-1 (truncated) and activated MAPKinase 2/ERK2 can be purchased from Upstate, Inc. (Lake Placid, N.Y.). 4-20% Criterion Precast gels can be purchased from Bio-Rad (Hercules, Calif.).

Determination of enzymatic activity: Compounds are diluted from dimethylsulfoxide (DMSO) stocks into 1×HMNDE (20 mM HEPES pH 7.2, 1 mM MgCl2, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 µCi [γ33P] ATP. The screening assay essentially comprises four additions. Five µl of diluted compound are dispensed to 96-well assay plates. Ten µl of 2.5× enzyme cocktail (MEK1$^{CA}$ and ERK2 only) are then added to each well followed by a preincubation for 30 minutes at ambient temperature. Ten µl of 2.5× substrate cocktail (labeled and unlabeled ATP plus MBP) are then added, followed by incubation for 60 minutes at ambient temperature. Finally, 100 µl of 10% trichloroacetic acid (TCA) are added and incubated for 30 minutes at room temperature to halt the reaction and precipitate radiolabeled protein products. Reaction products are harvested on glass fiber 96 well filter plates prewetted with water and 1% pyrophosphate. The filter plate is then washed 5 times with water. Water is displaced by absolute ethanol and the plate is allowed to air dry for 30 minutes at room temperature. A back seal is applied manually and 40 µl of scintillation cocktail are dispensed to each well. A top seal is applied and the plate is counted in the TopCount for two seconds per well.

A truncated version of MEK that requires activation by Raf kinase can be used.

Generation of EC50 Data

Effects of compounds in the cell can be determined by Western blotting for phosphorylated ERK. MDA-MB-231 breast cancer cells are plated in a 48 well plate at 20,000 cells per well and are grown in a 37° humidified $CO_2$ incubator. The following day, the growth media (DMEM+10% fetal bovine serum) is removed and replaced with starve media (DMEM+0.1% fetal bovine serum). Cells are incubated in the starve media for sixteen hours and then treated with a range of compound concentrations for thirty minutes.

After incubation with compound, cells are stimulated with 100 ng/ml EGF for five minutes. The cells are then lysed and analyzed by Western blot using a monoclonal antibody raised to phosphorylated ERK. The signal is amplified using a secondary antibody conjugated to a near-IR dye and detected on a Licor Odyssey scanner. The intensity of signal is quantitated and this data was used to generate dose response curves and $EC_{50}$ calculations.

| Example | Structure | IC$_{50}$ (nM) | EC$_{50}$ (nM) |
|---------|-----------|----------------|----------------|
| 2 | 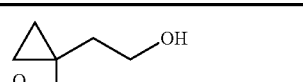 | C | B |

-continued

| Example | Structure | IC$_{50}$ (nM) | EC$_{50}$ (nM) |
|---|---|---|---|
| 3 | 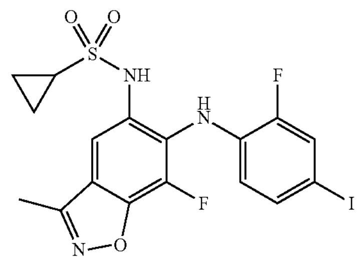 | C | B |
| 4 | 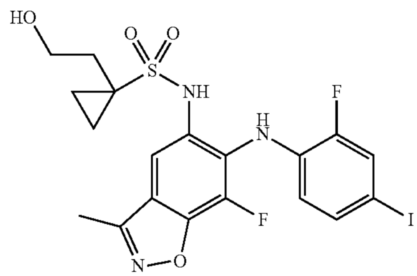 | C | B |
| 5 | 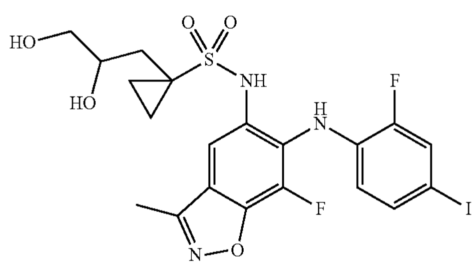 | B | A |
| 6 | 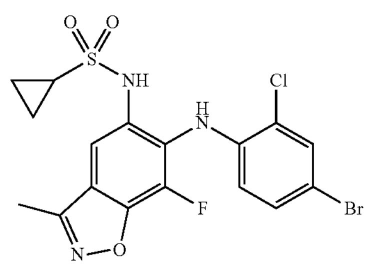 | D | B |
| 7 | 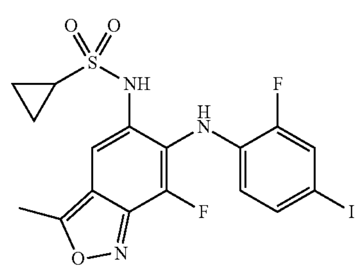 | C | C |
| 9 | 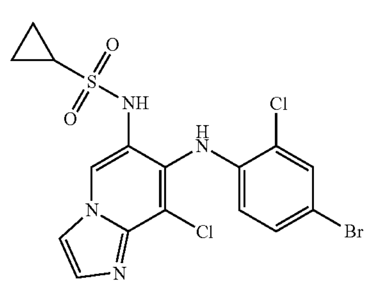 | D | C |

-continued

| Example | Structure | IC$_{50}$ (nM) | EC$_{50}$ (nM) |
|---|---|---|---|
| 10 | 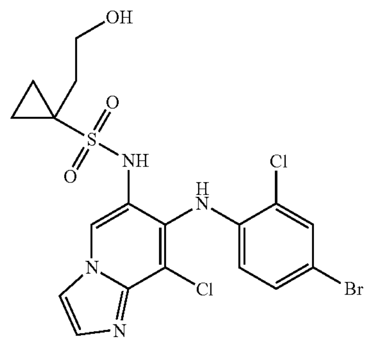 | D | C |
| 12 | 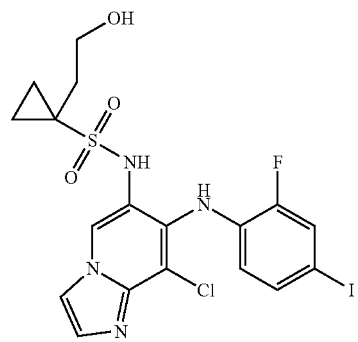 | C | B |
| 14 | 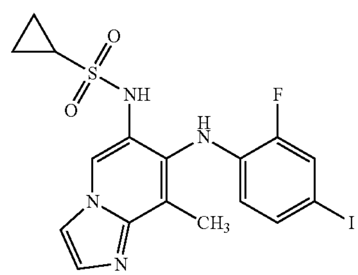 | C | A |
| 16 | 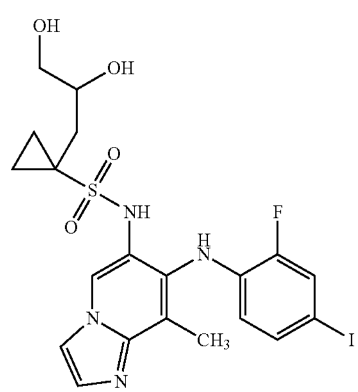 | C | C |

-continued

| Example | Structure | IC$_{50}$ (nM) | EC$_{50}$ (nM) |
|---|---|---|---|
| 17 | 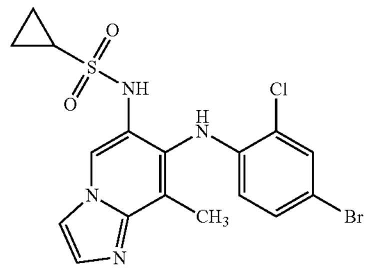 | D | C |
| 18 | 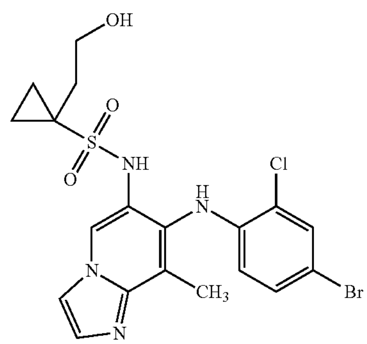 | E | C |
| 29 | 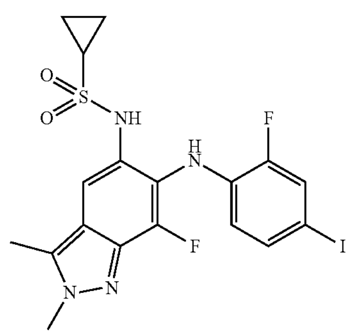 | E | B |
| 30 | 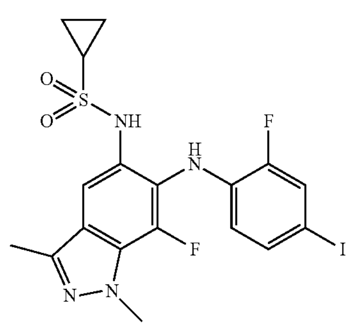 | F | D |

-continued

| Example | Structure | IC$_{50}$ (nM) | EC$_{50}$ (nM) |
|---|---|---|---|
| 34 | 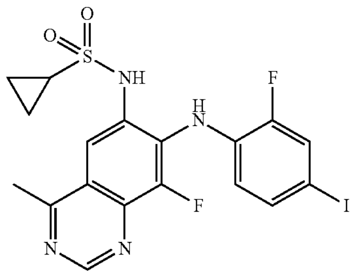 | F | D |

VALUE RANGE
A 0.1-1
B 1-10
C 10-100
D 100-1000
E 1000-10,000
F 10,000-50,000

What is claimed is:

1. A compound according to formula II-A, II-B, II-C, II-E or II-F, or a pharmaceutically acceptable salt, ester or tautomer thereof

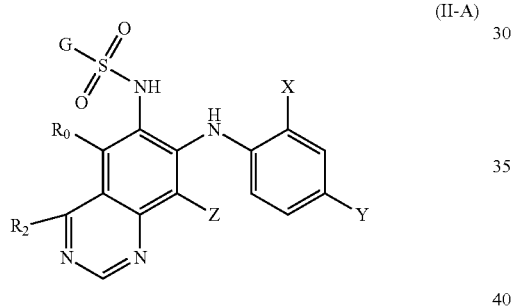
(II-A)

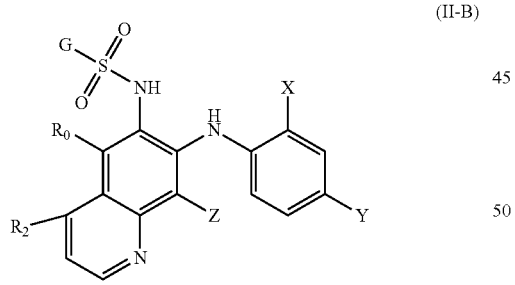
(II-B)

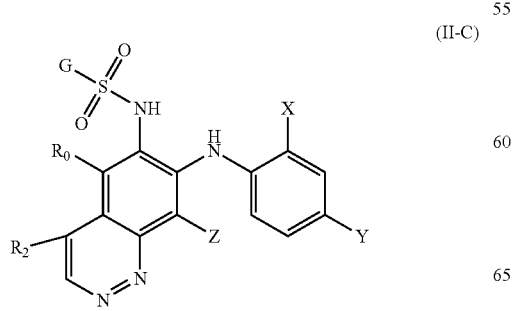
(II-C)

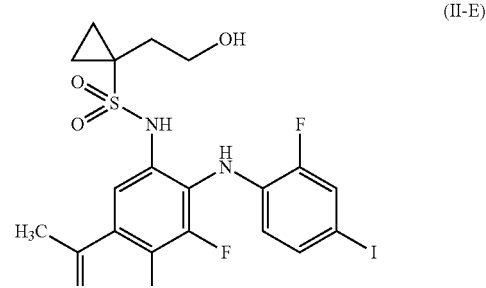
(II-E)

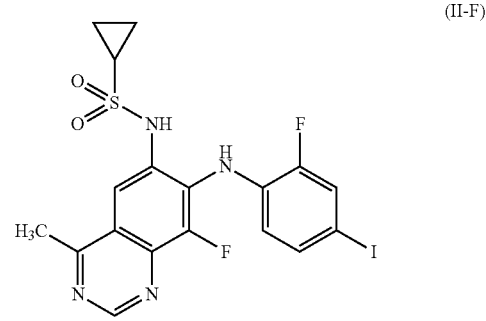
(II-F)

wherein

G is $R_{1a}$, $R_{1b}$, $R_{1c}$, $R_{1d}$, $R_{1e}$, $Ar_1$, $Ar_2$ or $Ar_3$;

$R_o$ and $R_2$ are independently selected from the group consisting of H, halogen, cyano, cyanomethyl, nitro, difluoromethoxy, difluoromethoxy, trifluoromethyl, azido, $CO_2R_5$, $OR_5$, —O—(CO)—$R_5$, —O—C(O)—N($R_5$)$_2$, —N$R_5$C(O)N$R_6R_7$, —S$R_5$, NHC(O)$R_5$, —NHSO$_2R_5$, SO$_2$N($R_5$)$_2$, C1-C6 alkyl, C1-C4 alkoxy, C3-C6 cycloalkyl, C2-C6 alkenyl, C2-C6 alkynyl, aryl, alkylaryl, arylalkyl, and heterocyclic groups; wherein said alkyl, cycloalkyl, alkenyl, aryl, alkylaryl, arylalkyl, heterocyclic and alkynyl groups are optionally substituted with 1-3 substituents independently selected from the group consisting of halogen, OH, CN, cyanomethyl, nitro, phenyl, difluoromethoxy, difluoromethoxy, and trifluoromethyl;

said C1-C6 alkyl and C1-C4 alkoxy groups are optionally substituted with OCH$_3$ or OCH$_2$CH$_3$;

each $R_5$ is selected from the group consisting of H, lower alkyl, substituted lower alkyl, aryl, substituted aryl, and $NR_7R_6$;
  wherein each $R_6$ and $R_7$ is independently selected from the group consisting of hydrogen and lower alkyl;
X is F, Cl or methyl;
Y is I, Br, Cl, $CF_3$, C1-C3 alkyl, C2-C3 alkenyl, C2-C3 alkynyl, cyclopropyl, phenyl, pyridyl, pyrazolyl, OMe, OEt, or SMe, wherein
  all said methyl, ethyl, C1-C3 alkyl, and cyclopropyl groups of X and Y are optionally substituted with OH;
  all said phenyl, pyridyl, pyrazolyl groups of Y are optionally substituted with halogen, acetyl, methyl, or trifluoromethyl; and
  all said methyl groups of X and Y are optionally substituted with one, two, or three F atoms;
Z is H, methyl, Cl or F;
$R_{1a}$ is methyl, cyclopropoxy or C1-C4 alkoxy; wherein
  the methyl is optionally substituted with OH, 1-3 fluorine atoms or 1-3 chlorine atoms;
  the C1-C4 alkyl moieties of said C1-C4 alkoxy are optionally substituted with one hydroxy or methoxy group; and
  all C2-C4 alkyl groups within said C1-C4 alkoxy are optionally further substituted with a second OH group;
$R_{1b}$ is $CH(CH_3)$—C1-3 alkyl or C3-C6 cycloalkyl, said $CH_3$, alkyl, and cycloalkyl groups are optionally substituted with 1-3 substituents selected independently from the group consisting of F, Cl, Br, I, OH, C1-C4 alkoxy and CN,
$R_{1c}$ is $(CH_2)_nO_mR'$, where
  m is 0 or 1; wherein
    when m is 1, n is 2 or 3, and
    when m is 0, n is 1 or 2;
  R' is C1-C6 alkyl, optionally substituted with 1-3 substituents independently selected from the group consisting of F, Cl, OH, $OCH_3$, $OCH_2CH_3$, and C3-C6 cycloalkyl;
$R_{1d}$ is $C(A')(A'')(B)$— wherein
  B, A', and A" are, independently, H or C1-4 alkyl, optionally substituted with one or two OH groups or halogen atoms, or
  A' and A", together with the carbon atom to which they are attached, form a 3- to 6-member saturated ring, said ring optionally containing one or two heteroatoms independently selected from the group consisting of O, N, and S and optionally substituted with one or two groups independently selected from the group consisting of methyl, ethyl, and halo;
$R_{1e}$ is benzyl or 2-phenyl ethyl, in which the phenyl group is optionally substituted

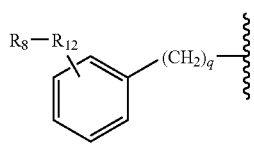

where
q is 1 or 2;
$R_8$ and $R_9$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, or methylsulfonyl;
$R_{10}$ is H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, nitro, acetamido, amidinyl, cyano, carbamoyl, methylcarbamoyl, dimethylcarbamoyl, 1,3,4-oxadiazol-2-yl, 5-methyl-1,3,4-5 oxadiazolyl, 1,3,4-thiadiazolyl, 5-methyl-1,3,4-thiadiazol-1H-tetrazolyl, N-morpholinyl carbonylamino, N-morpholinylsulfonyl or N-pyrrolidinylcarbonylamino;
$R_{11}$ and $R_{12}$ are, independently, H, F, Cl, or methyl;
$Ar_1$ is

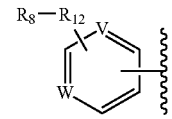

where
W and V are, independently, N, $CR_1$ or $CR_2$;
$R_8$, $R_9$ and $R_{10}$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, or methylsulfonyl, and $R_{10}$ may also be nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholinylcarbonylamino, N-morpholinylsulfonyl or N-pyrrolidinylcarbonylamino;
$R_{11}$ and $R_{12}$ are, independently, H, F, Cl or methyl;
$Ar_2$ is

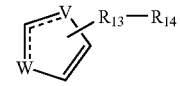

where
the dashed line represents a double bond which may be located formally either between V and the carbon between W and V, or between W and the carbon between W and V;
W is —S—, —O— or —N=, wherein
  when W is —O— or —S—, V is —CH=, —CCl= or —N=; and
  when W is —N=, V is CH= or —$NCH_3$—;
$R_{13}$ and $R_{14}$ are, independently, H, methoxycarbonyl, methylcarbamoyl, acetamido, acetyl, methyl, ethyl, trifluoromethyl or halogen;
$Ar_3$ is

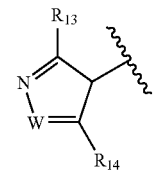

where
W is —NH—, —$NCH_3$— or —O—; and
$R_{13}$ and $R_{14}$ are, independently, H, F, Cl, or methyl.

2. A compound according to claim 1, which is of formula II-A.

3. A compound according to claim 1, which is of formula II-B.

4. A compound according to claim 1, which is of formula II-C.

5. A compound according to claim 1, which is of formula II-E.

6. A compound according to claim 1, which is of formula II-F.

7. A compound according to claim 1, or a pharmaceutically acceptable salt thereof.

8. A compound according to claim 1, where
X is F, Cl, or $CH_3$;
Y is I, Br, Cl, $CF_3$, or C1-C3 alkyl; and
Z is H or F.

9. A compound according to claim 1, where
$R_o$ is F, Cl, C1-C4 alkyl or C1-C4 alkoxy, said C1-C4 alkyl group and the C1-C4 alkyl moiety of said C1-C4 alkoxy group being optionally substituted with F, Cl, $OCH_3$, or $OCH_2CH_3$.

10. A compound according to claim 1, where
G is $CH_3$;
$R_o$ is H; and
Y is Br, I, $CF_3$, or $CH_3$.

11. A compound according to claim 1, where
$R_o$ is H;
F, or $OCH_3$;
X is F or $CH_3$, and
Y is Br, I, or $CH_3$.

12. A compound according to claim 1, where
$R_o$ is H;
$R_{8-10}$ are H;
$R_{11}$ and $R_{12}$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, or methylsulfonyl;
X is F; and
Y is I.

13. A compound according to claim 1, where
G is phenyl, optionally substituted with one group selected from the group consisting of acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl; optionally substituted with 1-3 substituents independently selected from the group consisting of F, Cl, and $CH_3$;
$R_o$ is H;
X is F, Cl, or methyl; and
Y is Br, I, $CF_3$, C1-C3 alkyl, C2-C3 alkenyl, C2-C3 alkynyl, cyclopropyl, $OCH_3$, $OCH_2CH_3$ or $SCH_3$.

14. A compound according to claim 1, where
G is

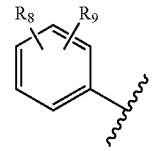

where
$R_8$ and $R_9$ are, independently, H, F, Cl, $CH_3$, $CF_3$, or $OCF_3$;
X is F or $CH_3$;
Y is I, Br, or Cl; and
Z is F.

15. A compound according to claim 1, where
$R_o$ is H,
W is N or $CR_2$;
V is $CR_3$;
X is F, Cl, or methyl; and
Y is Br, I, $CF_3$, C1-C3 alkyl, C2-C3 alkenyl, C2-C3 alkynyl, cyclopropyl, $OCH_3$, $OCH_2CH_3$ or $SCH_3$.

16. A compound according to claim 1, where
where G is

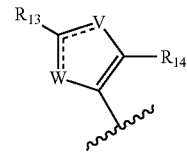

where
$R_{14}$ is H or methyl,
$R_{13}$ is H, acetamido, methyl, F or Cl;
$R_0$ is H;
X is F, Cl, or methyl;
Y is Br, I, $CF_3$, C1-C3 alkyl, C2-C3 alkenyl, C2-C3 alkynyl, cyclopropyl, $OCH_3$, $OCH_2CH_3$ or $SCH_3$; and
Z is F.

17. A compound according to claim 1, where G is isopropyl or cyclopropyl.

18. A pharmaceutical composition comprising a compound according to claim 1 and a pharmaceutically acceptable carrier.

19. A pharmaceutical composition according to claim 18, which is substantially free of the S isomer of the compound of formula II-A, II-B, II-C, II-E or II-F.

20. A method of treating breast cancer, comprising administering to a mammal in need of treatment a therapeutically effective amount of a compound according to claim 1.

* * * * *